US 10,611,827 B2

(12) United States Patent
Aman et al.

(10) Patent No.: US 10,611,827 B2
(45) Date of Patent: Apr. 7, 2020

(54) NON-HUMAN PRIMATE-DERIVED PAN-EBOLA AND PAN-FILOVIRUS MONOCLONAL ANTIBODIES DIRECTED AGAINST ENVELOPE GLYCOPROTEINS

(71) Applicants: INTEGRATED BIOTHERAPEUTICS, INC., Rockville, MD (US); THE BOARD OF TRUSTEES OF THE LELAND STANFORD JUNIOR UNIVERSITY, Stanford, CA (US)

(72) Inventors: Mohammad Javad Aman, Rockville, MD (US); Frederick Wayne Holtsberg, Taneytown, MD (US); Sven G. Enterlein, Berlin (DE); Katie A. Howell, Baltimore, MD (US); Zhen-Yong Keck, Redwood City, CA (US); Steven K. H. Foung, Stanford, CA (US)

(73) Assignees: INTEGRATED BIOTHERAPEUTICS, INC., Rockville, MD (US); THE BOARD OF TRUSTEES OF THE LELAND STANFORD JUNIOR UNIVERSITY, Stanford, CA (US)

(*) Notice: Subject to any disclaimer, the term of this patent is extended or adjusted under 35 U.S.C. 154(b) by 0 days.

(21) Appl. No.: 15/522,357

(22) PCT Filed: Oct. 27, 2015

(86) PCT No.: PCT/US2015/057627
§ 371 (c)(1),
(2) Date: Apr. 27, 2017

(87) PCT Pub. No.: WO2016/069627
PCT Pub. Date: May 6, 2016

(65) Prior Publication Data
US 2017/0334973 A1 Nov. 23, 2017

Related U.S. Application Data

(60) Provisional application No. 62/069,664, filed on Oct. 28, 2014.

(51) Int. Cl.
C07K 16/10 (2006.01)
G01N 33/569 (2006.01)
A61K 39/00 (2006.01)
A61K 39/42 (2006.01)

(52) U.S. Cl.
CPC ....... *C07K 16/10* (2013.01); *G01N 33/56983* (2013.01); *A61K 39/42* (2013.01); *A61K 2039/505* (2013.01); *C07K 2317/21* (2013.01); *C07K 2317/24* (2013.01); *C07K 2317/30* (2013.01); *C07K 2317/31* (2013.01); *C07K 2317/34* (2013.01); *C07K 2317/52* (2013.01); *C07K 2317/56* (2013.01); *C07K 2317/565* (2013.01); *C07K 2317/622* (2013.01); *C07K 2317/76* (2013.01); *C07K 2317/92* (2013.01); *C07K 2319/00* (2013.01); *G01N 2333/08* (2013.01); *G01N 2469/10* (2013.01)

(58) Field of Classification Search
CPC ............... C07K 16/10; C07K 2317/21; C07K 2317/565; C07K 2317/56; A61K 39/42
See application file for complete search history.

(56) References Cited

U.S. PATENT DOCUMENTS

2017/0158753 A1   6/2017  Aman et al.

OTHER PUBLICATIONS

Winkler, K., et al., 2000, Changing the antigen binding specificity by single point mutations of an anti-p24 (HIV-1) antibody, J. Immunol. 165:4505-4514.*
Kala, M., et al., 2002, Phage displayed antibodies to heat stable alkaline phosphatase: framework region as a determinant of specificity, J. Biochem. 132:535-541.*
Liu, Z., et al., 1999, Fine mapping of the antigen-antibody interaction of scFv215, a recombinant antibody inhibiting RNA polymerase II from *Drosophila melanogaster*, J. Mol. Recog. 12:103-111.*
Messaoudi, I., et al., Filovirus pathogenesis and immune evasion: insights from Ebola virus and Marburg virus, Nat. Rev. Immunol. 13:663-676.*
Kugelman, J. R., et al., 2015, Emergence of Ebola virus escape variants in infected nonhuman primates treated with MB-003 antibody cocktail, Cell Reports 12:2111-2120.*
Zeitlin, L., et al., 2016, Antibody therapeutics for Ebola virus disease, Curr. Opin. Virol. 17:45-49.*
Bradfute, S. B., 2017, The early clinical development of Ebola virus treatments, Exp. Opin. Invest. Drugs 26(1):1-4.*
Bray et al., "A Mouse Model for Evaluation of Prophylaxis and Therapy of Ebola Hemorrhagic Fever", Journal of Infectious Disease, 1998, pp. 651-661, vol. 178.
Carette et al., "Ebola Virus Entry Requires the Cholesterol Transporter Niemann-Pick C1", Nature, 2011, pp. 340-343, vol. 477, Issue 7364.
Chandran et al., "Endosomal Proteolysis of the Ebola Virus Glycoprotein is Necessary for Infection", Science, Jun. 10, 2005, pp. 1643-1645, vol. 308, Issue 5728.
Changula et al., "Mapping of Conserved and Species-specific Antibody Epitopes on the Ebola Virus Nucleoprotein", Virus Research, May 20, 2013, pp. 83-90, vol. 176.
Dube et al., "The Primed Ebolavirus Glycoprotein (19-Kilodalton GP 1,2): Sequence and Residues Critical for Host Cell Binding", Journal of Virology, Apr. 2009, pp. 2883-2891, vol. 83, No. 7.

(Continued)

*Primary Examiner* — Jeffrey S Parkin
(74) *Attorney, Agent, or Firm* — Thompson Coburn LLP; William A. Holtz

(57) ABSTRACT

The disclosure provides non-human primate-derived binding molecules, e.g., antibodies or antigen-binding fragments thereof, that can bind to orthologous epitopes found on two or more filovirus species or strains.

Figure 1:
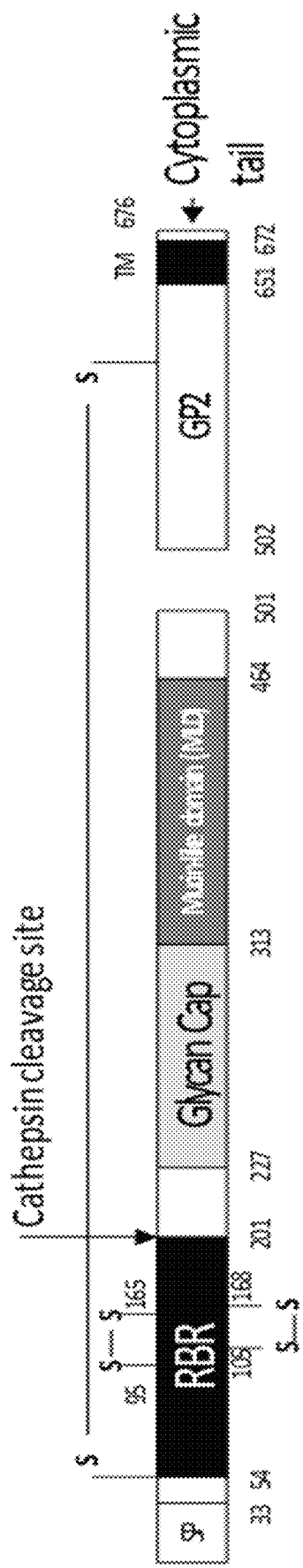

11 Claims, 16 Drawing Sheets
Specification includes a Sequence Listing.

(56) References Cited

OTHER PUBLICATIONS

Dye et al., "Postexposure Antibody Prophylaxis Protects Nonhuman Primates from Filovirus Disease", Proceedings of the National Academy of Science, Mar. 27, 2012, pp. 5034-5039, vol. 109, No. 13.
Feldmann et al., "Ebola Virus: From Discovery to Vaccine", Nature Reviews Immunology, Aug. 2003, pp. 677-685, vol. 3.
Feldmann et al., "Therapy and Prophylaxis of Ebola Virus Infections", Current Opinion in Investigational Drugs, 2005, pp. 823-830, vol. 6, No. 8.
Flyak et al., "Mechanism of Human Antibody-Mediated Neutralization of Marburg Virus", Cell, 2015, pp. 893-903, vol. 160.
Geisbert et al., "Prospects for Immunisation Against Marburg and Ebola Virus", Reviews in Medical Virology, Nov. 2010, pp. 344-357, vol. 20, No. 6.
Goncalvez et al., "Chimpanzee Fab Fragmnents and a Derived Humanized Immunoglobin G1 Antibody that Efficiently Cross-Neutralized Dengue Type 1 and Type 2 Viruses", Journal of Virology, Dec. 2004, pp. 12910-12918, vol. 78, No. 23.
Hashiguchi et al., "Structural Basis for Marburg Virus Neutralization by a Cross-Reactive Human Antibody", Cell, 2015, pp. 904-912, vol. 160.
International Search Report and Written Opinion for PCT/US2015/057627 dated Mar. 11, 2016.
Kaletsky et al., "Proteolysis of the Ebola Virus Glycoproteins Enhances Virus Binding and Infectivity", Journal of Virology, Dec. 2007, pp. 13378-13384, vol. 81, No. 24.
Keck et al., "Cooperativity in Virus Neutralization by Human Monoclonal Antibodies to Two Adjacent Regions Located at the Amino Terminus of Hepatitis C Virus E2 Glycoprotein", Journal of Virology, Jan. 2013, pp. 37-51, vol. 87, No. 1.
Keck et al., "Human Monoclonal Antibodies to a Novel Cluster of Conformational Epitopes on HCV E2 with Resistance to Neutralization Escape in a Genotype 2a Isolate", PLOS Pathogens, Apr. 2012, 21 pages, vol. 8, Issue 4, e1002653.
Kuhn et al., "Conserved Receptor-Binding Domains of Lake Victoria Marburgvirus and Zaire Ebolavirus Bind a Common Receptor", The Journal of Biological Chemistry, Jun. 9, 2006, pp. 15951-15958, vol. 281, No. 23.
Lee et al., "Structure of the Ebola Virus Glycoprotein Bound to an Antibody from a Human Survivor", Nature, Jul. 10, 2008, pp. 177-183, vol. 454.
Li et al., "Angiotensin-Converting Enzyme 2 is a Functional Receptor for the SARS Coronavirus", Nature, Nov. 27, 2003, pp. 450-454, vol. 426, No. 6965.
Loubiere et al., "Economic Evaluation of Point-of-Care Diagnostic Technologies for Infectious Diseases", Clinical Microbiology and Infection, 2010, pp. 1070-1076, vol. 16.
Maruyama et al., "Ebola Virus can be Effectively Neutralized by Antibody Produced in Natural Human Infection", Journal of Virology, Jul. 1999, pp. 6024-6030, vol. 73, No. 7, American Society of Microbiology.
Offermann et al., "Development and Validation of a Lateral Flow Assay (LFA) for the Determination of IgG-Antibodies to Pr3 (cANCA) and MPO (pANCA)", Journal of Immunological Methods, 2014, pp. 1-6, vol. 403.
Olinger, Jr., et al., "Delayed Treatment of Ebola Virus Infection with Plant-Derived Monoclonal Antibodies Provides Protection in Rhesus Macaques", Proceedings of the National Academy of Sciences, Oct. 30, 2012, pp. 18030-18035, vol. 109, No. 44.
Ou, et al., "Development and Characterization of Rabbit and Mouse Antibodies Against Ebolavirus Enevlope Glycoproteins", Journal of Virological Methods, 2011, pp. 99-109, vol. 174, Elsevier B.V.
Pfeilsticker et al., "A Cocktail of Thermally Stable, Chemically Synthesized Capture Agents for the Efficient Detection of Anti-Gp41 Antibodies from Human Sera", PLOS One, Oct. 2013, 5 pages, vol. 8, Issue 10, e76224.
Qiu et al., "mAbs and Ad-Vectored IFN-a Therapy Rescue Ebola-Infected Nonhuman Primates When Administered After the Detection of Viremia and Symptoms", Science Translational Medicine, Oct. 16, 2013, 10 pages, vol. 5, Issue 207, 207ra143.
Qiu et al., "Monoclonal Antibodies Combined with Adenovirus-Vectored Interferon Significantly Extend the Treatment Window in Ebola Virus-Infected Guinea Pigs", Journal of Virology, Jul. 2013, pp. 7754-7757, vol. 87, No. 13.
Radoshitzky et al., "Transferrin Receptor 1 is a Cellular Receptor for New World Haemorrhagic Fever Arenaviruses", Nature, Mar. 2007, pp. 92-96, vol. 446.
Sanchez et al., "The Virion Glycoproteins of Ebola Viruses Are Encoded in Two Reading Frames and Are Expressed Through Transcriptional Editing", Proceedings of the National Academy of Sciences USA, Apr. 1996, pp. 3602-3607, vol. 93.
Schornberg et al., "Role of Endosomal Cathepsins in Entry Mediated by the Ebola Virus Glycoprotein", Journal of Virology, Apr. 2006, pp. 4174-4178, vol. 80, No. 8.
Wang et al., "Cellulose-Based Diagnostic Devices for Diagnosing Serotype-2 Dengue Fever in Human Serum", Advanced Healthcare Materials, 2014, pp. 187-196, vol. 3.
Warfield et al., "Induction of Humoral and CD8+ T Cell Responses Are Required for Protection Against Lethal Ebola Virus Infection", The Journal of Immunology, 2005, pp. 1184-1191, vol. 175.
Wilson et al., "Protection from Ebola Virus Mediated by Cytotoxic T Lymphocytes Specific for the Viral Nucleoprotein", Journal of Virology, Mar. 2001, pp. 2660-2664, vol. 75, No. 6.
Wong et al., "A 193-Amino Acid Fragment of the SARS Coronavirus S Protein Efficiently Binds Angiotensin-Converting Enzyme 2*", The Journal of Biological Chemistry, Jan. 30, 2004, pp. 3197-3201, vol. 279, No. 5.
Yetisen et al., "Paper-Based Microfluidic Point-of-Care Diagnostic Devices", Lab on a Chip, 2013, pp. 2210-2251, vol. 13.

* cited by examiner

```
MARV-RBR   38  SGTHQIEDVHLMGTTLSGQKVADSPLEASKRWAFRTGVPPKNIETEGEATCVNISVTDRGKSLILDPRTNIR
SUDV-RBR   54  KDHIASTDQLKSVGLNLEGSGVSTDIFSATKRWGFRSGVPPKVISVEAGEWAENCVNLEIKKPDGSECLPPPDGVR
ZEBOV-RBR  54  RDKISSTNQLRSVGLNLEGNGVATDVPSATKRWGFRSGVPPKVINEAGEWAENCINLEIKKPDGSECLPAARDGIR
Consensus      KD LASTDQLKSVGLNLEGNGVATDIPSATKRWGFRSGVPPKVV  YEAGEWAENCYNLEIKKPDGSECLP PPDGIR MARV-RBR       DYPRCKTIHNIQGQVRHAQGIAIHLMGAFFLYDRLASTMIRGKVFIEGNIRAMIVNKTVHKMIFSRQGQGYRH  188
SUDV-RBR       GFPRCRYVHKAQGTGPCPGDYAFHKDGAFFLYDRLASTVIRGVNEAEGVIAFLILAKPKETFLQSPPIRE----  201
ZEBOV-RBR      GFPRCRYVHKVSGTGPCAGDFAFHKEGAFFLYDRLASTVIIRGTFAEGVVAFLILPQAKKDFFSSHPLRE----  201
Consensus      GFPRCRYVHKIQGTGPCAGDFAEHKDGAFFLYDRLASTVIYRG   FAEGVIAFLIL K K  FI S PIRE
```

Figure 2

Figure 3A

| | GPΔmuc | GPcl | sGP | Putative Binding Region |
|---|---|---|---|---|
| FVM01p | 0.009 | 0.005 | 0.005 | Core |
| FVM02p | 0.010 | 0.005 | NR | GP2 |
| FVM04 | 0.012 | 0.008 | 0.007 | Core |
| FVM09 | 0.005 | NR | 0.017 | Glycan Cap |
| FVM13 | 0.003 | >10 | 0.005 | Glycan Cap |
| FVM20 | 0.007 | >10 | 0.023 | Glycan Cap |

Figure 6

A

```
Z56  KVNPEIDTTGEWAF
Z57      IDTTGEWAFWETKK
Z58          GEWAFWETKKNLTRK
Z59             WETKKNLTRKIRSEE
Z60                  NLTRKIRSEELSFTV
```

FVM09

B

C

```
EBOV   280  EIDTTIGEWAFWETKKN
SUDV   280  NINADIGEWAFWENKKN
BDBV   280  TVDTGVGEWAFWETKKN
RESTV  280  KIEPDVGEWAFWETKKN
TAFV   280  TVDTSMGEWAFWETKKN
```

Figures 7A, 7B and 7C

D

| | |
|---|---|
| Z103 | CNPNLHYWTTQDEGA |
| Z104 | HYWTTQDEGAAIGLA |
| Z105 | QDEGAAIGLAWIPY |
| Z106 | AIGLAWIPYFGPAAE |
| Z107 | WIPYFGPAAEGIYTE |

FVM02P

■ FVM02P

E

F

| | | |
|---|---|---|
| EBOV | 525 | AAIGLAWIPYFGPAA |
| SUDV | 525 | AAIGLAWIPYFGPGA |
| RESTV | 525 | AAAGLAWIPYFGPAA |
| TAFV | 525 | AAIGLAWIPYFGPAA |
| BDBV | 525 | AAIGLAWIPYFGPAA |
| MARV_Angola | 526 | AA-GLSWIPFFGPGI |
| MARV_Popp | 526 | AA-GLSWIPFFGPGI |
| MARV_Musoke | 526 | AA-GLSWIPFFGPGI |
| MARV_RAVN | 526 | AA-GLSWIPFFGPGI |
| MARV_CI67 | 526 | AA-GLSWIPFFGPGI |

Figures 7D, 7E and 7F

Trough exposed after cathepsin cleavage

Figures 9A and 9B

NON-HUMAN PRIMATE-DERIVED PAN-EBOLA AND PAN-FILOVIRUS MONOCLONAL ANTIBODIES DIRECTED AGAINST ENVELOPE GLYCOPROTEINS

CROSS-REFERENCE TO RELATED APPLICATIONS

This patent application is a 35 U.S.C. § 371 National Phase Application of International Patent Application No. PCT/US2015/057627, filed Oct. 27, 2015, which claims the benefit of U.S. Provisional Application No. 62/069,664, filed Oct. 28, 2014, both of which are incorporated herein by reference in their entireties.

GOVERNMENT RIGHTS

This invention was made with Government support under contract AI098178 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said Sequence Listing, created on May 19, 2017, is named "57783_165425_Substitute Seq List_ST25.txt" and is 167,560 bytes in size.

BACKGROUND

Filoviruses, e.g., ebolavirus and marburgvirus, cause severe hemorrhagic fevers in humans, with mortality rates reaching 88% (Feldmann, et al., 2003, Nat Rev Immunol, 3 (8):677-685) as well as epizootics in nonhuman primates and probably other mammals. Due to weaponization of marburgvirus by the USSR, the high fatality rates, and the potential for aerosol transmission filoviruses have been classified as Category A NIAID Priority Pathogens. There are currently no vaccines or therapeutics against filoviruses. The main filovirus species causing outbreaks in humans are ebolaviruses Zaire (EBOV) and Sudan (SUDV), as well as the Lake Victoria Marburg virus (MARV). Filoviruses are enveloped, single-stranded, negative sense RNA filamentous viruses and encode seven proteins, of which the spike glycoprotein (GP) is considered the main protective antigen. EBOV and MARV GP can be proteolytically cleaved by furin protease into two subunits linked by a disulfide linkage: GP1 (~140 kDa) and GP2 (~38 kDa) (Manicassamy, et al., 2005, J Virol, 79 (8):4793-4805). Three GP1-GP2 units form the trimeric GP envelope spike (~550 kDa) on the viral surface (Feldmann, et al., 1993, Arch Virol Suppl, 7:81-100; Feldmann, et al., 1991, Virology, 182 (1):353-356; Geisbert and Jahrling, 1995, Virus Res, 39 (2-3):129-150; Kiley, et al., 1988a, J Gen Virol, 69 (Pt 8):1957-1967). GP1 mediates cellular attachment (Kiley, et al., 1988b, J Gen Virol, 69 (Pt 8):1957-1967; Kuhn, et al., 2006, J Biol Chem, 281 (23): 15951-15958), and contains a mucin-like domain (MLD) which is heavily glycosylated and variable and has little or no predicted secondary structure (Sanchez, et al., 1998, J Virol, 72 (8):6442-6447).

It is well established that the filovirus GP represent the primary protective antigens (Feldmann, et al., 2003, Nat Rev Immunol, 3 (8):677-685; Feldmann, et al., 2005, Curr Opin Investig Drugs, 6 (8):823-830; Geisbert, et al., 2010, Rev Med Virol, 20(6):344-57). GP consists of a receptor binding GP1 subunit connected with the GP2 fusion domain via a disulfide link (FIG. 1). We have previously identified a specific region of the MARV and EBOV GP1 consisting of ~150 amino acids (Kuhn, et al., 2006, J Biol Chem, 281 (23):15951-15958) that binds filovirus receptor-positive cells, but not receptor-negative cells, more efficiently than $GP_1$, and compete with the entry of the respective viruses (Kuhn, et al., 2006, J Biol Chem, 281 (23):15951-15958). These properties are similar to regions defined for SARS coronavirus and Machupo arenavirus (Li, et al., 2003, Nature, 426 (6965):450-454; Radoshitzky, et al., 2007, Nature, 446 (7131):92-96; Wong, et al., 2004, J Biol Chem, 279 (5):3197-3201). This region of GP is referred to here as receptor binding region (RBR) and is part of a larger domain that excludes the variable, glycosylated, and bulky mucin-like domain (MLD). The RBR shows the highest level of homology between Filovirus glycoproteins (Kuhn, et al., 2006, J Biol Chem, 281 (23):15951-15958) as shown in FIG. 2. Therefore, the RBR represents a potential target for pan-filovirus antibodies.

The crystal structure of a trimeric, pre-fusion conformation of EBOV GP (lacking MLD) in complex with a EBOV-specific neutralizing antibody, KZ52 was solved at 3.4 Å (Lee, et al., 2008, Nature, 454 (7201):177-182). In this structure, three GP1 subunits assemble to form a chalice, cradled in a pedestal of the GP2 fusion subunits, while the MLD restricts access to the conserved RBR, sequestered in the GP chalice bowl. Ebola and Marburg GPs are cleaved by cathepsin proteases as a step in entry reducing GP1 to an ~18 kDa product (Chandran, et al., 2005, Science, 308 (5728): 1643-1645; Kaletsky, et al., 2007, J Virol, 81 (24):13378-13384; Schomberg, et al., 2006, J Virol, 80 (8):4174-4178). The structures suggest that the most likely site of cathepsin cleavage is the flexible β13-β14 loop of GP1 and illustrate how cleavage there can release the heavily glycosylated regions from GP, leaving just the core of GP1, encircled by GP2, with the RBR now well exposed. Cathepsin cleavage enhances attachment; presumably better exposing the RBR for interaction with cell surface factors trafficked with the virus into the endosome (Dube, et al., 2009, J Virol, 83:2883-2891).

Role of Antibodies in Protection Against Filovirus Hemorrhagic Fever.

While both T and B cell responses are reported to play a role in protective immune responses to filoviruses (Warfield, et al., 2005, J Immunol, 175 (2):1184-1191), a series of recent reports indicate that antibody alone can provide protection. Dye et al showed that purified convalescent IgG from macaques can protect non-human primates (NHPs) against challenge with MARV and EBOV when administered as late as 48 h post exposure (Dye, et al., 2012, Proc Natl Acad Sci USA, 109(13):5034-9). Olinger et al reported protection from EBOV challenge in NHPs treated with a cocktail of three monoclonal antibodies (mAbs) to GP administered 24 h and 48 h post exposure (Olinger, et al., 2012, Proc Natl Acad Sci USA, 109 (44):18030-18035). Similar results were also reported in two other studies (Qiu, et al., 2013, Sci Transl Med, 5 (207):207ra143; Qiu, et al., 2013, J Virol, 87 (13):7754-7757). Collectively these data demonstrate that a humoral response can control, alleviate, reduce, or prevent, filovirus infection.

Figure 3A:
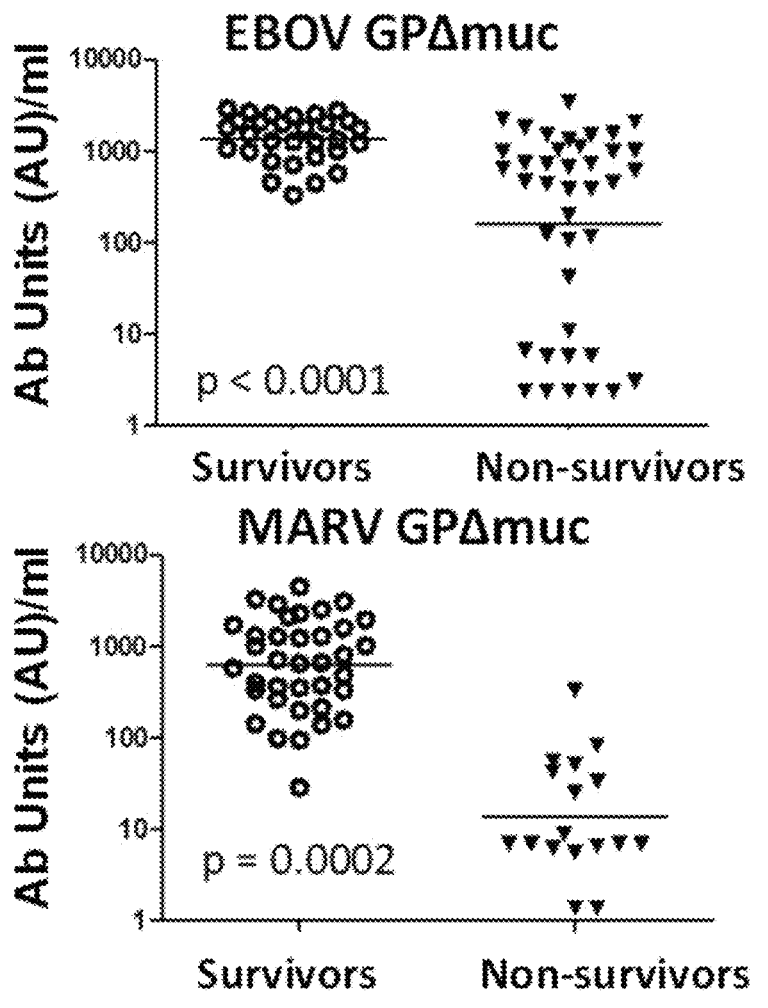
Figure 3B:
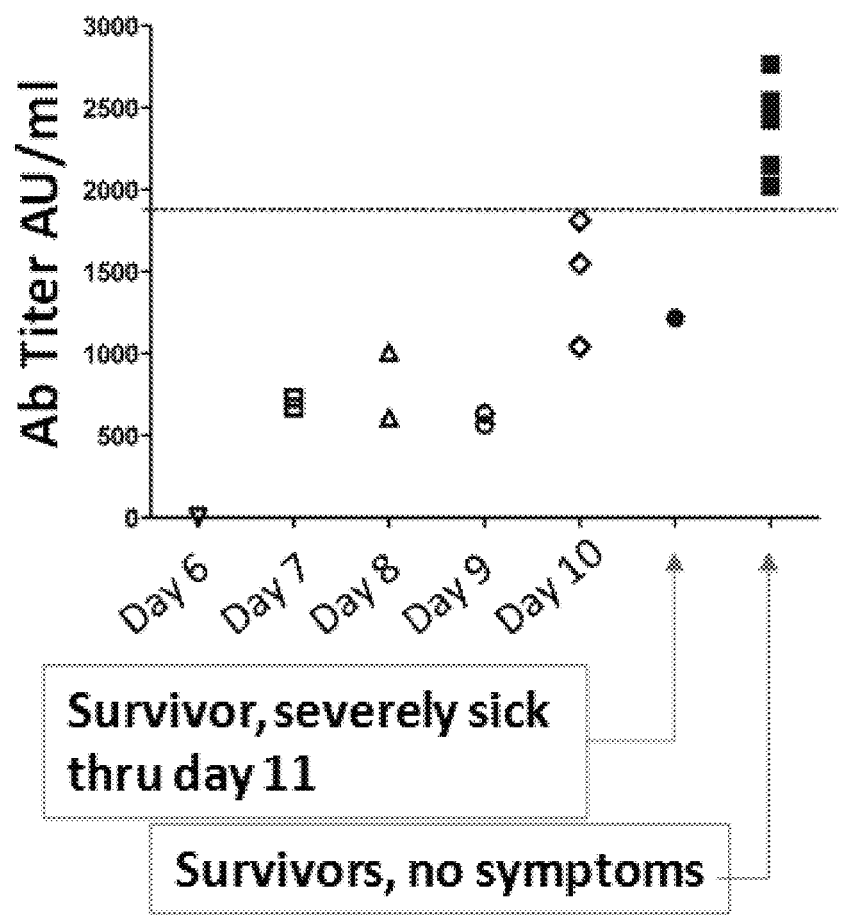

To further explore the role of antibodies in protection against filoviruses in the context of vaccination, we performed an analysis of historical data from studies performed with virus-like particle (VLP) vaccines in >120 macaques to evaluate the relationship between protection from lethal challenge with antibody response to purified EBOV or MARV purified recombinant glycoproteins without the mucin-like domain and transmembrane region (GPddmuc). It was observed that an increase in antibody levels against the GPddmuc antigens can be associated with an increased probability of survival following lethal challenge (FIG. 3A). This relationship was not observed in the antibody levels to the matrix protein VP40 or irradiated, whole EBOV antigen (not shown). Analysis of the neutralizing antibody titer also demonstrated an association with survival for EBOV, supporting the hypothesis that neutralizing antibodies recognizing the RBR can provide protection from lethal infection. The majority of the data shown in FIG. 3A are from studies with VLPs expressing GP, VP40, and the nucleoprotein NP. Since it is known that NP induces strong cytotoxic T cell responses (Wilson and Hart, 2001, *J Virol*, 75 (6):2660-2664), it is possible that contribution of anti-NP T cell response to protection can impact our ability to fully decipher the role of antibodies in this analysis. Therefore, we analyzed data from a recent study using VLPs expressing GP and VP40. Fifteen cynomolgus macaques were vaccinated twice with various doses of GP/VP40 along with QS21 adjuvant and challenged 28 days later with 1000 PFU of EBOV. Both controls and nine of the vaccinated NHP died while six animals survived. Analysis of antibody response to GPddmuc in sera of these animals demonstrated a clear relationship between antibody titers to GPddmuc and survival with an apparent cut off at an antibody titer of ~2000 AU/ml (FIG. 3B). This correlation became more obvious when the time of death of these animals was plotted against the antibody titer (FIG. 3B). One animal with an antibody titer below 2000 survived the challenge and this animal was very sick through day 14. This clearly indicates that vaccination with the GPddmuc proteins and likely proteins containing only the RBR could generate antibodies that could provide protection against infection.

SUMMARY

This disclosure provides an isolated binding molecule or antigen-binding fragment thereof derived from a non-human primate (NHP), e.g., a macaque, e.g., a rhesus macaque, where the NHP-derived binding molecule includes a binding domain that specifically binds to an orthologous filovirus glycoprotein epitope, where the binding domain specifically binds to the epitope on two or more filovirus species or strains, for example, Marburg virus (MARV), Sudan virus (SUDV), Ebola virus (EBOV), or any combination thereof. In certain aspects the binding domain can bind to the orthologous epitope as expressed in MARV, EBOV, and SUDV; MARV; or EBOV and SUDV.

In certain aspects the binding domain can bind to the orthologous epitope as expressed in at least EBOV, SUDV, and MARV. In certain aspects the binding domain can bind to the same orthologous epitope as an antibody or antigen-binding fragment thereof including a heavy chain variable region (VH) and light chain variable region (VL) including, respectively, the amino acid sequences SEQ ID NO: 12 and 17, or can competitively inhibit antigen binding by an antibody or antigen-binding fragment thereof including a heavy chain variable region (VH) and light chain variable region (VL) including, respectively, the amino acid sequences SEQ ID NO: 12 and 17.

In certain aspects the binding domain can bind to the orthologous epitope as expressed in at least MARV. In certain aspects the binding domain can bind to the same orthologous epitope as an antibody or antigen-binding fragment thereof including a heavy chain variable region (VH) and light chain variable region (VL) including the amino acid sequences SEQ ID NO: 22 and 27, or can competitively inhibit antigen binding by an antibody or antigen-binding fragment thereof including a heavy chain variable region (VH) and light chain variable region (VL) including the amino acid sequences SEQ ID NO: 22 and 27.

In certain aspects the binding domain can bind to the orthologous epitope as expressed in EBOV and SUDV. In certain aspects the binding domain can bind to the same orthologous epitope as an antibody or antigen-binding fragment thereof including a heavy chain variable region (VH) and light chain variable region (VL) including the amino acid sequences SEQ ID NO: 2 and SEQ ID NO: 7; SEQ ID NO: 32 and SEQ ID NO: 37; SEQ ID NO: 42 and SEQ ID NO: 47; SEQ ID NO: 52 and SEQ ID NO: 57; SEQ ID NO: 62 and SEQ ID NO: 67; SEQ ID NO: 72 and SEQ ID NO: 57; SEQ ID NO: 82 and SEQ ID NO: 87; SEQ ID NO: 92 and SEQ ID NO: 97; SEQ ID NO: 82 and SEQ ID NO: 107; SEQ ID NO: 112 and SEQ ID NO: 117; SEQ ID NO: 122 and SEQ ID NO: 127; SEQ ID NO: 132 and SEQ ID NO: 137; SEQ ID NO: 142 and SEQ ID NO: 57; SEQ ID NO: 152 and SEQ ID NO: 157; SEQ ID NO: 162 and SEQ ID NO: 167; SEQ ID NO: 172 and SEQ ID NO: 177; SEQ ID NO: 182 and SEQ ID NO: 187; SEQ ID NO: 192 and SEQ ID NO: 197; SEQ ID NO: 202 and SEQ ID NO: 207; SEQ ID NO: 212 and SEQ ID NO: 217; SEQ ID NO: 222 and SEQ ID NO: 227; SEQ ID NO: 232 and SEQ ID NO: 237; SEQ ID NO: 242 and SEQ ID NO: 247; SEQ ID NO: 142 and SEQ ID NO: 57; SEQ ID NO: 262 and SEQ ID NO: 267; SEQ ID NO: 272 and SEQ ID NO: 277; SEQ ID NO: 282 and SEQ ID NO: 57; SEQ ID NO: 292 and SEQ ID NO: 297; SEQ ID NO: 302 and SEQ ID NO: 307; SEQ ID NO: 312 and SEQ ID NO: 57; SEQ ID NO: 322 and SEQ ID NO: 327; SEQ ID NO: 332 and SEQ ID NO: 57; SEQ ID NO: 342 and SEQ ID NO: 347; SEQ ID NO: 352 and SEQ ID NO: 357; SEQ ID NO: 362 and SEQ ID NO: 57; SEQ ID NO: 372 and SEQ ID NO: 57; SEQ ID NO: 382 and SEQ ID NO: 387; SEQ ID NO: 392 and SEQ ID NO: 397; or SEQ ID NO: 402 and SEQ ID NO: 407, or can competitively inhibit antigen binding by an antibody or antigen-binding fragment thereof including a heavy chain variable region (VH) and light chain variable region (VL) including the amino acid sequences SEQ ID NO: SEQ ID NO: 2 and SEQ ID NO: 7; SEQ ID NO: 32 and SEQ ID NO: 37; SEQ ID NO: 42 and SEQ ID NO: 47; SEQ ID NO: 52 and SEQ ID NO: 57; SEQ ID NO: 62 and SEQ ID NO: 67; SEQ ID NO: 72 and SEQ ID NO: 57; SEQ ID NO: 82 and SEQ ID NO: 87; SEQ ID NO: 92 and SEQ ID NO: 97; SEQ ID NO: 82 and SEQ ID NO: 107; SEQ ID NO: 112 and SEQ ID NO: 117; SEQ ID NO: 122 and SEQ ID NO: 127; SEQ ID NO: 132 and SEQ ID NO: 137; SEQ ID NO: 142 and SEQ ID NO: 57; SEQ ID NO: 152 and SEQ ID NO: 157; SEQ ID NO: 162 and SEQ ID NO: 167; SEQ ID NO: 172 and SEQ ID NO: 177; SEQ ID NO: 182 and SEQ ID NO: 187; SEQ ID NO: 192 and SEQ ID NO: 197; SEQ ID NO: 202 and SEQ ID NO: 207; SEQ ID NO: 212 and SEQ ID NO: 217; SEQ ID NO: 222 and SEQ ID NO: 227; SEQ ID NO: 232 and SEQ ID NO: 237; SEQ ID NO: 242 and SEQ ID NO: 247; SEQ ID NO: 142 and SEQ ID NO: 57; SEQ ID NO: 262 and SEQ ID NO: 267; SEQ ID NO: 272 and SEQ ID NO: 277; SEQ ID NO: 282 and SEQ ID NO: 57; SEQ ID NO: 292 and SEQ ID NO: 297; SEQ ID NO: 302 and SEQ ID NO: 307; SEQ ID NO: 312 and SEQ ID NO: 57; SEQ ID NO: 322 and SEQ ID NO: 327; SEQ ID NO: 332 and SEQ ID NO: 57; SEQ ID NO: 342 and SEQ ID NO: 347; SEQ ID NO: 352 and SEQ ID NO: 357; SEQ ID NO: 362 and SEQ ID NO: 57; SEQ ID NO: 372 and SEQ ID NO: 382 and SEQ ID NO: 387; SEQ ID NO: 392 and SEQ ID NO: 397; or SEQ ID NO: 402 and SEQ ID NO: 407.

In certain aspects the NHP-derived binding molecule or fragment thereof provided herein includes an antibody or antigen-binding fragment thereof where the binding domain includes VH-CDR1, VH-CDR2, VH-CDR3, VL-CDR1, VL-CDR2, and VL-CDR3 amino acid sequences identical or identical except for four, three, two, or one single amino acid substitutions, deletions, or insertions in one or more CDRs to: SEQ ID NOs 3, 4, 5, 8, 9, and 10; SEQ ID NOs 13, 14, 15, 18, 19, and 20; SEQ ID NOs 23, 24, 25, 28, 29, and 30; SEQ ID NOs 33, 34, 35, 38, 39, and 40; SEQ ID NOs 43, 44, 45, 48, 49, and 50; SEQ ID NOs 53, 54, 55, 58, 59, and 60; SEQ ID NOs 63, 64, 65, 68, 69, and 70; SEQ ID NOs 73, 74, 75, 58, 59, and 60; SEQ ID NOs 73, 84, 55, 58, 59, and 60; SEQ ID NOs 73, 84, 95, 58, 69, and 60; SEQ ID NOs 73, 84, 55, 58, 59, and 60; SEQ ID NOs 113, 74, 55, 58, 119, and 120; SEQ ID NOs 123, 74, 55, 58, 59, and 60; SEQ ID NOs 133, 84, 55, 58, 59, and 60; SEQ ID NOs 143, 84, 55, 58, 59, and 60; SEQ ID NOs 153, 84, 55, 58, 59, and 120; SEQ ID NOs 163, 164, 55, 58, 119, and 60; SEQ ID NOs 173, 84, 55, 68, 179, and 180; SEQ ID NOs 73, 64, 55, 68, 69, and 190; SEQ ID NOs 193, 84, 55, 68, 179, and 60; SEQ ID NOs 73, 84, 75, 58, 69, and 60; SEQ ID NOs 73, 84, 95, 58, 59, and 60; SEQ ID NOs 193, 224, 55, 58, 59, and 230; SEQ ID NOs 73, 234, 55, 58, 59, and 60; SEQ ID NOs 143, 244, 55, 58, 119, and 120; SEQ ID NOs 143, 84, 55, 58, 59, and 60; SEQ ID NOs 263, 264, 55, 58, 59, and 60; SEQ ID NOs 273, 274, 55, 68, 179, and 180; SEQ ID NOs 283, 274, 55, 58, 59, and 60; SEQ ID NOs 73, 164, 55, 58, 59, and 60; SEQ ID NOs 73, 74, 55, 308, 59, and 60; SEQ ID NOs 313, 74, 55, 58, 59, and 60; SEQ ID NOs 323, 84, 55, 68, 69, and 120; SEQ ID NOs 333, 84, 55, 58, 59, and 60; SEQ ID NOs 343, 84, 55, 58, 59, and 60; SEQ ID NOs 123, 84, 55, 58, 59, and 60; SEQ ID NOs 63, 84, 55, 58, 59, and 60; SEQ ID NOs 163, 84, 55, 58, 59, and 60; SEQ ID NOs 163, 84, 55, 58, 59, and 60; SEQ ID NOs 393, 84, 55, 58, 59, and 60; or SEQ ID NOs 73, 404, 55, 58, 59, and 60; respectively. In certain aspects the binding domain includes VH and VL amino acid sequences at least 85%, 90%, 95%, or 100% identical to reference amino acid sequences SEQ ID NO: 2 and SEQ ID NO: 7; SEQ ID NO: 12 and SEQ ID NO: 17; SEQ ID NO: 22 and SEQ ID NO: 27; SEQ ID NO: 32 and SEQ ID NO: 37; SEQ ID NO: 42 and SEQ ID NO: 47; SEQ ID NO: 52 and SEQ ID NO: 57; SEQ ID NO: 62 and SEQ ID NO: 67; SEQ ID NO: 72 and SEQ ID NO: 57; SEQ ID NO: 82 and SEQ ID NO: 87; SEQ ID NO: 92 and SEQ ID NO: 97; SEQ ID NO: 82 and SEQ ID NO: 107; SEQ ID NO: 112 and SEQ ID NO: 117; SEQ ID NO: 122 and SEQ ID NO: 127; SEQ ID NO: 132 and SEQ ID NO: 137; SEQ ID NO: 142 and SEQ ID NO: 57; SEQ ID NO: 152 and SEQ ID NO: 157; SEQ ID NO: 162 and SEQ ID NO: 167; SEQ ID NO: 172 and SEQ ID NO: 177; SEQ ID NO: 182 and SEQ ID NO: 187; SEQ ID NO: 192 and SEQ ID NO: 197; SEQ ID NO: 202 and SEQ ID NO: 207; SEQ ID NO: 212 and SEQ ID NO: 217; SEQ ID NO: 222 and SEQ ID NO: 227; SEQ ID NO: 232 and SEQ ID NO: 237; SEQ ID NO: 242 and SEQ ID NO: 247; SEQ ID NO: 142 and SEQ ID NO: 57; SEQ ID NO: 262 and SEQ ID NO: 267; SEQ ID NO: 272 and SEQ ID NO: 277; SEQ ID NO: 282 and SEQ ID NO: 57; SEQ ID NO: 292 and SEQ ID NO: 297; SEQ ID NO: 302 and SEQ ID NO: 307; SEQ ID NO: 312 and SEQ ID NO: 57; SEQ ID NO: 322 and SEQ ID NO: 327; SEQ ID NO: 332 and SEQ ID NO: 57; SEQ ID NO: 342 and SEQ ID NO: 347; SEQ ID NO: 352 and SEQ ID NO: 357; SEQ ID NO: 362 and SEQ ID NO: 57; SEQ ID NO: 372 and SEQ ID NO: 57; SEQ ID NO: 382 and SEQ ID NO: 387; SEQ ID NO: 392 and SEQ ID NO: 397; or SEQ ID NO: 402 and SEQ ID NO: 407; respectively. The antibody can be a NHP antibody, e.g., a macaque antibody, e.g., a rhesus macaque antibody, a humanized antibody, a chimeric antibody, or a fragment thereof, and/or can be a monoclonal antibody, a component of a polyclonal antibody mixture, a recombinant antibody, a multispecific antibody, or any combination thereof. In certain aspects the antibody or fragment thereof is a bispecific antibody or fragment thereof further including a second binding domain.

In certain aspects binding of the binding domain to the orthologous epitope on a filovirus fully or partially neutralizes infectivity of the filovirus.

The disclosure further provides a composition including the antibody or fragment thereof as provided herein, and a carrier, and a kit, including the antibody or antigen binding fragment thereof or composition as provided herein, and instructions for using the antibody or fragment thereof or using the composition or directions for obtaining instructions for using the antibody or fragment thereof or using the composition.

The disclosure further provides an isolated polynucleotide that includes a nucleic acid encoding the NHP-derived binding molecule or fragment thereof as provided herein or a subunit thereof, or the antibody or fragment thereof as provided herein; or a subunit thereof. Also provided is a vector comprising a polynucleotide as provided, and a host cell including the polynucleotide or combination of polynucleotides as provided or the vector or vectors as provided. The disclosure further provides a method of making the NHP-derived binding molecule or fragment thereof of or the antibody or fragment thereof as provided where the method includes culturing the provided host cell; and isolating the NHP-derived binding molecule or fragment thereof or antibody or fragment thereof.

The disclosure further provides a method for preventing, treating, or managing filovirus infection in a subject, where the method includes administering to a subject in need thereof an effective amount of the antibody or antigen binding fragment thereof as provided herein.

BRIEF DESCRIPTION OF THE DRAWINGS/FIGURES

FIG. 1: Domain structure of EBOV GP. SP: signal peptide, TM: Transmembrane domain, RBR: receptor binding region, MLD: Mucin-like domain. Cathepsin cleavage site and disulfide bonds are also shown.

FIG. 2: Sequence alignment of the receptor binding regions (RBR) of the three main filovirus species (SEQ ID NOS 417-419, respectively, in order of appearance). Identical residues are shown with gray highlight and divergent residues are shown in gray letters.

FIG. 3A-B: FIG. 3A: GPddmuc Ab responses were determined in sera of GP/VP40/NP VLP-vaccinated NHPs prior to lethal challenge with EBOV or MARV and correlated with survival. Significance was demonstrated using a one-sided t test. FIG. 3B: NHPs were vaccinated with VLPs containing only GP and VP40, Ab response to GPddmuc assessed, and challenged with EBOV. Survivors, black symbols; nonsurvivors, open symbols.

Figure 4:
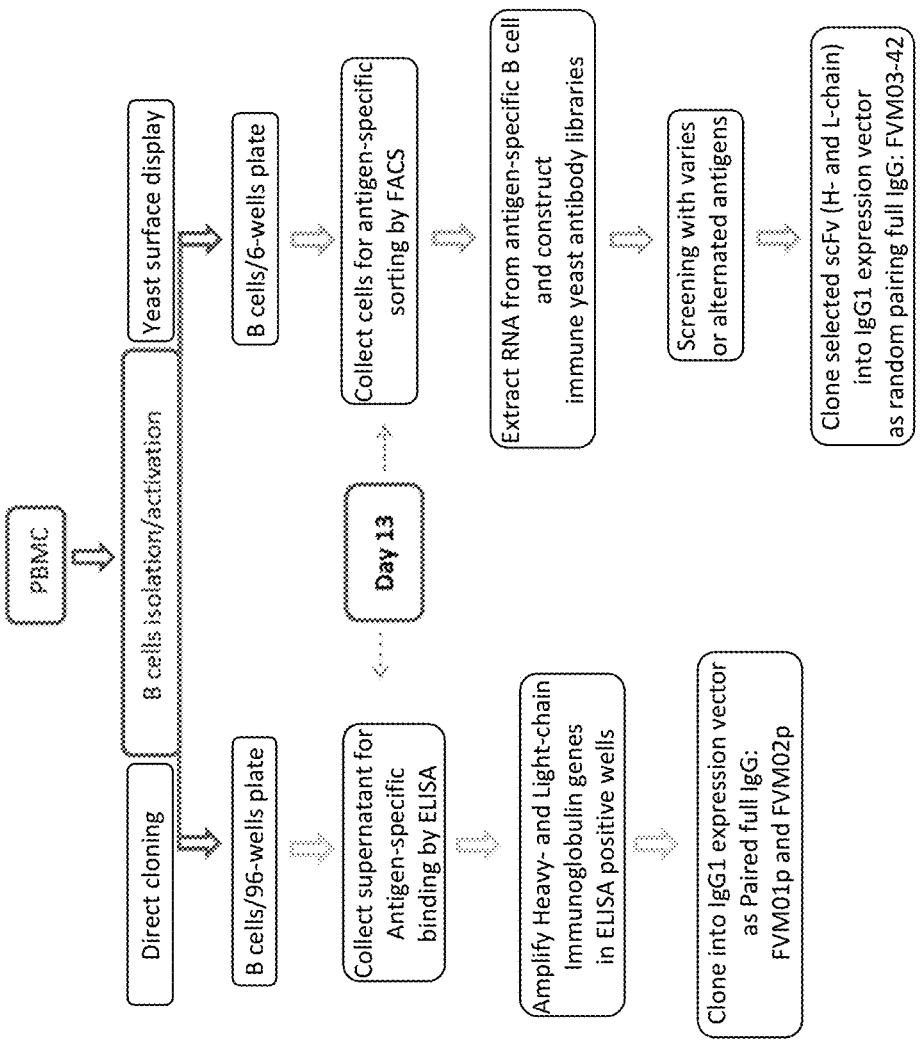

FIG. 4: Work flow diagram of isolation of filovirus-reactive macaque B cell clones.

Figure 5:
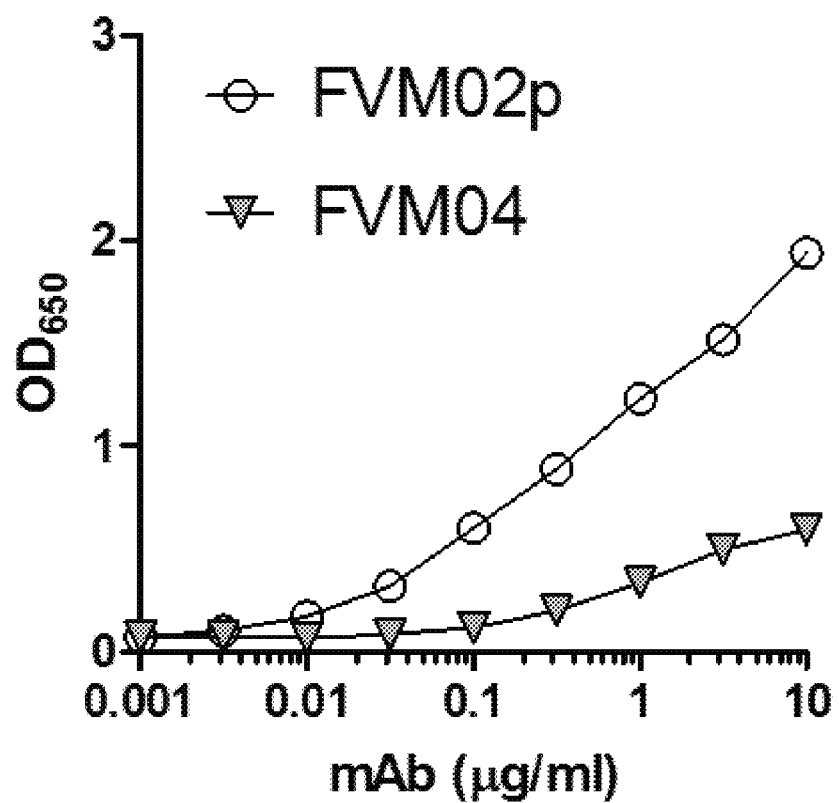

FIG. 5: Binding of FVM02p and FVM04 to His-tagged MARV GP (Angola) presented on $Ni^{++}$ coated plates determined by ELISA.

FIG. 6: Binding region of macaque filovirus antibodies. (Top) Structure of the MLD-deleted GP (GPΔmuc), EBOV GP after cleavage with thermolysin (GPcl), and EBOV soluble GP (sGP). Glycan cap is shown in black, the core/RBR (residues 31-200) in white, and GP in gray. (Bottom) Binding $EC_{50}$ values (μg/ml) for binding of each antibody to the respective antigen are shown in each panel. The putative binding regions deduced from the binding pattern are shown on the right. NR: non-reactive.

FIG. 7A-F: Epitope mapping of FVM02p and FVM09. Epitopes for FVM02p and FVM09 were determined by competition ELISA using overlapping peptides spanning the full EBOV GP sequence. Peptides were pre-incubated at 100 fold molar excess with FVM02p or FVM09 and binding of the antibodies in presence and absence of peptide was determined by ELISA. FIG. 7A shows the sequence of the five overlapping peptides (Top) surrounding the core sequence (boxed) that showed competition with FVM09 binding in ELISA (bottom) (SEQ ID NOS 420-424, respectively, in order of appearance). FIG. 7B shows the location of the core FVM09 epitope (yellow circles) within a disordered loop connecting β17 and β18 within GP structure (GenBank PDB: 3CSY). FIG. 7C shows the sequence identity of FVM09 epitope and surrounding regions among ebolavirus species (SEQ ID NOS 430-434, respectively, in order of appearance). FIG. 7D shows the sequence of the five overlapping peptides (Top) surrounding the core sequence (boxed) that showed competition with FVM02p binding in ELISA (bottom) (SEQ ID NOS 425-429, respectively, in order of appearance). FIG. 7E shows the position of the core FVM02p epitope within GP fusion loop (PDB: 3CSY). The body of the fusion loop is shown in yellow with its tip containing FVM02p epitope in red. FIG. 7F shows the sequence identity of the FVM02p epitope and surrounding regions among ebolavirus species as well as RAVV and MARV strains (SEQ ID NOS 435-444, respectively, in order of appearance).

Figure 8A:
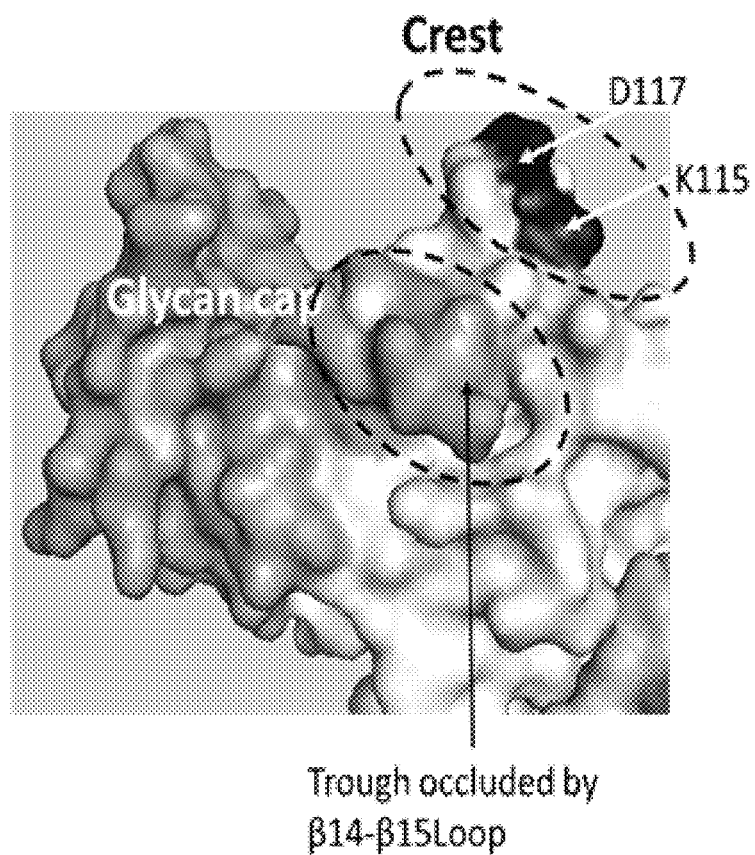
Figure 8B:
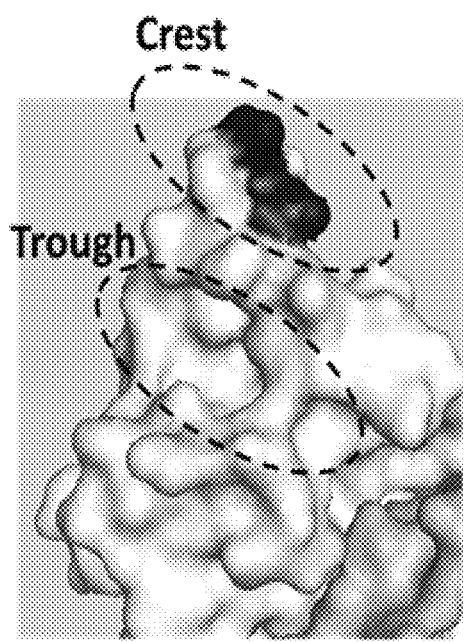
Figure 8C:
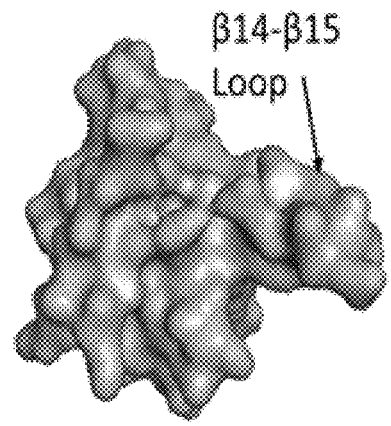

FIG. 8A-C: Structure of EBOV GP putative receptor binding site (RBS). FIG. 8A shows the crest and trough morphology of the putative RBS. FVM04 binding sites are shown in black and glycan cap shown in dark gray. The β14-β15 loop packs against the trough in the full length GP (before cathepsin cleavage) thus occluding the RBS. In contrast the crest containing the FVM04 key contact sites is well exposed on the top of GP. FIG. 8B shows that the trough is exposed after removal of the glycan cap upon cathepsin cleavage. FIG. 8C shows the isolated glycan cap showing the β14-β15 loop.

Figures 9A, 9B:
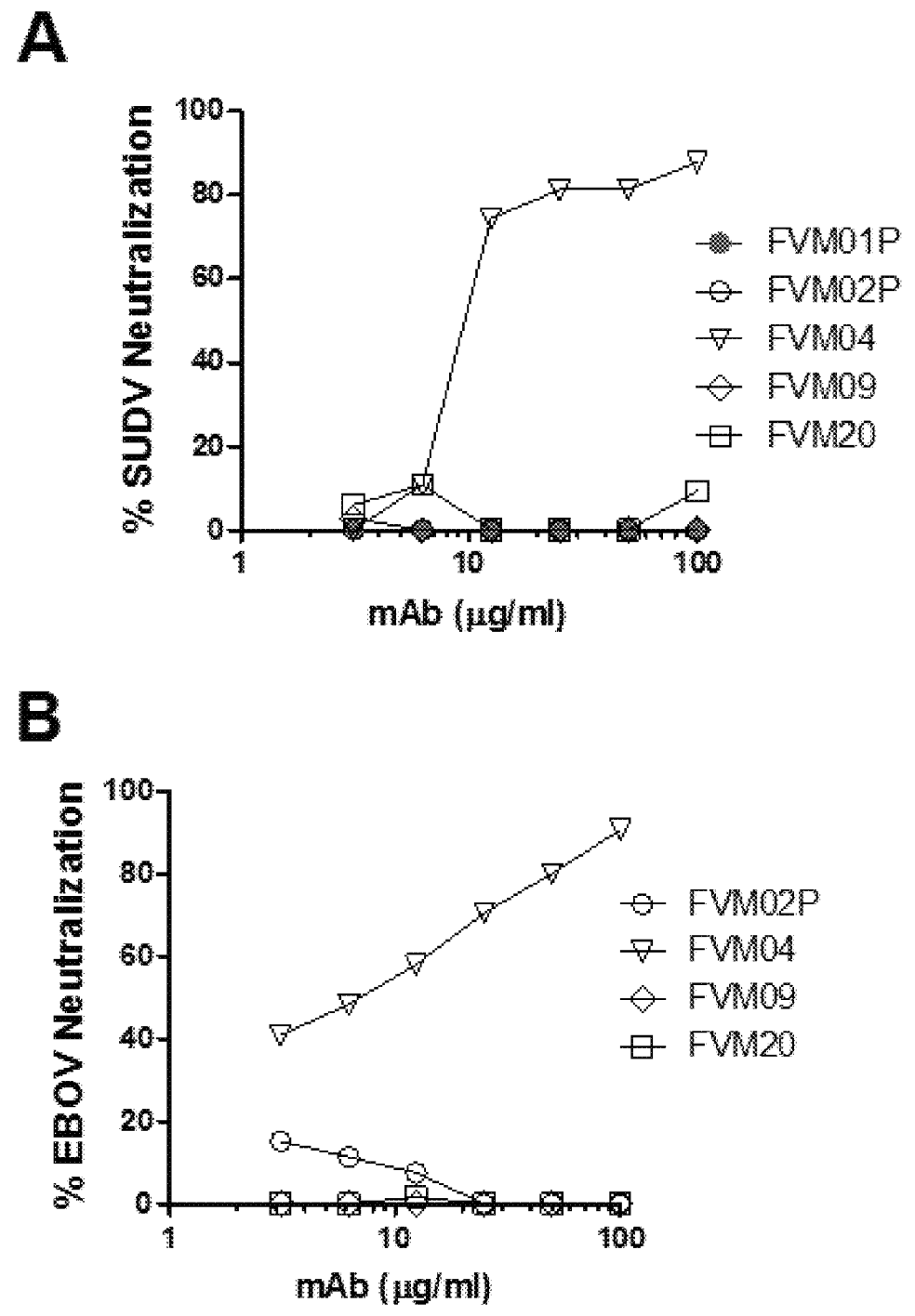

FIG. 9A-B: Neutralizing activity of the chimeric antibodies. The neutralizing activity of FVM04, FVM02p, FVM01p, FVM09, and FVM20 were determined for authentic SUDV (FIG. 9A) and EBOV (FIG. 9B) using a high content imaging assay.

Figure 10A:
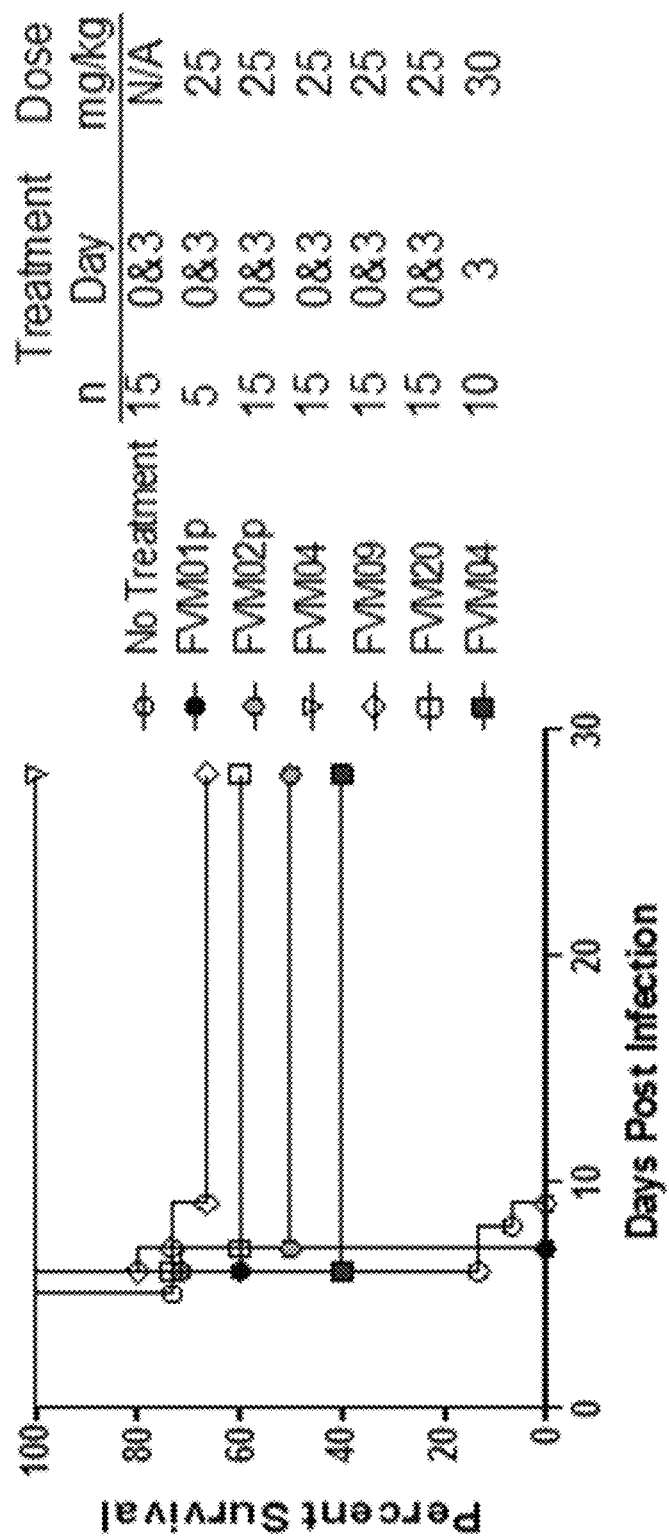
Figure 10B:
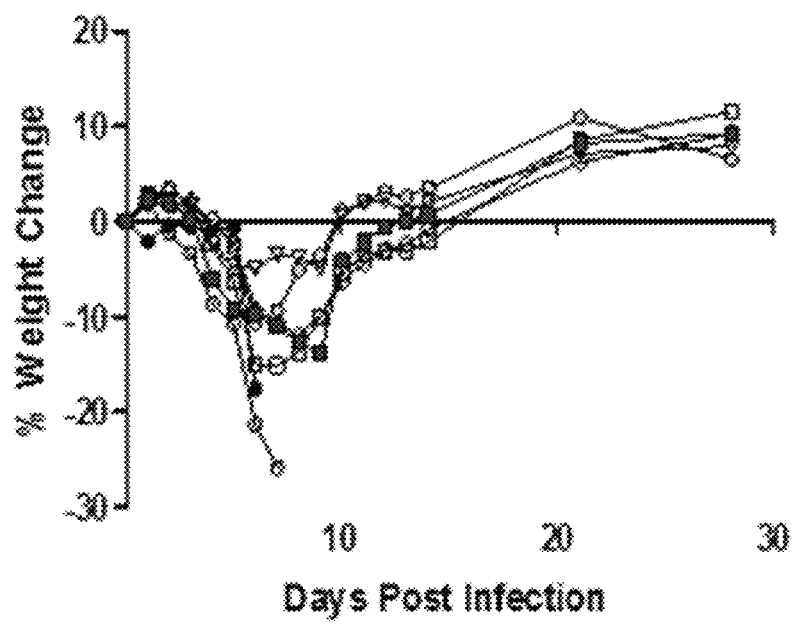

FIG. 10A-B: Efficacy of the macaque-human chimeric antibodies in mouse model of EBOV infection. Mice were infected with 1,000 PFU of MA-EBOV and treated either 2 hours after infection (day 0) and on day 3, or only once on day 3 post infection as indicated in the panels. FIG. 10A shows the protective efficacy of individual mAbs shown as percent survival. Statistical differences were assessed for each treatment group as compared to negative control group using Mantel-Cox (P=<0. 0.3536 for FVM01p, 0.0003 for FVM02p, <0.0001 for FVM04 (days 0&3), 0.0060 for FVM04 (day 3 only), and 0.0060 for FVM09 and FVM20). FIG. 10B shows the percent weight change (group average of surviving animals) after infection and treatment with individual animals from the study shown in FIG. 10A. The number of animals, antibody dose, and treatment regimen in each group is shown for each study.

Figure 11A:
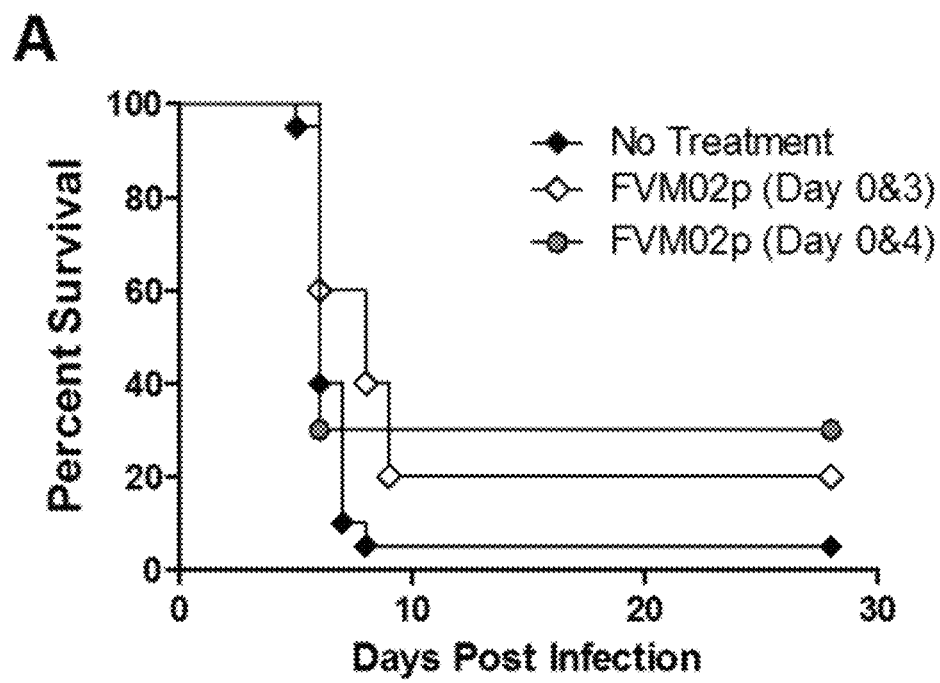
Figure 11B:
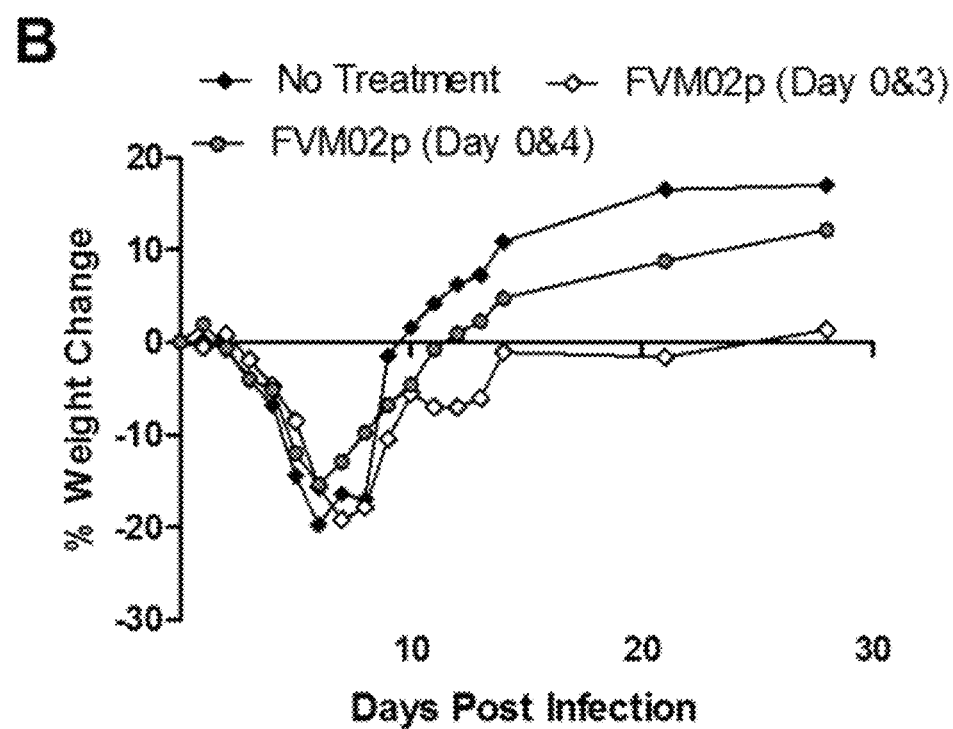

FIG. 11A-B: Efficacy of FVM02p in mouse model of MARV. Mice were infected with 1,000 PFU of MA-MARV and treated either 2 hours after infection (day 0) and on day 3, or at 2 hours and 3 days as indicated in the panels. FIG. 11A shows the percent survival of challenged mice. FIG. 11B shows the percent weight change (group average of surviving animals) after infection and treatment with individual animals from the study shown in FIG. 11A.

DETAILED DESCRIPTION

Definitions

The term "a" or "an" entity refers to one or more of that entity; for example, "polypeptide subunit" is understood to represent one or more polypeptide subunits. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-standard amino acids. A polypeptide can be derived from a natural biological source or produced by recombinant technology, but is not necessarily translated from a designated nucleic acid sequence. It can be generated in any manner, including by chemical synthesis.

A "protein" as used herein can refer to a single polypeptide, i.e., a single amino acid chain as defined above, but can also refer to two or more polypeptides that are associated, e.g., by disulfide bonds, hydrogen bonds, or hydrophobic interactions, to produce a multimeric protein.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are recombinant polypeptides that have been separated, fractionated, or partially or substantially purified by any suitable technique.

As used herein, the term "non-naturally occurring" polypeptide, or any grammatical variants thereof, is a conditional term that explicitly excludes, but only excludes, those forms of the polypeptide that are well-understood by persons of ordinary skill in the art as being "naturally-occurring," or that are, or might be at any time, determined or interpreted by a judge or an administrative or judicial body to be, "naturally-occurring."

Other polypeptides disclosed herein are fragments, derivatives, analogs, or variants of the foregoing polypeptides, and any combination thereof. The terms "fragment," "variant," "derivative" and "analog" when referring to polypeptide subunit or multimeric protein as disclosed herein can include any polypeptide or protein that retain at least some of the activities of the complete polypeptide or protein, but which is structurally different. Fragments of polypeptides include, for example, proteolytic fragments, as well as deletion fragments. Variants include fragments as described above, and also polypeptides with altered amino acid sequences due to amino acid substitutions, deletions, or insertions. Variants can occur spontaneously or be intentionally constructed. Intentionally constructed variants can be produced using art-known mutagenesis techniques. Variant polypeptides can comprise conservative or non-conservative amino acid substitutions, deletions or additions. Derivatives are polypeptides that have been altered so as to exhibit additional features not found on the native polypeptide. Examples include fusion proteins. Variant polypeptides can also be referred to herein as "polypeptide analogs." As used herein a "derivative" refers to a subject polypeptide having one or more amino acids chemically derivatized by reaction of a functional side group. Also included as "derivatives" are those peptides that contain one or more standard or synthetic amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Methods of identifying nucleotide and amino acid conservative substitutions which do not eliminate protein activity are well-known in the art (see, e.g., Brummell et al., *Biochem.* 32: 1180-1 187 (1993); Kobayashi et al., *Protein Eng.* 12(10):879-884 (1999); and Burks et al., *Proc. Natl. Acad. Sci. USA* 94:412-417 (1997)).

Disclosed herein are certain binding molecules, or antigen-binding fragments, variants, or derivatives thereof. Unless specifically referring to full-sized antibodies such as naturally-occurring antibodies, the term "binding molecule" encompasses full-sized antibodies as well as antigen-binding fragments, variants, analogs, or derivatives of such antibodies, e.g., naturally-occurring antibody or immunoglobulin molecules or engineered antibody molecules or fragments that bind antigen in a manner similar to antibody molecules.

As used herein, the term "binding molecule" refers in its broadest sense to a molecule that specifically binds an antigenic determinant. As described further herein, a binding molecule can comprise one of more "binding domains." As used herein, a "binding domain" is a two- or three-dimensional polypeptide structure that cans specifically bind a given antigenic determinant, or epitope. A non-limiting example of a binding molecule is an antibody or fragment thereof that comprises a binding domain that specifically binds an antigenic determinant or epitope. Another example of a binding molecule is a bispecific antibody comprising a first binding domain binding to a first epitope, and a second binding domain binding to a second epitope.

The terms "antibody" and "immunoglobulin" can be used interchangeably herein. An antibody (or a fragment, variant, or derivative thereof as disclosed herein comprises at least the variable domain of a heavy chain and at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma1$-$\gamma4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the binding molecule to selectively recognize and specifically bind epitopes on antigens. That is, the VL domain and VH domain, or subset of the complementarity determining regions (CDRs), of a binding molecule, e.g., an antibody combine to form the variable region that defines a three dimensional antigen binding site. This quaternary binding molecule structure forms the antigen-binding site present at the end of each arm of the Y. More specifically, the antigen-binding site is defined by three CDRs on each of the VH and VL chains.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, *J. Mol. Biol.*, 196:901-917 (1987), which are incorporated herein by reference in their entireties).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196: 901-917 (1987), which are incorporated herein by reference, where the definitions include overlapping or subsets of amino acids when compared against each other. Nevertheless, application of either definition to refer to a CDR of an antibody or variants thereof is intended to be within the scope of the term as defined and used herein. The appropriate amino acids that encompass the CDRs as defined by each of the above-cited references are set forth below in Table 1 as a comparison. The exact amino acid numbers which encompass a particular CDR will vary depending on the sequence and size of the CDR. Those skilled in the art can routinely determine which amino acids comprise a particular CDR given the variable region amino acid sequence of the antibody.

TABLE 1

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Immunoglobulin variable domains can also be analyzed using the IMGT information system (www://imgt.cines.fr/) (IMGT®/V-Quest) to identify variable region segments, including CDRs. See, e.g., Brochet, X. et al., *Nucl. Acids Res.* 36:W503-508 (2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

Binding molecules, e.g., antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen-binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

This disclosure provides binding molecules derived from non-human primate (NHP) antibody binding domains. A "NHP-derived" binding molecule, e.g., an antibody or antigen-binding fragment thereof, can include any portion of a NHP antibody binding domain, e.g., a single CDR, three CDRs, six CDRs, a VH, a VL, or any combination thereof derived from a NHP antibody, e.g., an antibody produced by B cells of a NHP, e.g., a macaque e.g., a rhesus macaque (*Macaca mulatta*), or a cynomolgus macaque (*Macaca fascicularis*).

A NHP-derived binding molecule, e.g., an antibody or fragment, variant, or derivative thereof disclosed herein can be said to bind a target antigen, e.g., a filovirus glycoprotein subunit disclosed herein or a fragment or variant thereof with an off rate (k(off)) of less than or equal to $5\times10^{-2}$ $sec^{-1}$, $10^{-2}$ $sec^{-1}$, $5\times10^{-3}$ $sec^{-1}$ or $10^{-3}$ sec. A NHP-derived binding molecule as disclosed herein can be said to bind a target antigen, e.g., a filovirus glycoprotein subunit, with an off rate (k(off)) less than or equal to $5\times10^{-4}$ $sec^{-1}$, $10^{-4}$ $sec^{-1}$, $5\times10^{-5}$ $sec^{-1}$, or $10^{-5}$ $sec^{-1}$ $5\times10^{-6}$ $sec^{-1}$, $10^{-6}$ $sec^{-1}$, $5\times10^{-7}$ $sec^{-1}$ or $10^{-7}$ $sec^{-1}$.

A NHP-derived binding molecule, e.g., an antibody or antigen-binding fragment, variant, or derivative disclosed herein can be said to bind a target antigen, e.g., a filovirus glycoprotein subunit with an on rate (k(on)) of greater than or equal to $10^3$ $M^{-1}$ $sec^{-1}$, $5\times10^3$ $M^{-1}$ $sec^{-1}$, $10^4$ $M^{-1}$ $sec^{-1}$ or $5\times10^4$ $M^{-1}$ $sec^{-1}$. A NHP-derived binding molecule as disclosed herein can be said to bind a target antigen, e.g., a filovirus glycoprotein subunit with an on rate (k(on)) greater than or equal to $10^5$ $M^{-1}$ $sec^{-1}$, $5\times10^5$ $M^{-1}$ $sec^{-1}$, $10^6$ $M^{-1}$ $sec^{-1}$, or $5\times10^6$ $M^{-1}$ $sec^{-1}$ or $10^7$ $M^{-1}$ $sec^{-1}$.

A NHP-derived binding molecule, e.g., an antibody or fragment, variant, or derivative thereof can be said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A NHP-derived binding molecule can be said to competitively inhibit binding of the reference antibody or antigen-binding fragment to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. An interaction between a between a bivalent monoclonal antibody with a receptor present at a high density on a cell surface would also be of high avidity.

Binding molecules or antigen-binding fragments, variants or derivatives thereof as disclosed herein can also be described or specified in terms of their cross-reactivity. As used herein, the term "cross-reactivity" refers to the ability of a NHP-derived binding molecule, e.g., an antibody or fragment, variant, or derivative thereof, specific for one antigen, to react with a second antigen; a measure of relatedness between two different antigenic substances. Thus, a binding molecule is cross-reactive if it binds to an epitope other than the one that induced its formation, e.g., various different filovirus receptor binding regions. The cross-reactive epitope contains many of the same complementary structural features as the inducing epitope, and in some cases, can actually fit better than the original.

A NHP-derived binding molecule, e.g., an antibody or fragment, variant, or derivative thereof can also be described or specified in terms of their binding affinity to an antigen. For example, a binding molecule can bind to an antigen with a dissociation constant or $K_D$ no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

Antibody fragments including single-chain antibodies can comprise the variable region(s) alone or in combination with the entirety or a portion of the following: hinge region, CH1, CH2, and CH3 domains. Also included are antigen-binding fragments that comprise any combination of variable region(s) with a hinge region, CH1, CH2, and CH3 domains. Binding molecules, e.g., antibodies, or antigen-binding fragments thereof disclosed herein can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain, a NHP-derived binding molecule, e.g., an antibody comprising a heavy chain portion comprises at least one of: a CH1 domain, a hinge (e.g., upper, middle, and/or lower hinge region) domain, a CH2 domain, a CH3 domain, or a variant or fragment thereof. For example, a NHP-derived binding molecule, e.g., an antibody or fragment, variant, or derivative thereof can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a NHP-derived binding molecule, e.g., an antibody or fragment, variant, or derivative thereof comprises a polypeptide chain comprising a CH3 domain. Further, a NHP-derived binding molecule for use in the disclosure can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

The heavy chain portions of a NHP-derived binding molecule, e.g., an antibody as disclosed herein can be derived from different immunoglobulin molecules. For example, a heavy chain portion of a polypeptide can comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. The light chain portion comprises at least one of a VL or CL domain.

NHP-derived binding molecules, e.g., antibodies or antigen-binding fragments, variants, or derivatives thereof disclosed herein can be described or specified in terms of the epitope(s) or portion(s) of an antigen, e.g., a target a filovirus glycoprotein subunit that they recognize or specifically bind. The portion of a target antigen that specifically interacts with the antigen-binding domain of an antibody is an "epitope," or an "antigenic determinant." A target antigen, e.g., a filovirus glycoprotein subunit can comprise a single epitope, but typically comprises at least two epitopes, and can include any number of epitopes, depending on the size, conformation, and type of antigen. As used herein, an "orthologous epitope" refers to versions of an epitope found in related organisms, e.g., different filovirus species or strains. Orthologous epitopes can be similar in structure, but can vary in one or more amino acids.

As previously indicated, the subunit structures and three-dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about amino acid 244 to amino acid 360 of an antibody using conventional numbering schemes (amino acids 244 to 360, Kabat numbering system; and amino acids 231-340, EU numbering system; see Kabat E A et al. op. cit. The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 amino acids.

As used herein, the term "hinge region" includes the portion of a heavy chain molecule that joins the CH1 domain to the CH2 domain. This hinge region comprises approximately 25 amino acids and is flexible, thus allowing the two N-terminal antigen-binding regions to move independently. Hinge regions can be subdivided into three distinct domains: upper, middle, and lower hinge domains (Roux et al., *J. Immunol.* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The term "bispecific antibody" as used herein refers to an antibody that has binding sites for two different antigens within a single antibody molecule. It will be appreciated that other molecules in addition to the canonical antibody structure can be constructed with two binding specificities. It will further be appreciated that antigen binding by bispecific antibodies can be simultaneous or sequential. Triomas and hybrid hybridomas are two examples of cell lines that can secrete bispecific antibodies. Bispecific antibodies can also be constructed by recombinant means. (Strohlein and Heiss, *Future Oncol.* 6:1387-94 (2010); Mabry and Snavely, *IDrugs.* 13:543-9 (2010)). A bispecific antibody can also be a diabody.

As used herein, the term "engineered antibody" refers to an antibody in which the variable domain in either the heavy and light chain or both is altered by at least partial replacement of one or more CDRs from an antibody of known specificity and, by partial framework region replacement and sequence changing. Although the CDRs can be derived from an antibody of the same class or even subclass as the antibody from which the framework regions are derived, it is envisaged that the CDRs will be derived from an antibody of different class, e.g., from an antibody from a different species. An engineered antibody in which one or more "donor" CDRs from a non-human antibody of known specificity is grafted into a human heavy or light chain framework region is referred to herein as a "humanized antibody." In some instances, not all of the CDRs are replaced with the complete CDRs from the donor variable region to transfer the antigen binding capacity of one variable domain to another; instead, minimal amino acids that maintain the activity of the target-binding site are transferred. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a polypeptide subunit contained in a vector is considered isolated as disclosed herein. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "non-naturally occurring" polynucleotide, or any grammatical variants thereof, is a conditional definition that explicitly excludes, but only excludes, those forms of the polynucleotide that are well-understood by persons of ordinary skill in the art as being "naturally-occurring," or that are, or that might be at any time, determined or interpreted by a judge or an administrative or judicial body to be, "naturally-occurring."

As used herein, a "coding region" is a portion of nucleic acid comprising codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can encode heterologous coding regions, either fused or unfused to a nucleic acid encoding a polypeptide subunit or fusion protein as provided herein. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association or linkage can be when a coding region for a gene product, e.g., a polypeptide, can be associated with one or more regulatory sequences in such a way as to place expression of the gene product under the influence or control of the regulatory sequence(s). Two DNA fragments (such as a polypeptide coding region and a promoter associated therewith) can be "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA).

Polynucleotide and nucleic acid coding regions can be associated with additional coding regions that encode secretory or signal peptides, which direct the secretion of a polypeptide encoded by a polynucleotide as disclosed herein, e.g., a polynucleotide encoding a polypeptide subunit provided herein. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse β-glucuronidase.

A "vector" is nucleic acid molecule as introduced into a host cell, thereby producing a transformed host cell. A vector can include nucleic acid sequences that permit it to replicate in a host cell, such as an origin of replication. A vector can also include one or more selectable marker gene and other genetic elements known in the art.

A "transformed" cell, or a "host" cell, is a cell into which a nucleic acid molecule has been introduced by molecular biology techniques. As used herein, the term transformation encompasses those techniques by which a nucleic acid molecule can be introduced into such a cell, including transfection with viral vectors, transformation with plasmid vectors, and introduction of naked DNA by electroporation, lipofection, and particle gun acceleration. A transformed cell or a host cell can be a bacterial cell or a eukaryotic cell.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein the terms "treat," "treatment," or "treatment of" (e.g., in the phrase "treating a subject") refers to reducing the potential for disease pathology, reducing the occurrence of disease symptoms, e.g., to an extent that the subject has a longer survival rate or reduced discomfort. For example, treating can refer to the ability of a therapy when administered to a subject, to reduce disease symptoms, signs, or causes. Treating also refers to mitigating or decreasing at least one clinical symptom and/or inhibition or delay in the progression of the condition and/or prevention or delay of the onset of a disease or illness.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals, including, e.g., humans, non-human primates, dogs, cats, guinea pigs, rabbits, rats, mice, horses, cattle, bears, and so on.

The term "pharmaceutical composition" refers to a preparation that is in such form as to permit the biological activity of the active ingredient to be effective, and that contains no additional components that are unacceptably toxic to a subject to which the composition would be administered. Such composition can be sterile.

An "effective amount" of an antibody as disclosed herein is an amount sufficient to carry out a specifically stated purpose. An "effective amount" can be determined empirically and in a routine manner, in relation to the stated purpose.

NHP-Derived Pan-Filovirus Binding Molecules

This disclosure provides a NHP-derived pan-filovirus binding molecule, e.g., a cross-reactive anti-filovirus antibody or antigen-binding fragment thereof containing at least a portion of a non-human primate antibody, e.g., at least one CDR, at least three CDRs, at least six CDRs, at least a VH, at least a VL, or at least a VH and a VL from a macaque, e.g., a rhesus macaque (*Macaca mulatta*). NHP-derived pan-filovirus binding molecules can be useful for treatment of a filovirus infection without it being necessary to know the exact filovirus species or strain. More specifically, the disclosure provides an isolated NHP-derived binding molecule or antigen-binding fragment thereof comprising a binding domain that specifically binds to an orthologous filovirus glycoprotein epitope, wherein the binding domain specifically binds to the epitope on two, three, four, five, or more filovirus species or strains. In certain aspects the NHP-derived pan-filovirus binding molecule can be a cross-reactive antibody or antigen-binding fragment thereof. In certain aspects the binding molecule can be a bispecific antibody that can facilitate targeting of the binding molecule to the endosomal region of a filovirus-infected cell, e.g., through a second binding domain. See, e.g., Provisional Patent Appl. Ser. No. 62/019,668, filed, Jul. 1, 2014, which is incorporated herein by reference in its entirety.

In certain aspects, the binding domain of a NHP-derived pan-filovirus binding molecule, e.g., a cross-reactive anti-filovirus antibody or antigen-binding fragment thereof can specifically bind to a filovirus orthologous epitope as expressed in one or more, two or more, three or more, four or more, or five or more filovirus species including, Marburg virus (MARV), Ravn virus (RAVV), Tai Forest virus (TAFV), Reston virus (RESTV), Sudan virus (SUDV), Ebola virus (EBOV), and Bundibugyo virus (BDBV). For example, the binding domain of a NHP-derived pan-filovirus binding molecule, e.g., a cross-reactive anti-filovirus antibody or antigen-binding fragment thereof can bind to an orthologous filovirus epitope as expressed in one or more, two or more, or three of EBOV, SUDV, and MARV. In certain aspects, the binding domain of a NHP-derived pan-filovirus binding molecule, e.g., a cross-reactive anti-filovirus antibody or antigen-binding fragment thereof can bind to an orthologous filovirus epitope as expressed in MARV. In certain aspects, the binding domain of a NHP-derived pan-filovirus binding molecule, e.g., a cross-reactive anti-filovirus antibody or antigen-binding fragment thereof can bind to an orthologous filovirus epitope as expressed in EBOV and SUDV. Any filovirus epitope which has similarities across filovirus species can be a target of the binding domain of a NHP-derived pan-filovirus binding molecule as provided herein.

One exemplary binding domain can be derived from the VH and VL antigen binding domains of macaque monoclonal antibody FVM02P, which bind to surface glycoprotein of at least three different species of filovirus, e.g., the binding domain can bind to the orthologous epitope as expressed in EBOV, SUDV, and MARV. In certain aspects the binding domain of this exemplary NHP-derived pan-filovirus binding molecule or fragment thereof can bind to the same orthologous epitope as an antibody or antigen-binding fragment thereof comprising a heavy chain variable region (VH) and light chain variable region (VL) comprising, respectively, the amino acid sequences SEQ ID NO: 12 and 17 (the VH and VL of FVM02P). In certain aspects the binding domain of this exemplary NHP-derived pan-filovirus binding molecule or fragment thereof can competitively inhibit antigen binding by an antibody or antigen-binding fragment thereof comprising a heavy chain variable region (VH) and light chain variable region (VL) comprising, respectively, the amino acid sequences SEQ ID NO: 12 and 17.

Another exemplary binding domain can be derived from the VH and VL antigen binding domains of macaque monoclonal antibody FVM03, which can bind to at least the MARV surface glycoprotein. In certain aspects the binding domain of this exemplary NHP-derived pan-filovirus binding molecule or fragment thereof can bind to the same orthologous epitope as an antibody or antigen-binding fragment thereof comprising a heavy chain variable region (VH) and light chain variable region (VL) comprising, respectively, the amino acid sequences SEQ ID NO: 22 and 27 (the VH and VL of FVM03). In certain aspects the binding domain of this exemplary NHP-derived pan-filovirus binding molecule or fragment thereof can competitively inhibit antigen binding by an antibody or antigen-binding fragment thereof comprising a heavy chain variable region (VH) and light chain variable region (VL) comprising, respectively, the amino acid sequences SEQ ID NO: 22 and 27.

Another exemplary binding domain can be derived from the VH and VL antigen binding domains of one or more of macaque monoclonal antibodies FVM01P, FVM04, FVM05, FVM06, FVM07, FVM08, FVM09, FVM10, FVM11, FVM12, FVM13, FVM14, FVM15, FVM16, FVM17, FVM18, FVM19, FVM20, FVM21, FVM22, FVM23, FVM24, FVM25, FVM26, FVM27, FVM28, FVM29, FVM31, FVM32, FVM33, FVM34, FVM35, FVM36, FVM37, FVM38, FVM39, FVM40, FVM41, or FVM42, each of which can bind to the filovirus glycoprotein across at least two species of filovirus, e.g., the binding domain can bind to the orthologous epitope as expressed in EBOV and SUDV. In certain aspects the binding domains of one or more of these exemplary NHP-derived pan-filovirus binding molecules or fragments thereof can bind to the same orthologous epitope as an antibody or antigen-binding fragment thereof comprising a heavy chain variable region (VH) and light chain variable region (VL) comprising, respectively, the amino acid sequences SEQ ID NO: 2 and SEQ ID NO: 7; SEQ ID NO: 32 and SEQ ID NO: 37; SEQ ID NO: 42 and SEQ ID NO: 47; SEQ ID NO: 52 and SEQ ID NO: 57; SEQ ID NO: 62 and SEQ ID NO: 67; SEQ ID NO: 72 and SEQ ID NO: 57; SEQ ID NO: 82 and SEQ ID NO: 87; SEQ ID NO: 92 and SEQ ID NO: 97; SEQ ID NO: 82 and SEQ ID NO: 107; SEQ ID NO: 112 and SEQ ID NO: 117; SEQ ID NO: 122 and SEQ ID NO: 127; SEQ ID NO: 132 and SEQ ID NO: 137; SEQ ID NO: 142 and SEQ ID NO: 57; SEQ ID NO: 152 and SEQ ID NO: 157; SEQ ID NO: 162 and SEQ ID NO: 167; SEQ ID NO: 172 and SEQ ID NO: 177; SEQ ID NO: 182 and SEQ ID NO: 187; SEQ ID NO: 192 and SEQ ID NO: 197; SEQ ID NO: 202 and SEQ ID NO: 207; SEQ ID NO: 212 and SEQ ID NO: 217; SEQ ID NO: 222 and SEQ ID NO: 227; SEQ ID NO: 232 and SEQ ID NO: 237; SEQ ID NO: 242 and SEQ ID NO: 247; SEQ ID NO: 142 and SEQ ID NO: 57; SEQ ID NO: 262 and SEQ ID NO: 267; SEQ ID NO: 272 and SEQ ID NO: 277; SEQ ID NO: 282 and SEQ ID NO: 57; SEQ ID NO: 292 and SEQ ID NO: 297; SEQ ID NO: 302 and SEQ ID NO: 307; SEQ ID NO: 312 and SEQ ID NO: 57; SEQ ID NO: 322 and SEQ ID NO: 327; SEQ ID NO: 332 and SEQ ID NO: 57; SEQ ID NO: 342 and SEQ ID NO: 347; SEQ ID NO: 352 and SEQ ID NO: 357; SEQ ID NO: 362 and SEQ ID NO: 57; SEQ ID NO: 372 and SEQ ID NO: 57; SEQ ID NO: 382 and SEQ ID NO: 387; SEQ ID NO: 392 and SEQ ID NO: 397; or SEQ ID NO: 402 and SEQ ID NO: 407 (the respective VHs and VLs of FVM01P, FVM04, FVM05, FVM06, FVM07, FVM08, FVM09, FVM10, FVM11, FVM12, FVM13, FVM14, FVM15, FVM16, FVM17, FVM18, FVM19, FVM20, FVM21, FVM22, FVM23, FVM24, FVM25, FVM26, FVM27, FVM28, FVM29, FVM31, FVM32, FVM33, FVM34, FVM35, FVM36, FVM37, FVM38, FVM39, FVM40, FVM41, and FVM42). In certain aspects the binding domain of this exemplary NHP-derived pan-filovirus binding molecule or fragment thereof can competitively inhibit antigen binding by an antibody or antigen-binding fragment thereof comprising a heavy chain variable region (VH) and light chain variable region (VL) comprising, respectively, the amino acid sequences SEQ ID NO: 2 and SEQ ID NO: 7; SEQ ID NO: 32 and SEQ ID NO: 37; SEQ ID NO: 42 and SEQ ID NO: 47; SEQ ID NO: 52 and SEQ ID NO: 57; SEQ ID NO: 62 and SEQ ID NO: 67; SEQ ID NO: 72 and SEQ ID NO: 57; SEQ ID NO: 82 and SEQ ID NO: 87; SEQ ID NO: 92 and SEQ ID NO: 97; SEQ ID NO: 82 and SEQ ID NO: 107; SEQ ID NO: 112 and SEQ ID NO: 117; SEQ ID NO: 122 and SEQ ID NO: 127; SEQ ID NO: 132 and SEQ ID NO: 137; SEQ ID NO: 142 and SEQ ID NO: 57; SEQ ID NO: 152 and SEQ ID NO: 157; SEQ ID NO: 162 and SEQ ID NO: 167; SEQ ID NO: 172 and SEQ ID NO: 177; SEQ ID NO: 182 and SEQ ID NO: 187; SEQ ID NO: 192 and SEQ ID NO: 197; SEQ ID NO: 202 and SEQ ID NO: 207; SEQ ID NO: 212 and SEQ ID NO: 217; SEQ ID NO: 222 and SEQ ID NO: 227; SEQ ID NO: 232 and SEQ ID NO: 237; SEQ ID NO: 242 and SEQ ID NO: 247; SEQ ID NO: 142 and SEQ ID NO: 57; SEQ ID NO: 262 and SEQ ID NO: 267; SEQ ID NO: 272 and SEQ ID NO: 277; SEQ ID NO: 282 and SEQ ID NO: 57; SEQ ID NO: 292 and SEQ ID NO: 297; SEQ ID NO: 302 and SEQ ID NO: 307; SEQ ID NO: 312 and SEQ ID NO: 57; SEQ ID NO: 322 and SEQ ID NO: 327; SEQ ID NO: 332 and SEQ ID NO: 57; SEQ ID NO: 342 and SEQ ID NO: 347; SEQ ID NO: 352 and SEQ ID NO: 357; SEQ ID NO: 362 and SEQ ID NO: 57; SEQ ID NO: 372 and SEQ ID NO: 57; SEQ ID NO: 382 and SEQ ID NO: 387; SEQ ID NO: 392 and SEQ ID NO: 397; or SEQ ID NO: 402 and SEQ ID NO: 407.

In certain aspects a NHP-derived pan-filovirus binding molecule as provided herein can be an anti-filovirus antibody or antigen-binding fragment thereof. For example in certain aspects the disclosure provides a NHP-derived pan-filovirus antibody or antigen-binding fragment thereof comprising a binding domain that comprises VH-CDR1, VH-CDR2, VH-CDR3, VL-CDR1, VL-CDR2, and VL-CDR3 amino acid sequences identical or identical except for four, three, two, or one single amino acid substitutions, deletions, or insertions in one or more CDRs to: S SEQ ID NOs 3, 4, 5, 8, 9, and 10; SEQ ID NOs 13, 14, 15, 18, 19, and 20; SEQ ID NOs 23, 24, 25, 28, 29, and 30; SEQ ID NOs 33, 34, 35, 38, 39, and 40; SEQ ID NOs 43, 44, 45, 48, 49, and 50; SEQ ID NOs 53, 54, 55, 58, 59, and 60; SEQ ID NOs 63, 64, 65, 68, 69, and 70; SEQ ID NOs 73, 74, 75, 58, 59, and 60; SEQ ID NOs 73, 84, 55, 58, 59, and 60; SEQ ID NOs 73, 84, 95, 58, 69, and 60; SEQ ID NOs 73, 84, 55, 58, 59, and 60; SEQ ID NOs 113, 74, 55, 58, 119, and 120; SEQ ID NOs 123, 74, 55, 58, 59, and 60; SEQ ID NOs 133, 84, 55, 58, 59, and 60; SEQ ID NOs 143, 84, 55, 58, 59, and 60; SEQ ID NOs 153, 84, 55, 58, 59, and 120; SEQ ID NOs 163, 164, 55, 58, 119, and 60; SEQ ID NOs 173, 84, 55, 68, 179, and 180; SEQ ID NOs 73, 64, 55, 68, 69, and 190; SEQ ID NOs 193, 84, 55, 68, 179, and 60; SEQ ID NOs 73, 84, 75, 58, 69, and 60; SEQ ID NOs 73, 84, 95, 58, 59, and 60; SEQ ID NOs 193, 224, 55, 58, 59, and 230; SEQ ID NOs 73, 234, 55, 58, 59, and 60; SEQ ID NOs 143, 244, 55, 58, 119, and 120; SEQ ID NOs 143, 84, 55, 58, 59, and 60; SEQ ID NOs 263, 264, 55, 58, 59, and 60; SEQ ID NOs 273, 274, 55, 68, 179, and 180; SEQ ID NOs 283, 274, 55, 58, 59, and 60; SEQ ID NOs 73, 164, 55, 58, 59, and 60; SEQ ID NOs 73, 74, 55, 308, 59, and 60; SEQ ID NOs 313, 74, 55, 58, 59, and 60; SEQ ID NOs 323, 84, 55, 68, 69, and 120; SEQ ID NOs 333, 84, 55, 58, 59, and 60; SEQ ID NOs 343, 84, 55, 58, 59, and 60; SEQ ID NOs 123, 84, 55, 58, 59, and 60; SEQ ID NOs 63, 84, 55, 58, 59, and 60; SEQ ID NOs 163, 84, 55, 58, 59, and 60; SEQ ID NOs 163, 84, 55, 58, 59, and 60; SEQ ID NOs 393, 84, 55, 58, 59, and 60; or SEQ ID NOs 73, 404, 55, 58, 59, and 60; respectively.

Furthermore, in certain aspects the disclosure provides a NHP-derived pan-filovirus antibody or antigen-binding fragment thereof comprising a binding domain that comprises VH and VL amino acid sequences at least 85%, 90%, 95%, or 100% identical to reference amino acid sequences SEQ ID NO: 2 and SEQ ID NO: 7; SEQ ID NO: 12 and SEQ ID NO: 17; SEQ ID NO: 22 and SEQ ID NO: 27; SEQ ID NO: 32 and SEQ ID NO: 37; SEQ ID NO: 42 and SEQ ID NO: 47; SEQ ID NO: 52 and SEQ ID NO: 57; SEQ ID NO: 62 and SEQ ID NO: 67; SEQ ID NO: 72 and SEQ ID NO: 57; SEQ ID NO: 82 and SEQ ID NO: 87; SEQ ID NO: 92 and SEQ ID NO: 97; SEQ ID NO: 82 and SEQ ID NO: 107; SEQ ID NO: 112 and SEQ ID NO: 117; SEQ ID NO: 122 and SEQ ID NO: 127; SEQ ID NO: 132 and SEQ ID NO: 137; SEQ ID NO: 142 and SEQ ID NO: 57; SEQ ID NO: 152 and SEQ ID NO: 157; SEQ ID NO: 162 and SEQ ID NO: 167; SEQ ID NO: 172 and SEQ ID NO: 177; SEQ ID NO: 182 and SEQ ID NO: 187; SEQ ID NO: 192 and SEQ ID NO: 197; SEQ ID NO: 202 and SEQ ID NO: 207; SEQ ID NO: 212 and SEQ ID NO: 217; SEQ ID NO: 222 and SEQ ID NO: 227; SEQ ID NO: 232 and SEQ ID NO: 237; SEQ ID NO: 242 and SEQ ID NO: 247; SEQ ID NO: 142 and SEQ ID NO: 57; SEQ ID NO: 262 and SEQ ID NO: 267; SEQ ID NO: 272 and SEQ ID NO: 277; SEQ ID NO: 282 and SEQ ID NO: 57; SEQ ID NO: 292 and SEQ ID NO: 297; SEQ ID NO: 302 and SEQ ID NO: 307; SEQ ID NO: 312 and SEQ ID NO: 57; SEQ ID NO: 322 and SEQ ID NO: 327; SEQ ID NO: 332 and SEQ ID NO: 57; SEQ ID NO: 342 and SEQ ID NO: 347; SEQ ID NO: 352 and SEQ ID NO: 357; SEQ ID NO: 362 and SEQ ID NO: 57; SEQ ID NO: 372 and SEQ ID NO: 57; SEQ ID NO: 382 and SEQ ID NO: 387; SEQ ID NO: 392 and SEQ ID NO: 397; or SEQ ID NO: 402 and SEQ ID NO: 407; respectively.

A NHP-derived pan-filovirus antibody or antigen-binding fragment thereof as provided herein can be, for example, a NHP antibody, a humanized antibody, a chimeric antibody, or a fragment thereof. Moreover, the antibody or fragment thereof can be a monoclonal antibody, a component of a polyclonal antibody mixture, a recombinant antibody, a multispecific antibody, or any combination thereof.

In certain aspects, a NHP-derived pan-filovirus antibody or fragment thereof as provided herein can be a bispecific antibody or fragment thereof that further comprises a second binding domain. Certain bispecific antibodies as provided herein can be engineered to be targeted to the endosomal regions of a filovirus-infected cell. See, e.g., Provisional Patent Appl. Ser. No. 62/019,668, filed, Jul. 1, 2014, which is incorporated herein by reference in its entirety. For example, a NHP-derived bispecific antibody can comprise a second binding domain that specifically binds to a filovirus epitope that can be surface exposed and accessible to the second binding domain on a filovirus virion particle. In this aspect, the bispecific antibody can be targeted to the endosomal compartment of an infected cell, where cathepsin enzymes can cleave the mucin-like domain that masks the receptor binding region on native filovirus virion particles, thus opening the receptor-binding region up to a first binding domain which can then bind to the virus and neutralize the virus infectivity. In certain aspects, the second binding domain can bind to a surface exposed epitope on a virion particle, for example, the second binding domain can specifically bind to an epitope located in the mucin-like domain, an epitope located in the glycan cap, an epitope located in the GP2 fusion domain, or any combination thereof.

An antibody or fragment thereof of as provided herein can in certain aspects comprise a heavy chain constant region or fragment thereof. The heavy chain can be a murine constant region or fragment thereof, e.g., a human constant region or fragment thereof, e.g., IgM, IgG, IgA, IgE, IgD, or IgY constant region or fragment thereof. Various human IgG constant region subtypes or fragments thereof can also be included, e.g., a human IgG1, IgG2, IgG3, or IgG4 constant region or fragment thereof.

An antibody or fragment thereof as provided herein can further comprise a light chain constant region or fragment thereof. For example, the light chain constant region or fragment thereof can be a murine constant region or fragment thereof, e.g., a human light chain constant region or fragment thereof, e.g., a human kappa or lambda constant region or fragment thereof.

In certain aspects the binding domain of a NHP-derived pan-filovirus antibody or fragment thereof as provided herein comprises a full-size antibody comprising two heavy chains and two light chains. In other aspects, the binding domain of a NHP-derived pan-filovirus antibody or fragment thereof as provided herein comprises an Fv fragment, an Fab fragment, an F(ab')2 fragment, an Fab' fragment, a dsFv fragment, an scFv fragment, an scFab fragment, an sc(Fv)2 fragment, or any combination thereof.

In certain aspects the second binding domain of a NHP-derived pan-filovirus antibody or fragment thereof as provided herein comprises a full-size antibody comprising two heavy chains and two light chains. In other aspects, the second binding domain of a NHP-derived pan-filovirus antibody or fragment thereof as provided herein comprises an Fv fragment, an Fab fragment, an F(ab')2 fragment, an Fab' fragment, a dsFv fragment, an scFv fragment, an scFab fragment, an sc(Fv)2 fragment, or any combination thereof.

In certain aspects a NHP-derived pan-filovirus antibody or fragment thereof as provided herein fully or partially neutralizes infectivity of the filovirus upon binding of the binding domain to the orthologous epitope on a filovirus.

In certain aspects, a NHP-derived pan-filovirus antibody or fragment thereof as provided herein can be conjugated to an antiviral agent, a protein, a lipid, a detectable label, a polymer, or any combination thereof.

The disclosure further provides a composition comprising a NHP-derived pan-filovirus binding molecule, e.g., a cross-reactive anti-filovirus antibody or antigen-binding fragment thereof, and a carrier.

Polynucleotides

In certain aspects the disclosure provides an isolated polynucleotide comprising a nucleic acid encoding a NHP-derived pan-filovirus binding molecule, e.g., a cross-reactive anti-filovirus antibody or antigen-binding fragment thereof or a subunit thereof. For example, a polynucleotide as provided herein can include a nucleic acid encoding a VH, wherein the VH comprises VH-CDR1, VH-CDR2, and VH-CDR3, wherein the VH-CDRs comprise, respectively, amino acid sequences identical to, or identical except for four, three, two, or one single amino acid substitutions, deletions, or insertions in one or more of the VH-CDRs to: SEQ ID NOs 3, 4, and 5; SEQ ID NOs 13, 14, and 15; SEQ ID NOs 23, 24, and 25; SEQ ID NOs 33, 34, and 35; SEQ ID NOs 43, 44, and 45; SEQ ID NOs 53, 54, and 55; SEQ ID NOs 63, 64, and 65; SEQ ID NOs 73, 74, and 75; SEQ ID NOs 73, 84, and 55; SEQ ID NOs 73, 84, and 95; SEQ ID NOs 73, 84, and 55; SEQ ID NOs 113, 74, and 55; SEQ ID NOs 123, 74, and 55; SEQ ID NOs 133, 84, and 55; SEQ ID NOs 143, 84, and 55; SEQ ID NOs 153, 84, and 55; SEQ ID NOs 163, 164, and 55; SEQ ID NOs 173, 84, and 55;

SEQ ID NOs 73, 64, and 55; SEQ ID NOs 193, 84, and 55; SEQ ID NOs 73, 84, and 75; SEQ ID NOs 73, 84, and 95; SEQ ID NOs 193, 224, and 55; SEQ ID NOs 73, 234, and 55; SEQ ID NOs 143, 244, and 55; SEQ ID NOs 143, 84, and 55; SEQ ID NOs 263, 264, and 55; SEQ ID NOs 273, 274, and 55; SEQ ID NOs 283, 274, and 55; SEQ ID NOs 73, 164, and 55; SEQ ID NOs 73, 74, and 55; SEQ ID NOs 313, 74, and 55; SEQ ID NOs 323, 84, and 55; SEQ ID NOs 333, 84, and 55; SEQ ID NOs 343, 84, and 55; SEQ ID NOs 123, 84, and 55; SEQ ID NOs 63, 84, and 55; SEQ ID NOs 163, 84, and 55; SEQ ID NOs 163, 84, and 55; SEQ ID NOs 393, 84, and 55; or SEQ ID NOs 73, 404, and 55.

Moreover, a polynucleotide as provided herein can include a nucleic acid encoding a VL that includes a VL-CDR1, a VL-CDR2, and a VL-CDR3, wherein the VL-CDRs comprise, respectively, amino acid sequences identical to, or identical except for four, three, two, or one single amino acid substitutions, deletions, or insertions in one or more of the VL-CDRs to: SEQ ID NOs 8, 9, and 10; SEQ ID NOs 18, 19, and 20; SEQ ID NOs 28, 29, and 30; SEQ ID NOs 38, 39, and 40; SEQ ID NOs 48, 49, and 50; SEQ ID NOs 58, 59, and 60; SEQ ID NOs 68, 69, and 70; SEQ ID NOs 58, 59, and 60; SEQ ID NOs 58, 59, and 60; SEQ ID NOs 58, 69, and 60; SEQ ID NOs 58, 59, and 60; SEQ ID NOs 58, 119, and 120; SEQ ID NOs 58, 59, and 60; SEQ ID NOs 58, 59, and 60; SEQ ID NOs 58, 59, and 60; SEQ ID NOs 58, 59, and 120; SEQ ID NOs 58, 119, and 60; SEQ ID NOs 68, 179, and 180; SEQ ID NOs 68, 69, and 190; SEQ ID NOs 68, 179, and 60; SEQ ID NOs 58, 69, and 60; SEQ ID NOs 58, 59, and 60; SEQ ID NOs 58, 59, and 230; SEQ ID NOs 58, 59, and 60; SEQ ID NOs 58, 119, and 120; SEQ ID NOs 58, 59, and 60; SEQ ID NOs 58, 59, and 60; SEQ ID NOs 68, 179, and 180; SEQ ID NOs 58, 59, and 60; SEQ ID NOs 58, 59, and 60; SEQ ID NOs 308, 59, and 60; SEQ ID NOs 58, 59, and 60; SEQ ID NOs 68, 69, and 120; SEQ ID NOs 58, 59, and 60; SEQ ID NOs 58, 59, and 60; SEQ ID NOs 58, 59, and 60; SEQ ID NOs 58, 59, and 60; SEQ ID NOs 58, 59, and 60; SEQ ID NOs 58, 59, and 60; SEQ ID NOs 58, 59, and 60; SEQ ID NOs 58, 59, and 60.

In certain aspects, a polynucleotide as provided herein an include a nucleic acid encoding a VH that comprises an amino acid sequence at least 85%, 90%, 95%, or 100% identical to the reference amino acid sequence SEQ ID NO: 2, SEQ ID NO: 12, SEQ ID NO: 22, SEQ ID NO: 32, SEQ ID NO: 42, SEQ ID NO: 52, SEQ ID NO: 62, SEQ ID NO: 72, SEQ ID NO: 82, SEQ ID NO: 92, SEQ ID NO: 112, SEQ ID NO: 122, SEQ ID NO: 132, SEQ ID NO: 142, SEQ ID NO: 152, SEQ ID NO: 162, SEQ ID NO: 172, SEQ ID NO: 182, SEQ ID NO: 192, SEQ ID NO: 202, SEQ ID NO: 212, SEQ ID NO: 222, SEQ ID NO: 232, SEQ ID NO: 242, SEQ ID NO: 262, SEQ ID NO: 272, SEQ ID NO: 282, SEQ ID NO: 292, SEQ ID NO: 302, SEQ ID NO: 312, SEQ ID NO: 322, SEQ ID NO: 332, SEQ ID NO: 342, SEQ ID NO: 352, SEQ ID NO: 362, SEQ ID NO: 372, SEQ ID NO: 382, SEQ ID NO: 392, or SEQ ID NO: 402. In certain aspects, a polynucleotide as provided herein an include a nucleic acid encoding a VL, wherein the VL comprises an amino acid sequence at least 85%, 90%, 95%, or 100% identical to the reference amino acid sequence SEQ ID NO: 7, SEQ ID NO: 17, SEQ ID NO: 27, SEQ ID NO: 37, SEQ ID NO: 47, SEQ ID NO: 57, SEQ ID NO: 67, SEQ ID NO: 87, SEQ ID NO: 97, SEQ ID NO: 107, SEQ ID NO: 117, SEQ ID NO: 127, SEQ ID NO: 137, SEQ ID NO: 157, SEQ ID NO: 167, SEQ ID NO: 177, SEQ ID NO: 187, SEQ ID NO: 197, SEQ ID NO: 207, SEQ ID NO: 217, SEQ ID NO: 227, SEQ ID NO: 237, SEQ ID NO: 247, SEQ ID NO: 267, SEQ ID NO: 277, SEQ ID NO: 297, SEQ ID NO: 307, SEQ ID NO: 327, SEQ ID NO: 347, SEQ ID NO: 357, SEQ ID NO: 387, SEQ ID NO: 397, or SEQ ID NO: 407.

The disclosure further provides a vector comprising a polynucleotide as provided herein, and a composition comprising a polynucleotide or a vector as provided herein.

In certain aspects the disclosure provides a polynucleotide or a combination of polynucleotides encoding a NHP-derived pan-filovirus binding molecule, e.g., a cross-reactive anti-filovirus antibody or antigen-binding fragment thereof. In certain aspects the polynucleotide or combination of polynucleotides can comprise a nucleic acid encoding a VH, and a nucleic acid encoding a VL, wherein the VH and VL comprise VH-CDR1, VH-CDR2, VH-CDR3, VL-CDR1, VL-CDR2, and VL-CDR3 amino acid sequences identical or identical except for four, three, two, or one single amino acid substitutions, deletions, or insertions in one or more CDRs to: SEQ ID NOs 3, 4, 5, 8, 9, and 10; SEQ ID NOs 13, 14, 15, 18, 19, and 20; SEQ ID NOs 23, 24, 25, 28, 29, and 30; SEQ ID NOs 33, 34, 35, 38, 39, and 40; SEQ ID NOs 43, 44, 45, 48, 49, and 50; SEQ ID NOs 53, 54, 55, 58, 59, and 60; SEQ ID NOs 63, 64, 65, 68, 69, and 70; SEQ ID NOs 73, 74, 75, 58, 59, and 60; SEQ ID NOs 73, 84, 55, 58, 59, and 60; SEQ ID NOs 73, 84, 95, 58, 69, and 60; SEQ ID NOs 73, 84, 55, 58, 59, and 60; SEQ ID NOs 113, 74, 55, 58, 119, and 120; SEQ ID NOs 123, 74, 55, 58, 59, and 60; SEQ ID NOs 133, 84, 55, 58, 59, and 60; SEQ ID NOs 143, 84, 55, 58, 59, and 60; SEQ ID NOs 153, 84, 55, 58, 59, and 120; SEQ ID NOs 163, 164, 55, 58, 119, and 60; SEQ ID NOs 173, 84, 55, 68, 179, and 180; SEQ ID NOs 73, 64, 55, 68, 69, and 190; SEQ ID NOs 193, 84, 55, 68, 179, and 60; SEQ ID NOs 73, 84, 75, 58, 69, and 60; SEQ ID NOs 73, 84, 95, 58, 59, and 60; SEQ ID NOs 193, 224, 55, 58, 59, and 230; SEQ ID NOs 73, 234, 55, 58, 59, and 60; SEQ ID NOs 143, 244, 55, 58, 119, and 120; SEQ ID NOs 143, 84, 55, 58, 59, and 60; SEQ ID NOs 263, 264, 55, 58, 59, and 60; SEQ ID NOs 273, 274, 55, 68, 179, and 180; SEQ ID NOs 283, 274, 55, 58, 59, and 60; SEQ ID NOs 73, 164, 55, 58, 59, and 60; SEQ ID NOs 73, 74, 55, 308, 59, and 60; SEQ ID NOs 313, 74, 55, 58, 59, and 60; SEQ ID NOs 323, 84, 55, 68, 69, and 120; SEQ ID NOs 333, 84, 55, 58, 59, and 60; SEQ ID NOs 343, 84, 55, 58, 59, and 60; SEQ ID NOs 123, 84, 55, 58, 59, and 60; SEQ ID NOs 63, 84, 55, 58, 59, and 60; SEQ ID NOs 163, 84, 55, 58, 59, and 60; SEQ ID NOs 163, 84, 55, 58, 59, and 60; SEQ ID NOs 393, 84, 55, 58, 59, and 60; or SEQ ID NOs 73, 404, 55, 58, 59, and 60; respectively.

In certain aspects the polynucleotide or combination of polynucleotides can comprise a nucleic acid encoding a VH, and a nucleic acid encoding a VL, wherein the VH and VL comprise amino acid sequences at least 85%, 90%, 95%, or 100% identical to reference amino acid sequences selected from the group consisting of SEQ ID NO: 2 and SEQ ID NO: 7; SEQ ID NO: 12 and SEQ ID NO: 17; SEQ ID NO: 22 and SEQ ID NO: 27; SEQ ID NO: 32 and SEQ ID NO: 37; SEQ ID NO: 42 and SEQ ID NO: 47; SEQ ID NO: 52 and SEQ ID NO: 57; SEQ ID NO: 62 and SEQ ID NO: 67; SEQ ID NO: 72 and SEQ ID NO: 57; SEQ ID NO: 82 and SEQ ID NO: 87; SEQ ID NO: 92 and SEQ ID NO: 97; SEQ ID NO: 82 and SEQ ID NO: 107; SEQ ID NO: 112 and SEQ ID NO: 117; SEQ ID NO: 122 and SEQ ID NO: 127; SEQ ID NO: 132 and SEQ ID NO: 137; SEQ ID NO: 142 and SEQ ID NO: 57; SEQ ID NO: 152 and SEQ ID NO: 157; SEQ ID NO: 162 and SEQ ID NO: 167; SEQ ID NO: 172 and SEQ ID NO: 177; SEQ ID NO: 182 and SEQ ID NO: 187; SEQ ID NO: 192 and SEQ ID NO: 197; SEQ ID NO: 202 and SEQ ID NO: 207; SEQ ID NO: 212 and SEQ ID NO: 217; SEQ ID NO: 222 and SEQ ID NO: 227; SEQ ID NO: 232 and SEQ ID NO: 237; SEQ ID NO: 242 and SEQ ID NO: 247; SEQ ID NO: 142 and SEQ ID NO: 57; SEQ ID NO: 262 and SEQ ID NO: 267; SEQ ID NO: 272 and SEQ ID NO: 277; SEQ ID NO: 282 and SEQ ID NO: 57; SEQ ID NO: 292 and SEQ ID NO: 297; SEQ ID NO: 302 and SEQ ID NO: 307; SEQ ID NO: 312 and SEQ ID NO: 57; SEQ ID NO: 322 and SEQ ID NO: 327; SEQ ID NO: 332 and SEQ ID NO: 57; SEQ ID NO: 342 and SEQ ID NO: 347; SEQ ID NO: 352 and SEQ ID NO: 357; SEQ ID NO: 362 and SEQ ID NO: 57; SEQ ID NO: 372 and SEQ ID NO: 57; SEQ ID NO: 382 and SEQ ID NO: 387; SEQ ID NO: 392 and SEQ ID NO: 397; or SEQ ID NO: 402 and SEQ ID NO: 407; respectively.

In certain aspects of the polynucleotide or combination of polynucleotides as provided herein the nucleic acid encoding a VH and the nucleic acid encoding a VL can be in the same vector. Such a vector is also provided.

In certain aspects of the polynucleotide or combination of polynucleotides as provided herein the nucleic acid encoding a VH and the nucleic acid encoding a VL can be in different vectors. Such vectors are further provided.

The disclosure also provides a host cell comprising the polynucleotide or combination of polynucleotides as provided herein or the vector or vectors as provided.

Moreover, the disclosure provides a method of making a NHP-derived pan-filovirus binding molecule, e.g., a cross-reactive anti-filovirus antibody or antigen-binding fragment thereof, comprising culturing a host cell as provided; and isolating the NHP-derived binding molecule or fragment thereof or antibody or fragment thereof.

In certain embodiments, the polynucleotides comprise the coding sequence for the mature NHP-derived pan-filovirus binding molecule, e.g., a cross-reactive anti-filovirus antibody or antigen-binding fragment thereof, fused in the same reading frame to a marker sequence that allows, for example, for purification of the encoded polypeptide. For example, the marker sequence can be a hexa-histidine tag (SEQ ID NO: 416) supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) can be used.

Polynucleotide variants are also provided. Polynucleotide variants can contain alterations in the coding regions, non-coding regions, or both. In some embodiments polynucleotide variants contain alterations that produce silent substitutions, additions, or deletions, but do not alter the properties or activities of the encoded polypeptide. In some embodiments, polynucleotide variants can be produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*). Vectors and cells comprising the polynucleotides described herein are also provided.

In some embodiments, a DNA sequence encoding a NHP-derived pan-filovirus binding molecule, e.g., a cross-reactive anti-filovirus antibody or antigen-binding fragment thereof can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest can be inserted into an expression vector and operatively linked to an expression control sequence appropriate for expression of the protein in a desired host. Proper assembly can be confirmed, e.g., by nucleotide sequencing, restriction mapping, and/or expression of a biologically active polypeptide in a suitable host. In order to obtain high expression levels of a transfected gene in a host, the gene can be operatively linked to or associated with transcriptional and translational expression control sequences that are functional in the chosen expression host.

In certain embodiments, recombinant expression vectors can be used to amplify and express DNA encoding a NHP-derived pan-filovirus binding molecule, e.g., a cross-reactive anti-filovirus antibody or antigen-binding fragment thereof. Recombinant expression vectors are replicable DNA constructs which have synthetic or cDNA-derived DNA fragments encoding a polypeptide chain of an anti-filovirus antibody or and antigen-binding fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which can be transcribed into mRNA and translated into protein, and (3) appropriate transcription and translation initiation and termination sequences, as described in detail below. Such regulatory elements can include an operator sequence to control transcription. The ability to replicate in a host, conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where a recombinant protein is expressed without a leader or transport sequence, the protein can include an N-terminal methionine. This methionine can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

Suitable host cells for expression of a NHP-derived pan-filovirus binding molecule, e.g., a cross-reactive anti-filovirus antibody or antigen-binding fragment thereof include prokaryotes, yeast, insect or higher eukaryotic cells under the control of appropriate promoters. Prokaryotes include gram negative or gram-positive organisms, for example *E. coli* or bacilli. Higher eukaryotic cells include established cell lines of mammalian origin as described below. Cell-free translation systems could also be employed. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems can also be employed to express a NHP-derived pan-filovirus binding molecule, e.g., a cross-reactive anti-filovirus antibody or antigen-binding fragment thereof. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as ribosome binding sites, a polyadenylation site, splice donor and acceptor sites, and transcriptional termination sequences. Baculovirus systems for production of heterologous proteins in insect cells are reviewed by Luckow and Summers, BioTechnology 6:47 (1988).

A NHP-derived pan-filovirus binding molecule, e.g., a cross-reactive anti-filovirus antibody or antigen-binding fragment thereof produced by a transformed host, can be purified according to any suitable method. Such standard methods include chromatography (e.g., ion exchange, affinity and sizing column chromatography), centrifugation, differential solubility, or by any other standard technique for protein purification. Affinity tags such as hexahistidine (SEQ ID NO: 416), maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a NHP-derived pan-filovirus binding molecule, e.g., a cross-reactive anti-filovirus antibody or antigen-binding fragment thereof. Some or all of the foregoing purification steps, in various combinations, can also be employed to provide a homogeneous recombinant protein.

A NHP-derived pan-filovirus binding molecule, e.g., a cross-reactive anti-filovirus antibody or antigen-binding fragment thereof produced in bacterial culture, can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

Treatment Methods Using NHP-Derived Pan-Filovirus Binding Molecules

Methods are provided for the use of NHP-derived pan-filovirus binding molecules, e.g., cross-reactive anti-filovirus antibodies or fragments thereof, to treat patients having a disease or condition associated with a filovirus infection, or to prevent, reduce, or manage filovirus-induced virulence in a subject infected with a filovirus.

The following discussion refers to diagnostic methods and methods of treatment of various diseases and disorders with a NHP-derived pan-filovirus binding molecule, e.g., a cross-reactive anti-filovirus antibody or antigen-binding fragment thereof that retains the desired properties of anti-filovirus antibodies provided herein, e.g., capable of specifically binding to and neutralizing filovirus infectivity and/or virulence. In some embodiments, a NHP-derived pan-filovirus binding molecule, e.g., a cross-reactive anti-filovirus antibody or antigen-binding fragment thereof can be a murine, human, or humanized antibody. In some embodiments, the anti-filovirus antibody or antigen-binding fragment thereof comprises a binding domain that binds to the same epitope as, or competitively inhibits binding of, one or more of macaque monoclonal antibodies FVM01P, FVM02P, FVM03, FVM04, FVM05, FVM06, FVM07, FVM08, FVM09, FVM10, FVM11, FVM12, FVM13, FVM14, FVM15, FVM16, FVM17, FVM18, FVM19, FVM20, FVM21, FVM22, FVM23, FVM24, FVM25, FVM26, FVM27, FVM28, FVM29, FVM31, FVM32, FVM33, FVM34, FVM35, FVM36, FVM37, FVM38, FVM39, FVM40, FVM41, or FVM42 as provided herein. In some embodiments, the binding domain of an anti-filovirus antibody or antigen-binding fragment thereof as provided herein can be derived from one or more of macaque monoclonal antibodies FVM01P, FVM02P, FVM03, FVM04, FVM05, FVM06, FVM07, FVM08, FVM09, FVM10, FVM11, FVM12, FVM13, FVM14, FVM15, FVM16, FVM17, FVM18, FVM19, FVM20, FVM21, FVM22, FVM23, FVM24, FVM25, FVM26, FVM27, FVM28, FVM29, FVM31, FVM32, FVM33, FVM34, FVM35, FVM36, FVM37, FVM38, FVM39, FVM40, FVM41, or FVM42 as provided herein. In certain embodiments the binding domain of the derived antibody can be an affinity-matured, chimeric, or humanized antibody. In some embodiments a NHP-derived pan-filovirus binding molecule, e.g., a cross-reactive anti-filovirus antibody or antigen-binding fragment thereof further comprises a second binding domain that can target the binding domain to the endosome of a virus-infected cell.

In one embodiment, treatment includes the application or administration of a NHP-derived pan-filovirus binding molecule, e.g., a cross-reactive anti-filovirus antibody or antigen-binding fragment thereof as provided herein, to a subject or patient, where the subject or patient has been exposed to a filovirus, infected with a filovirus, has a filovirus disease, a symptom of a filovirus disease, or a predisposition toward contracting a filovirus disease. In another embodiment, treatment can also include the application or administration of a pharmaceutical composition comprising a NHP-derived pan-filovirus binding molecule, e.g., a cross-reactive anti-filovirus antibody or antigen-binding fragment thereof as provided herein, to a subject or patient, so as to target the pharmaceutical composition to an environment where the NHP-derived binding molecule can be most effective, e.g., the endosomal region of a virus-infected cell.

In accordance with the methods of the present disclosure, at least one NHP-derived pan-filovirus binding molecule, e.g., a cross-reactive anti-filovirus antibody or antigen-binding fragment thereof as defined elsewhere herein, can be used to promote a positive therapeutic response. By "positive therapeutic response" is intended any improvement in the disease conditions associated with the activity of the NHP-derived binding molecule, and/or an improvement in the symptoms associated with the disease. Thus, for example, an improvement in the disease can be characterized as a complete response. By "complete response" is intended an absence of clinically detectable disease with normalization of any previously test results. Such a response can in some cases persist, e.g., for at least one month following treatment according to the methods of the disclosure. Alternatively, an improvement in the disease can be categorized as being a partial response.

Pharmaceutical Compositions and Administration Methods

Methods of preparing and administering a NHP-derived pan-filovirus binding molecule, e.g., a cross-reactive anti-filovirus antibody or antigen-binding fragment thereof provided herein, to a subject in need thereof are well known to or are readily determined by those skilled in the art. The route of administration of a NHP-derived pan-filovirus binding molecule, e.g., a cross-reactive anti-filovirus antibody or antigen-binding fragment thereof can be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as suitable forms, another example of a form for administration would be a solution for injection, in particular for intravenous or intraarterial injection or drip. In some cases a suitable pharmaceutical composition can comprise a buffer (e.g. acetate, phosphate or citrate buffer), a surfactant (e.g. polysorbate), optionally a stabilizer agent (e.g. human albumin), etc. In other methods compatible with the teachings herein, a NHP-derived pan-filovirus binding molecule, e.g., a cross-reactive anti-filovirus antibody or antigen-binding fragment thereof as provided herein can be delivered directly to a site where the binding molecule can be effective in virus neutralization, e.g., the endosomal region of a filovirus-infected cell.

As discussed herein, a NHP-derived pan-filovirus binding molecule, e.g., a cross-reactive anti-filovirus antibody or antigen-binding fragment thereof provided herein, can be administered in a pharmaceutically effective amount for the in vivo treatment of diseases or disorders associated with filovirus infection. In this regard, it will be appreciated that the disclosed binding molecules can be formulated so as to facilitate administration and promote stability of the active agent. Pharmaceutical compositions accordingly can comprise a pharmaceutically acceptable, non-toxic, sterile carrier such as physiological saline, non-toxic buffers, preservatives and the like. A pharmaceutically effective amount of a NHP-derived pan-filovirus binding molecule, e.g., a cross-reactive anti-filovirus antibody or antigen-binding fragment thereof means an amount sufficient to achieve effective binding to a target and to achieve a benefit, e.g., to ameliorate symptoms of a disease or condition or to detect a substance or a cell. Suitable formulations for use in the therapeutic methods disclosed herein can be described in Remington's Pharmaceutical Sciences (Mack Publishing Co.) 16th ed. (1980).

The amount of a NHP-derived pan-filovirus binding molecule, e.g., a cross-reactive anti-filovirus antibody or antigen-binding fragment thereof that can be combined with carrier materials to produce a single dosage form will vary depending upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, a NHP-derived pan-filovirus binding molecule, e.g., a cross-reactive anti-filovirus antibody or antigen-binding fragment thereof can be administered to a human or other animal in accordance with the aforementioned methods of treatment in an amount sufficient to produce a therapeutic effect. A NHP-derived pan-filovirus binding molecule, e.g., a cross-reactive anti-filovirus antibody or antigen-binding fragment thereof provided herein can be administered to such human or other animal in a conventional dosage form prepared by combining the antibody or antigen-binding fragment, variant, or derivative thereof of the disclosure with a conventional pharmaceutically acceptable carrier or diluent according to known techniques. The form and character of the pharmaceutically acceptable carrier or diluent can be dictated by the amount of active ingredient with which it is to be combined, the route of administration and other well-known variables.

By "therapeutically effective dose or amount" or "effective amount" is intended an amount of a NHP-derived pan-filovirus binding molecule, e.g., a cross-reactive anti-filovirus antibody or antigen-binding fragment thereof, that when administered brings about a positive therapeutic response with respect to treatment of a patient with a disease or condition to be treated.

Therapeutically effective doses of the compositions disclosed herein, for treatment of diseases or disorders associated with filovirus infection, vary depending upon many different factors, including means of administration, target site, physiological state of the patient, whether the patient is human or an animal, other medications administered, and whether treatment is prophylactic or therapeutic. Usually, the patient is a human, but non-human mammals including non-human primates can also be treated. Treatment dosages can be titrated using routine methods known to those of skill in the art to optimize safety and efficacy.

The amount of a NHP-derived pan-filovirus binding molecule, e.g., a cross-reactive anti-filovirus antibody or antigen-binding fragment thereof to be administered can be readily determined by one of ordinary skill in the art without undue experimentation given this disclosure. Factors influencing the mode of administration and the respective amount of a NHP-derived pan-filovirus binding molecule, e.g., a cross-reactive anti-filovirus antibody or antigen-binding fragment thereof include, but are not limited to, the severity of the disease, the history of the disease, and the age, height, weight, health, and physical condition of the individual undergoing therapy. Similarly, the amount of a NHP-derived pan-filovirus binding molecule, e.g., a cross-reactive anti-filovirus antibody or antigen-binding fragment thereof to be administered will be dependent upon the mode of administration and whether the subject will undergo a single dose or multiple doses of this agent.

This disclosure also provides for the use of a NHP-derived pan-filovirus binding molecule, e.g., a cross-reactive anti-filovirus antibody or antigen-binding fragment thereof in the manufacture of a medicament for treating, preventing, or managing a disease or disorder associated with filovirus infection, e.g., hemorrhagic fever.

Kits Comprising NHP-Derived Pan-Filovirus Binding Molecules

This disclosure further provides kits that comprise a NHP-derived pan-filovirus binding molecule, e.g., a cross-reactive anti-filovirus antibody or antigen-binding fragment thereof as described herein and that can be used to perform the methods described herein. In certain embodiments, a kit comprises a NHP-derived pan-filovirus binding molecule, e.g., a cross-reactive anti-filovirus antibody or antigen-binding fragment thereof in one or more containers. In some embodiments, the kits contain all of the components necessary and/or sufficient to perform a detection assay, including controls, directions for performing assays, and software for analysis and presentation of results. One skilled in the art will readily recognize that a NHP-derived pan-filovirus binding molecule, e.g., a cross-reactive anti-filovirus antibody or antigen-binding fragment thereof as provided herein can be readily incorporated into one of the established kit formats which are well known in the art. See also point-of-care immunoassay kits described below.

Immunoassays

A NHP-derived pan-filovirus binding molecule, e.g., a cross-reactive anti-filovirus antibody or antigen-binding fragment thereof can be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety).

In certain aspects, this disclosure provides a diagnostic kit. In certain aspects, such a kit comprises a portable immunoassay that can be performed by a healthcare provider at the point-of-care to provide a rapid indication of whether a patient is infected with a filovirus, e.g., EBOV. Various point of care diagnostic assays are known and used in the art. See, e.g., Pfeilsticker, J A, et al., PLoS One 8:e76224 (2013); Wang, H K, et al., Adv Healthc Mater 3:187-96 (2014); Yetisen, A K, et al., Lab Chip 13:2210-51 (2013); Loubiere, S. and Moatti, J P, Clin Microbiol Infect 16:1070-6 (2010); and Offermann, N., et al., J Immunol Methods 403:1-6 (2014); all of which are incorporated herein by reference in their entireties.

In certain aspects, the diagnostic kit provided by the disclosure comprises a NHP-derived pan-filovirus binding molecule, e.g., a cross-reactive anti-filovirus antibody or antigen-binding fragment thereof, or a composition comprising such binding molecule or antibody as provided herein, and instructions for using the binding molecule or antibody or fragment thereof or using the composition or directions for obtaining instructions for using the antibody or fragment thereof or using the composition. In certain aspects, the kit can be in the form of a test strip, e.g., enclosed in a plastic cassette where the test strip comprises a filter or other solid support. In certain aspects the binding molecule or antibody as provided herein can be associated with the solid support, or can be in a buffer or other solution to be applied to the solid support at some point in the assay. A solid support can be, e.g., a bead, a filter, a membrane or a multiwall plate. In some aspects, the diagnostic kit is in the form of an enzyme-linked immunosorbent assay (ELISA). For example, the antibody or binding molecule as provided herein can be associated with a solid support, a sample obtained from a subject can be applied to the solid support, and any filovirus antigen in the subject's sample can be detected with a second antibody. In certain aspects, the sample can be applied directly to the solid support and can be detected by the antibody or binding molecule either elsewhere on the solid support or the antibody can be applied directly to the sample. In each case, the antibody can be detected with a secondary antibody or other reagent conjugated to an enzyme that can be detected by, e.g., a color change.

In certain aspects, a diagnostic test can be carried out by a healthcare provider at the point-of-care using a kit as provided herein, thereby diagnosing whether the patient is infected with a filovirus. As used herein, the term "healthcare provider" refers to individuals or institutions that directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

In certain aspects, a diagnostic test can be carried out by a carried out at a clinical laboratory using samples provided by a healthcare provider. As used herein, the term "clinical laboratory" refers to a facility for the examination or processing of materials or images derived from a living subject, e.g., a human being. Non-limiting examples of processing include biological, biochemical, serological, chemical, immunohematological, hematological, biophysical, cytological, pathological, genetic, image based, or other examination of materials derived from the human body or of any or all of the human body for the purpose of providing information, e.g., for the diagnosis, prevention, or treatment of any disease or impairment of, or the assessment of the health of living subjects, e.g., human beings. These examinations can also include procedures to collect or otherwise obtain an image, a sample, prepare, determine, measure, or otherwise describe the presence or absence of various substances in the body of a living subject, e.g., a human being, or a sample obtained from the body of a living subject, e.g., a human being.

The disclosure further provides a method of determining whether a subject is infected with a filovirus. In certain aspects the method includes obtaining a sample from a subject suspected of being infected with a filovirus. The sample can be obtained by a healthcare provider for use in a point-of-care assay, or by a clinical laboratory, where the clinical laboratory can directly obtain the sample from the subject, or the sample can be provided by a healthcare provider. The method can further include applying the sample to reagents or objects provided in the diagnostic kit, e.g., the sample can be applied to a solid support, or can be mixed into a buffer or other liquid reagent. In certain aspects the sample is suspected of containing filovirus antigens. In certain aspects the sample is suspected of containing antibodies to filovirus antigens.

Using an immunoassay that utilizes a NHP-derived pan-filovirus binding molecule, e.g., a cross-reactive anti-filovirus antibody or antigen-binding fragment thereof as provided herein, the user, e.g., a healthcare provider or a clinical laboratory, can determine whether the sample reacts with the antibody or fragment thereof provided in the kit or with a filovirus antigen bound to the antibody or fragment thereof (e.g., in a sandwich assay), wherein a positive reaction indicates that the subject is infected with a filovirus. In certain aspects the sample can be blood or any fraction thereof, e.g., serum, plasma, or cells, urine, feces, saliva, vomitus, or any combination thereof. In certain aspects, the determination of whether the individual is infected with a filovirus can be made in less than 24 hours, less than 12 hours, less than 6 hours, less than 5 hours, less than 4 hours, less than 3 hours, less than one hour, or less than 30 minutes of application of the sample to the elements of the kit.

The binding activity of a given lot of a NHP-derived pan-filovirus binding molecule, e.g., a cross-reactive anti-filovirus antibody or antigen-binding fragment thereof can be determined according to well-known methods. Those skilled in the art will be able to determine operative and optimal assay conditions for each determination by employing routine experimentation.

Methods and reagents suitable for determination of binding characteristics of a NHP-derived pan-filovirus binding molecule, e.g., a cross-reactive anti-filovirus antibody or antigen-binding fragment thereof are known in the art and/or are commercially available. Equipment and software designed for such kinetic analyses are commercially available (e.g., BIAcore®, BIAevaluation® software, GE Healthcare; KINEXA® Software, Sapidyne Instruments).

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. (See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described can be followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevier, Amsterdam); Goldsby et al., eds. (2000) Kuby Immunology (4th ed.; W.H. Freeman & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlag); Sambrook and Russell (2001) Molecular Cloning: A Laboratory Manual (Cold Spring Harbor Press); Lewin (2003) Genes VIII (Prentice Hall, 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1: Generation of Macaque Monoclonal Antibodies Against Filovirus Glycoproteins 1.1 Immunization:

Immunization was designed with a prime boost strategy to elicit antibodies with broad reactivity towards multiple species of filoviruses. Two rhesus macaques were vaccinated with four regimens of antigens. On days 0, 28, and 56, the animals received 250 µg of each protein, EBOV, SUDV, and MARV GPddmuc (produced in insect cells) via the IM route along with 50 µg of the adjuvant IDC-1001. On day 84 the animals received 1 mg of each, EBOV, SUDV, and MARV VLPs (produced in insect cells) via the IM route along with 50 µg of the adjuvant IDC-1001. Peripheral blood mononuclear cells (PBMC) and sera were collected on days 0, 28, 56, 84, 112, and the study end point, day 191. Sera from all time points were analyzed for anti-filovirus GP antibodies using ELISA with VLPs and purified GPddmuc and GPdTM proteins as coating antigens. PBMC from day 112 were used for the isolation of B cells.

1.2 B Cell Isolation:

Rhesus Macaque PBMC that were isolated on Day 112 after immunization with Ebola virus GPs were used for B cell isolation, activation, antigen-specific B cell sorting and antibody isolation. CD20+ B cells were positively selected with magnetic beads (Miltenyi, Auburn, Calif. 130-091-105), according to the manufacturer's product instruction. A total of 5% CD20+ cells (approximately 1,100,000 B cells) were recovered from input PBMC (2.2E7 cells).

1.3 B Cell Activation:

In preparation of B cells activation, MS40L feeder cells expressing surface human CD40L (Huang et al, 2013, *Nature Protocols*, 8:1907-1915; Luo et al, 2009, Blood 113:1422-1431), were irradiated with 78 gray and seeded at 25,000 cells per well in 96-well plates or 725,000 cell per well in 6-well plates. Macaque B cells were plated at a density of 4 cells per well in fifty 96-well plates. Only the inner 60 wells were plated with feeders and B cells to minimize the effects of evaporation. Thirty-two of the 36 outer wells contained 100 µl of sterile distilled H$_2$O and the other 4 outer wells were plated with only feeder cells, as no-IgG controls. These were used as negative controls in subsequent screening of the supernatants from cells plated in the inner 60 wells. The remaining macaque B cells were plated at a density of approximately 20,000 cells per well in 6-well plates For activation, B cells combined with feeder cells were cultured in IMDM medium (Invitrogen, Carlsbad, Calif.) containing 10% FCS (Sigma-Aldrich Co., St. Louis, Mo.), 2 mM glutamine, 100 u/ml penicillin, 100 µg/ml streptomycin (Invitrogen), and supplemented with 1 µg/ml CpG (ODN-2006) (Operon) and 50 ng/ml recombinant-human interleukin-21 (IL-21) (Peprotech), and incubated at 37° C. in 5% CO2 for 13 days as described (Brocca-Cofano et al, 2011, *Vaccine*, 29:3310-3319). CpG and IL-21 were replenished very 3-5 days.

1.4 Identification of Antigen-Specific B Cells:

Two pathways were employed to identify antigen-specific B cells on Day 13 of activation, as illustrated in FIG. 4. B cells activated in 96-well plates were screened by ELISA for antigen-specific IgG secretion. B cells activated in 6-well plates were used for isolation of antigen-specific B cells by FACS sorting.

Pathway 1: Screening for Antigen-Specific IgG Secretion.

Supernatants in 96-well plates containing activated B cells were collected on Day 13 to test for binding to filovirus glycoproteins by ELISA, as described previously with slight modifications (Keck Z Y, 2012, *PLoS Pathogens*, 8:e1002653). Briefly, microtiter plates were pre-coated in each well with 150 ng of three combined GPs (from SUDV/EBOV/MARV, at 50 ng/well of each GP) in separated forms of GPddmuc or full length ectodomain (GPdTM) at 40° C. for overnight. The wells were blocked with 2.5% non-fat dry milk and 2.5% normal goat serum. 40 µl of cell supernatants collected from 96-wells plates were added to the pre-coated wells. The bound antibodies in the supernatants was detected by anti-human immunoglobulin G (IgG)-horseradish peroxidase (Sigma) and TMB (3,3', 5', 5'-tetramethylbenzidine, sigma) substrate. Absorbance was measured at 450 nm and 570 nm. Vaccinated macaque serum was used as the positive control at 1:1000 dilutions and supernatants from well containing only feeder cells, collected on Day 13, were used as the negative control.

Pathway 2: Screening Antigen-Specific B Cells by FACS Sorting.

B cells activated in 6-well plates were used for antigen-specific B cells FACS sorting. 100 million B cells collected on Day 13 activation were equally divided and two sets of 50 million B cells were incubated with either combined triple antigens mixture (SUDV/EBOV/MARV) GPddmuc or GPdTM respectively at 4° C. for 30 min in FACS wash buffer and washed in cold wash buffer. The glycoproteins contained a hemagglutinin (HA) tag at the C terminus for detection. The cells were then incubated with anti-HA (Phycoerythrin (PE)-labeled) (1:400, Roche) for 30 min at 4° C. The labeled B cells were washed and re-suspended in FACS wash buffer at 1×10$^7$ cells/ml for sorting by flow cytometry. B cells without antigen staining were used as a negative control. Selection was performed using a BD Bioscience FACS Vantage Sorter. Approximately 150,000 antigen-specific B cells were collected from each sorting and total RNA was extracted with RNeasy Mini Kit (Qiagen) according to the manufacturer's product instruction. RNA was used to generate immune yeast display antibody libraries, see below in section V 1.5 Direct Ig VH, Vκ and Vλ Cloning from B-Cell RT-PCR Reverse Transcription of Antibody Messenger RNA:

The genes encoding Ig VH Vκ and Vλ from the positive wells were recovered directly using RT-PCR, as previously described (Liao et al, 2009, *J Virol Methods*, 158:171-179; Tiller et al, 2008, *J Immunol Methods*, 329:112-124) with following modifications. The B cells from each well that secreted antigen-specific IgG were lysed and cDNA was synthesized in a total volume of 20 µl per reaction containing first strand synthesis buffer (Invitrogen) in the PCR tubes (Applied Biosystems). Total RNA from B cells was reverse transcribed by adding 2 µl of random hexamer primers (Invitrogen) at 50 µM, 1 µl of 10 mM dNTP mix (Invitrogen), 0.0625 µl of Igepal CA-630 (Sigma), 40 units of RNaseOUT™ (Invitrogen), 2 µl of 0.1 dithiothreitol (DTT) (Invitrogen) and 50 U of SuperScript III reverse transcriptase (Invitrogen) into each well. Reverse transcription (RT) reaction was performed at 42° C. for 10 min, 25° C. for 10 min, 50° C. for 60 min and 94° C. for 5 min.

Amplification of IgH, Igκ and Igλ Genes and Expression Vector Cloning:

The IgH, Igκ and Igλ V genes were amplified separately by nested PCR starting from 1 µl of cDNA directly following the RT and the nested PCR on 1 µl of the first round PCR product, as previously described (Sundling et al, 2012, *J*

*Immunol Methods*, 386:85-93) with the following modifications. All PCRs were performed in a total volume of 20 µl containing nuclease-free water, 4 µl of 5× buffer, 0.4 µl of 10 mM dNTP mix (Invitrogen), 0.8 µl of 40 µM mixture of forward and reverse primers, as described (Sundling et al, 2012, *J Immunol Methods*, 386:85-93), and 0.4 µl of PHusion polymerase (New England Biolabs). The PCR program was initiated by 5 min incubation at 94° C. followed by 40 cycles of 94° C., 30 s, 55° C. (for first round of PCR) or 60° C. (for nested round of PCR), 30 s, and 70° C. 60 s. There was a final elongation step at 70° C. for 7 min before cooling to 4° C. The PCR products were evaluated on 2% agarose gels after the nested PCR. The fragments for matching heavy/light chain pairs (bands~500 bp for heavy chain and ~450 bp for lambda and kappa light chains) were purified using a QIAquick gel extraction kit (Qiagen, Valencia, Calif.), and ligated into the pCR4-TOPO cloning/sequencing vector (Invitrogen, Carlsbad, Calif.). Individual clones containing an insert of the expected size were sequenced in both sense and antisense strands (Elim Biopharm, Hayward, Calif.). Because four B cells were plated per well, 10 individual clones from each IgH, Igλ or Igκ PCR reactions were sequenced to evaluate the diversity. One of the positive B cell well had only one unique pair of heavy- and light-chain. The second well had four unique heavy- and four unique light-chains. The clones that represented productive IgH, Igλ or Igκ rearranged sequences were reamplified using cloning primers flanking with unique restriction digest sites for cloning into expression vector (Smith et al, 2009, *Nature Protocols*, 4:372-384). After amplification, DNA fragments were gel purified, digested and cloned into IgG-AbVec, Igκ-AbVec and Igλ-AbVec containing a murine Ig gene signal peptide sequence and variable-gene cloning sites upstream of the human Igγ1, Igκ or Igλ constant regions.

Full Length IgG Production and Identification of Specific Paired Ig Genes:

Plasmid constructs carrying antibody variable-heavy and variable-light rearranged genes from the two positive wells that are in-frame with the signal peptide and constant region genes were co-transfected into the 293T cell line (ATCC) for small scale expression, as described previously (Keck Z Y, 2012, *PLoS Pathogens*, 8:e1002653). The cells were grown in Dulbecco's modified minimal essential medium (Invitrogen) supplemented with 10% fetal calf serum (Gemini Bioproducts Inc.) and 2 mM glutamine for 5 days at 37° C./5% $CO_2$. In the case of four unique heavy- and four unique light-chains, sixteen possible combinations of heavy- and light-chain pairs were co-transfected into 293T cells. Supernatants were collected on Day 5 and tested for binding to filovirus GPs by ELISA. The positive IgG concentrations (82-124 µg/ml) were determined by ELISA. The resulting secreted antibodies after cleavage of the signal peptide gave rise to chimeric macaques-human (Fc) monoclonal antibodies.

Ig Gene Sequence Analysis:

DNA sequences from the matching heavy/light chain pairs that produce desired antibody (designated as: FVM01p and FVM02p) were analyzed using the IMGT information system (www.imgt.cines.fr/) (IMGT®/V-Quest) to identify variable region gene segments as shown in Tables 2 and 3.

TABLE 2

Macaque Antibody VH and VL Sequences

| SEQ ID | Heavy Chain<br>Heavy Chain Variable region | SEQ ID | Light Chain<br>Light Chain variable region |
|---|---|---|---|
| | FVM01P: | | |
| 1 | caggtgcagctgcaggagtcgggcccaggactggtga<br>agccctcggagaccctgtccctcacctgcactgtctctgg<br>tgcctccattagtaattacaggtggaactggatccgcca<br>gcccccagggaagggactggagtggattggggagatc<br>aatggttatagtgggagcaccaactacaacccctccctc<br>aagagtcgagtcaccattttcaaaagacgcgtccaagaa<br>ccagttctccctgaagctgacctctgtgaccgccgcgga<br>cacggccgtgtattactgtccaataattgggggctttact<br>ttagagtggttcgatgtctggggcccgggagtcctggtc<br>accgtctcctca | 6 | Gatgttgtgctgacccagtctccatcctccctgtctgcatctg<br>taggagacagagtcaccatcacttgcagggcaagtcaggg<br>cattagaaattatttaaattggtatcagcagaaaccaagaa<br>aagctcctaagctcctgatctatgctgcatccagtttgcaaa<br>gtggggtcccatcaaggttcagcggcagtggatctgggac<br>agaattcactctcaccatcagcagcctgcaggctgaagatt<br>ttgctacttactactgtctacagggttatagaacccattcac<br>tttcggccccgggaccaaactggatatcaaacgtacggtg |
| 2 | QVQLQESGPGLVKPSETLSLTCTVSGASIS<br>NYRWNWIRQPPGKGLEWIGEINGYSGST<br>NYNPSLKSRVTISKDASKNQFSLKLTSVT<br>AADTAVYYCPIIGGFTLEWFDVWGPGV<br>LVTVSS | 7 | DVVLTQSPSSLSASVGDRVTITCRASQGIRN<br>YLNWYQQKPRKAPKLLIYAASSLQSGVPSR<br>FSGSGSGTEFTLTISSLQAEDFATYYCLQGY<br>RTPFTFGPGTKLDIKRTV |
| | FVM02P: | | |
| 11 | Gaggtgcagctggtggagtccggggggaggcttggtcca<br>gcctggcgggtccctgagactctcctgtgcagcctctgg<br>attcactggattcaccttcagtgattatgctttctactggg<br>tccgccaggctccaggaaaggggctagaatgggtgggt<br>ttcattagaggcaaagcttatggtgggacagcagattac<br>gccgcgtctgtgaaaggcagattcaccatctccagagat<br>aattcaaagaatacggcgtatctgcaaatgagcagcct<br>gaaaaccgaggactcggccgtatattattgtactagtca<br>gggtgtaacagtagccacaccttaccactggggccagg<br>gagtcctggtcaccgtctcctca | 16 | Gacattgtgctgacccagtctccactctccctgcccgtcacc<br>cctggagagccggcctccatctcctgcaggtctagtcagag<br>cctcctgcatagtggtgggaaaaacctattttgtattggtacct<br>gcagaagccaggccagtctccacagctcttgatccatgagg<br>tttccaaccgggcctctggagtccctgacaggttcagtggc<br>agtgggtcaggcactgatttcacactgaaaatcagccggt<br>ggaggctgaggatgttggggtttattactgcatgcaaggta<br>tacagcttcctctcactttcggcggagggaccaaggtggag<br>atcaaacgtacggtg |
| 12 | EVQLVESGGGLVQPGGSLRLSCAASGFTG<br>FTFSDYAFYWVRQAPGKGLEWVGFIRG<br>KAYGGTADYAASVKGRFTISRDNSKNTA<br>YLQMSSLKTEDSAVYYCTSQGVTVATPY<br>HWGQGVLVTVSS | 17 | DIVLTQSPLSLPVTPGEPASISCRSSQSLLHS<br>GGKTYLYWYLQKPGQSPQLLIHEVSNRASG<br>VPDRFSGSGSGTDFTLKISRVEAEDVGVYYC<br>MQGIQLPLTFGGGTKVEIKRTV |

TABLE 2-continued

Macaque Antibody VH and VL Sequences

| SEQ ID | Heavy Chain<br>Heavy Chain Variable region | SEQ ID | Light Chain<br>Light Chain variable region |
|---|---|---|---|
| | FVM03: | | |
| 21 | caggtgcagctgcaggagtcgggcccagtactggtgaa gccttcggagaccctgtccctcacctgcgctgtctctggt tactccatcagcagtgcttatgcctggagctggatccgc cagcccccagggaagggctggagtgggttggatatgt cggtagtagtagtgactacaaccccctccctcaagagtcg agtcaccattcaagagacacgtccaagaacggatctt cctgaacctgaggtctctgaccgccgcggacacggccg tgtattactgtgcgagagacagggcgaacaactcaatg gatgtctggggccggggagtctggtcaccgtctcctca | 26 | Gaaattgtgctgactcagtctccagactccctgggtgtgtct ctgggagagagggtcaccatcaactgcaagtccagccaga gtcttttatacagctccaacaataagaactacttagcctggt accagcagaaaccaggacaggctcctaagctgctcatttac tgggcatctactcggtaactctggggtccctaaccgattcagt ggcagcgggtctgggacagatttcactctcaccatcagtg cctgcaggctgaagatgtggcagtgtattactgtcagagt attatagtactcctctgacgttcggccaagggaccaaggtg gaaatcaaacgtacggtg |
| 22 | QVQLQESGPVLVKPSETLSLTCAVSGYSIS SAYAWSWIRQPPGKGLEWVGYVGSSSDY NPSLKSRVTISRDTSKNRIFLNLRSLTAAD TAVYYCARDRANNSMDVWGRGVLVTVS S | 27 | EIVLTQSPDSLGVSLGERVTINCKSSQSLLYS SNNKNYLAWYQQKPGQAPKLLIYWASTRE SGVPNRFSGSGSGTDFTLTISGLQAEDVAVY YCQQYYSTPLTFGQGTKVEIKRTV |
| | FVM04: | | |
| 31 | Gaggtgcagctggtgcagtctggggaggcttggtgca gcctgggggtccatgagactctcctgtgaagcctctgg attaagtctcagtgactacttcatgcactgggtccgccag gctcaaggaaaggactagagtggataggtttaataca aaccaaagctttcacttacaagacagaatatcctgcggc tgtgaaaggcagattcaccatctcaagagatgattcaaa gaacacgctgtatctacaaatgagcagcctgaaaccg aggacacagccctctattactgtattgcagtaactccag acttttactattggggccagggagtcctggtcaccgtctc ctca | 36 | gatgttgtgatgactcagtctccatctttcctgtctgcatctgt aggagacagagtcaccatcacttgcagggcaagtcaggac attaccattaattaaattggtttcagcataaaccaggaaaa gctcctaagcgcctgatctatgttgtgcatctagattggaaagg ggtccccatcaaggttcagtggcagtggatctgggacag aattcactctcactatcagcagcctcagcctgaagattttg caactattactgtcaacaatataataattacccctctcacttt cggccccgggaccaaactggatatcaaacgtacggtg |
| 32 | EVQLVQSGGGLVQPGGSMRLSCEASGLS LSDYFMHWVRQAQGKGLEWIGLIQTKA FTYKTEYPAAVKGRFTISRDDSKNTLYLQ MSSLKPEDTALYYCIAVTPDFYYWGQGV LVTVSS | 37 | DVVMTQSPSFLSASVGDRVTITCRASQDITI NLNWFQHKPGKAPKRLIYVASRLERGVPSR FSGSGSGTEFTLTISSLQPEDFATYYCQQYN NYPLTFGPGTKLDIKRTV |
| | FVM05: | | |
| 41 | Caggtgcagctgcaggagtcgggcccaggactggtga agccttcggagaccctgtccctcacctgcgctgtctctgg tttctccatcagcagtggttatggctggagctggatccgc cagcccccagggaagggctggagtgggattggctatat cgggggtagtagtggtagcaccagctacaaccccctcct caagagtcgagtcaccctgtcagcagacacgtccaaga atcagttctccctgaaactgagctctgtgaccgccgcg acacggccgtgtattactgtgcgagaaggtatagttctt atcggagctggttcgatgtctggggccggggagtcctgg tcaccgtctcctca | 46 | tcctctgggctgactcagccacgctcagtgtccgtgtccccag gacagacggccaggatcacctgtggggagacaacattgga agtaaaagtgtgcactggtaccagcagaagccaccgcaggc ccctgtgctggtcatctatgctgatagcgaacggccctcaggg atccctgagcgattctctggctccaactcagggaacaccgcca cccctgaccatcagcggggtcgaggccggggatgaggctgac tattactgtcaggtgtgggacagtagtagtgatcattgggtattc ggaggagggacccgggctgaccgtcctt |
| 42 | QVQLQESGPGLVKPSETLSLTCAVSGFSIS SGYGWSWIRQPPGKGLEWIGYIGGSSGS TSYNPSLKSRVTLSADTSKNQFSLKLSSVT AADTAVYYCARRYSSYRSWFDVWGPGV LVTVSS | 47 | SSGLTQPRSVSVSPGQTARITCGGDNIGSKS VHWYQQKPPQAPVLVIYADSERPSGIPERFS GSNSGNTATLTISGVEAGDEADYYCQVWDS SSDHWVFGGGTRLTVL |
| | FVM06: | | |
| 51 | gaggtgcagctggtgcagtctggagcagaggtgaaaagg cccggggaatctctgacgatctcctgtaagacttctggatac agctttaccaactactggatcagctgggtgcgccagatgcc cggagaaggcctggagtggatggggcgattgatcctagt gattctgataccagatatagccccgtcctccaaggccaggt caccatgtcagccgacaagtccatcaccaccgctacctg cagtggagcagcctgaaggcctcggacactgccacgtatt actgtgtgaaaggaagtgagacctggggccagggagtcc tggtcaccgtctcctca | 56 | cagcctgtgctgactcagccggcctccctctcagcatctcctg gagcatcagccagtctcacatgtaccttcagcggtggcatcaa tgttgctggctacaacatactctggtaccagcagaaggcaggg agtcctcccccggtatcttctgaggtacaaatcagactcaactaa ggaccaggtctgagtccccagccgcttctctggatccaa agatgcttcagcgaacacaggaattttacgcatctctgggctcc agtctgaggatgaggctgactattactgtgccattgggcacag cagcggttggatattcggaggagggacccggctcaccgtcct c |
| 52 | EVQLVQSGAEVKRPGESLTISCKTSGYSF TNYWISWVRQMPGEGLEWMGAIDPSDS DTRYSPSFQGQVTMSADKSITTAYLQWSS LKASDTATYYCVKGSETWGQGVLVTVSS | 57 | QPVLTQPASLSASPGASASLTCTFSGGINVA GYNILWYQQKAGSPPRYLLRYKSDSTKDQ GSGVPSRFSGSKDASANTGILRISGLSEDEA DYYCAIGHSSGWIFGGGTRLTVL |

TABLE 2-continued

Macaque Antibody VH and VL Sequences

| SEQ ID | Heavy Chain / Heavy Chain Variable region | SEQ ID | Light Chain / Light Chain variable region |
|---|---|---|---|
| | FVM07: | | |
| 61 | Gaggtgcagctggtgcagtctggagcagaggtgaaaag gcccggggaatctctgacgatctcctgtaagacttctggata tagttttaccgacagctggatcggctgggtgcgcagatgc ccgggaaaggcctagagtggatggggagcatctatcctg gtgattctgataccaaatacaacccgtccttccaaggccac gtcactatctcagccgacaagtccatcagcaccacctacct gcagtggagcagcctgaaggcctcggacactgccacgta ttactgtgtggctcgtgaagcctactgggccagggagtcc tggtcaccgtctcctca | 66 | Cagcctgtgctgactcagccagcctccctctcagcatctcctg gagcatcagccagtctcacatgcaccttcagcggtggcatcaa tgttgctggctaccacatattctggtaccagcagaagccaggg agtcctcccggtatcttctgaggtacaaatcagactcagataa gggccagggctctggagtccccagccgcttctctggatccaa agatgcttcagcgaacacaggattttacgcatctctgggctcc agtctgaggatgaggctgactattactgtgccattgggcacag cagcggcgtgttattcggaggagggacccggctgaccgtcct c |
| 62 | EVQLVQSGAEVKRPGESLTISCKTSGYSF TDSWIGWVRQMPGKGLEWMGSIYPGDS DTKYNPSFQGHVTISADKSISTTYLQWSS LKASDTATYYCVAREAYWGQGVLVTVS S<br>SEQ ID NO: 62; | 67 | QPVLTQPASLSASPGASASLTCTFSGGINVA GYHIFWYQQKPGSPPRYLLRYKSDSDKGQG SGVPSRFSGSKDASANTGILRISGLQSEDAD YYCAIGHSSGVLFGGGTRLTVL<br>SEQ ID NO: 67 |
| | FVM08: | | |
| 71 | gaggtgcagctggtgcagtctggagcagaggtgaaaagg cccggggaatctctgacgatctcctgtaagacttctggatac agctttaccgacagctgggtcgcctgggtgcgccagatgc ccgggaaaggcctgagtggatggggagtatctatcctgg tgattctgataccagatacaacccgtccttcgaaggccagg tcactatctcagccgacaagtccatcagcaccacctaccta cagtggagtagcctgagggcctcggacactgccacgtatt actgtgtgaaaggtgcggacgactggggccagggagtcc tggtcaccgtctcctca | 76 | cagcctgtgctgactcagccagcctccctctcagcatctcctgg agcatcagccagtctcacatgtaccttcagcggtggcatcaat gttgctggctacaacatactctggtaccagcagaaggcaggg agtcctcccggtatcttctgaggtacaaatcagactcaactaa ggaccagggctctggagtccccagccgcttctctggatccaa agatgcttcagcgaacacaggattttacgcatctctgggctcc agtctgaggatgaggctgactattactgtgccattgggcacag cagcggttggatattcggaggagggacccggctgaccgtcct c |
| 72 | EVQLVQSGAEVKRPGESLTISCKTSGYSF TDSWVAWVRQMPGKGLEWMGSIYPGDS DTRYNPSFEGQVTISADKSISTTYLQWSSL RASDTATYYCVKGADDWGQGVLVTVSS | 57 | QPVLTQPASLSASPGASASLTCTFSGGINVA GYNILWYQQKAGSPPRYLLRYKSDSTKDQG SGVPSRFSGSKDASANTGILRISGLQSEDEAD YYCAIGHSSGWIFGGGTRLTVL |
| | FVM09: | | |
| 81 | gaggtgcagctggtgcagtctggggcagaggtgaaaagg cccggggaatctctgacgatctcctgtaagacttctggatac agctttaccgacagctgggtcgcctgggtgcgccagatgc ccgggaaagggctgagtggttggggagcatctatcctgg tgattctgaaacgaaatacaacccgtccttccaaggccacg tcactatctcagccgacaagtccgtcaccacctactg aagtggagcagcctgaaggcctcggacactgccacgtatt actgtgtgaaaggaagtgagacctggggccagggagtcc tggtcaccgtctcctca | 86 | Cagcttgtgctgactcagccagcctccctctcagcatctcctg gagcatcagccagtctcacatgtaccttcagcggtggcatcaa tgttgctggctacaacatactctggtaccagcagaaggcaggg agtcctcccggtatcttctgaggtacaaatcagactcaactaa ggaccagggctctggagtccccagccgcttctctggatccaa agatgcttcagcgaacacaggattttacgcatctctgggctcc agtctgaggatgaggctgactattactgtgccattgggcacag cagcggttggatattcggaggagggacccggctgaccgtcct c |
| 82 | EVQLVQSGAEVKRPGESLTISCKTSGYSF TDSWVAWVRQMPGKGLEWLGSIYPGDS ETKYNPSFQGHVTISADKSVTTTYLKWSS LKASDTATYYCVKGSETWGQGVLVTVSS | 87 | QLVLTQPASLSASPGASASLTCTFSGGINVA GYNILWYQQKAGSPPRYLLRYKSDSTKDQ GSGVPSRFSGSKDASANTGILRISGLQSEDEA DYYCAIGHSSGWIFGGGTRLTVL |
| | FVM10: | | |
| 91 | caggtgcagctggtgcaatctggagcagaggtgaaaaggcccg gggagtctctgaagatctcctgtcagactcagacgcttt accgacagctgggtcgcctgggtgcgccagatgcccgggaagg gctggagtggttggggagcatctatcctggtgattctgaaacga aatacaaccgtccttccaaggccacgtcactatctcagccgac aagtccatcaccgcctacctgcagtggagcagcctgaaggc ctcggacactgccacgtattactgtgcgaaaggaagtgagacct ggggccaagggctcagggtcaccgtctcttca | 96 | caggcagggctgactcagccggcctccctctcagcatctcctg gagcatcagccagtctacagactgcctccagcggtggcatcaa tgttgctggctataacatactctggtaccagcagaagccaggg agtcctcccggtatcttctgaggtacaaatcagactcagataa ggaccagggctctggagtccccagccgcttctctggatccaa agatgcttcggcaacacaggattttacgcatctctggcctcc agtctgaggatgaggctgactattactgtgccattgggcacag cagcggttggatattcggaggagggacccggctgaccgtcct t |
| 92 | QVQLVQSGAEVKRPGESLKISCQTSGYSF TDSWVAWVRQMPGKGLEWLGSIYPGDS ETKYNPSFQGHVTISADKSISTAYLQWSS LKASDTATYYCAKGSETWGQGLRVTVSS | 97 | QAGLTQPASLSASPGASASLTCTFSGGINVA GYNILWYQQKPGSPPRYLLRYKSDSDKDQG SGVPSRFSGSKDASANTGILRISGLQSEDAD YYCAIGHSSGWIFGGGTRLTVL |
| | FVM11: | | |
| 101 | gaggtgcagctggtgcagtctggagcagaggtgaaaagg cccggggaatctctgacgatctcctgtaagacttctggatac | 106 | aatttatgctgactcagccagcctccctctcagcatctcctgga gcatcagccagtctcacatgtaccttcagcggtggcatcaatgt |

TABLE 2-continued

Macaque Antibody VH and VL Sequences

| SEQ ID | Heavy Chain / Heavy Chain Variable region | SEQ ID | Light Chain / Light Chain variable region |
|---|---|---|---|
| | agctttaccgacagctgggtcgcctgggtgcgccagatgc ccggggaagggctggagtggttggggagcatctatcctgg tgattctgaaacgaaatacaacccgtccttccaaggccacg tcactatctcagccgacaagtccgtcaccaccacctacctg aagtggagcagcctgaaggcctcggacactgccacgtatt actgtgtgaaaggaagtgagacctggggccagggagtcc tggtcaccgtctcctca | | tgctggctacaacatactctggtaccagcagaaggcagggag tcctccccggtatcttctgaggtacaaatcagactcaactaagg accagggctctggagtccccagccgcttctctggatccaaaga tgcttcagcgaacacaggaatttttacgcatctctgggctccagt ctgaggatgaggctgactattactgtgccattgggcacagca cggttggatattcggaggagggacccggctcaccgtcctc |
| 82 | EVQLVQSGAEVKRPGESLTISCKTSGYSF TDSWVAWVRQMPGKGLEWLGSIYPGDS ETKYNPSFQGHVTISADKSVTTTYLKWSS LKASDTATYYCVKGSETWGQGVLVTVSS | 107 | NFMLTQPASLSASPGASASLTCTFSGGINVA GYNILWYQQKAGSPPRYLLRYKSDSTKDQ GSGVPSRFSGSKDASANTGILRISGLQSEDEA DYYCAIGHSSGWIFGGGTRLTVL |

FVM12:

| 111 | gaggtgcagctggtgcagtctggagcagaggtgaaaagg cccggggaatctctgacgatctcctgtaagacttctgaatac agctttaccggcagctggatcagctgggtgcgccagatgc ccggggaaggcctggagtggatggggagcatctatcctg gtgattctgataccagatacagcccgtccttccaaggccag gtcaccatctcagccgacaagtccgtcaccaccacctacct gaagtggagcagcctgaaggcctcggacactgccacgta ttactgtgtgaaaggaagtgagacctggggccagggagtc ctggtcaccgtctcctca | 116 | cagcctgtgctgactcagccggcctccctctcagcatctcttgg agcatcagccagtctcacatgcaccttcagcggtggcatcaat gttgctggctacaacatattgtggtaccagcagaagccaggga gtcctccccggtttcttctgaggtacaaatcagactcagataac gtccagggctctggagtccccagccacttctctggatccaaag atgcttcaacgaacacaggaatttttacgcatctctgggctccag tctgaggatgaggctgactattactgtgccattggcacagca gcggttgggtattcggaggagggacccggctgaccgtcctc |
| 112 | EVQLVQSGAEVKRPGESLTISCKTSEYSFT GSWISWVRQMPGKGLEWMGSIYPGDSD TRYSPSFQGQVTISADKSVTTTYLKWSSL KASDTATYYCVKGSETWGQGVLVTVSS | 117 | QPVLTQPASLSASLGASASLTCTFSGGINVA GYNILWYQQKPGSPPRFLLRYKSDSDNVQG SGVPSHFSGSKDASTNTGILRISGLQSEDAD YYCAIGHSSGWVFGGGTRLTVL |

FVM13:

| 121 | Gaggtgcagctggtgcagtctggagcagaggtgaaaag gcccggggagtctctgaagatctcctgtaagacttctggat acacctttaccagcagctggatcagctgggtgcgccagat gcccggggaaggcctggagtggttggggagcatctatcct ggtgattctgatacgagatacaaaccgtccttccaaggcca cgtcactatctcagccgacacgtccatcatcaccacccacc tgcagtggagcagcctgaaggcctcggacactgccacgt attactgtgtgaaaggaagtgagacctggggccagggagt cctggtcaccgtctcctca | 126 | Aagcctatgctgactcagccaacctccctctcagcatctcctg gagcatcagccagtctcacatgtaccttcagcggtggcatcaa tgttgctggctacaacatactctggtaccagcagaaggcaggg agtcctccccggtatcttctgaggtacaaatcagactcaactaa ggaccagggctctggagtccccagccgcttctctggatccaa agatgcttcagcgaacacaggaatttttacgcatctctgggctcc agtctgaggatgaggctgactattactgtgccattgggcacag cagcggttggatattcggaggagggacccggctgaccgtcct c |
| 122 | EVQLVQSGAEVKRPGESLKISCKTSGYTF TSSWISWVRQMPGKGLEWLGSIYPGDSD TRYNPSFQGHVTISADTSIITTHLQWSSLK ASDTATYYCVKGSETWGQGVLVTVSS | 127 | KPMLTQPTSLSASPGASASLTCTFSGGINVA GYNILWYQQKAGSPPRYLLRYKSDSTKDQ GSGVPSRFSGSKDASANTGILRISGLQSEDEA DYYCAIGHSSGWIFGGGTRLTVL |

FVM14:

| 131 | gaggtgcagctggtgcagtctggagcagaggtgaaaagg cccggggagtctctgaagatctcctgtcagacttctggatac agctttaccagcacctggatcacctgggtgcgccagatgc ccggggaaagggctggagtggttggggagcatctatcctgg tgattctgaaacgaaatacaacccgtccttccaaggccacg tcaccatttcagccgacaagtccatcagcaccaccacctg cagtggaacagcctgaaggcctcggacactgccacgtatt actgtgtgaaaggaagtgagacctggggccagggagtcc tggtcaccgtctcctca | 136 | caggctgtggtgactcagccagcctccctctcagcatctcctg gagcatcagccagtctcacatgtaccttcagcggtggcatcaa tgttgctggctacaacatactctggtaccagcagaaggcaggg agtcctccccggtatcttctgaggtacaaatcagactcaactaa ggaccagggctctggagtccccagccgcttctctggatccaa agatgcttcagcgaacacaggaatttttacgcatctctgggctcc agtctgaggatgaggctgactattactgtgccattgggcacag cagcggttggatattcggaggagggacccggctgaccgtcct c |
| 132 | EVQLVQSGAEVKRPGESLKISCQTSGYSF TSTWITWVRQMPGKGLEWLGSIYPGDSE TKYNPSFQGHVTISADKSISTTYLQWNSL KASDTATYYCVKGSETWGQGVLVTVSS | 137 | QAVVTQPASLSASPGASASLTCTFSGGINVA GYNILWYQQKAGSPPRYLLRYKSDSTKDQ GSGVPSRFSGSKDASANTGILRISGLQSEDEA DYYCAIGHSSGWIFGGGTRLTVL |

FVM15:

| 141 | caggtgcagctggtgcagtctggagcagaggtgaaaagg cccggggaatctctgaggatctcctgtaagacttctggatac accttaccgactactggatcgcctgggtgcgccagatgcc cggaaagggcctggagtggtggggagcatctatcctggt gattctgaaacgaaatacaacccgtccttccaaggccacgt cactatctcagccgacaagtccgtcaccaccacctacctga agtggagccgcctgaaggcctcggacactgccacgtatta ctgtgtgaaaggaagtgagacctggggccagggagtcct ggtcaccgtctcctca | 146 | cagcctgtgctgactcagccagcctccctctcagcatctcctggagca tcagccagtctcacatgtaccttcagcggtggcatcaatgttgctggct acaacatactctggtaccagcagaaggcagggagtcctcccggtat cttctgaggtacaaatcagaccagggctccccagccgcttctctggat ccaaagatgcttcagcgaacacaggaatttttacgcatctctgggctccagtctgaggatgaggctgactattactgt gccattgggcacagcagcggttggatattcggaggagggacccgg ctgaccgtcctc |

TABLE 2-continued

Macaque Antibody VH and VL Sequences

| SEQ ID | Heavy Chain / Heavy Chain Variable region | SEQ ID | Light Chain / Light Chain variable region |
|---|---|---|---|
| 142 | QVQLVQSGAEVKRPGESLRISCKTSGYTFTDYWIAWVRQMPGKGLEWMGSIYPGDSETKYNPSFQGHVTISADKSVTTTYLKWSRLKASDTATYYCVKGSETWGQGVLVTVSS | 57 | QPVLTQPASLSASPGASASLTCTFSGGINVAGYNILWYQQKAGSPPRYLLRYKSDSTKDQGSGVPSRFSGSKDASANTGILRISGLQSEDEADYYCAIGHSSGWIFGGGTRLTVL<br>SEQ ID NO: 57 |

FVM16:

| 151 | gaggtgcagctggtgcagtctggagcagaggtgaaaaggcccgggggagtctctaaagatctcctgtaggacttctggatacagctttaccagtacctggtcagctgggtgcgccagatgcccgggaaaggcctggagtggttgggagcatctatcctggtgattctgaaacgaaatacaacccgtccttccaaggccacgtcactatctcagccgacaagtccgtcaccaccacctacctgaagtggagcagctgaaggcctcggacactgccacgtattactgtgtgaaaggaagtgagacctggggccagggagtcctggtcaccgtctcctca | 156 | aagcctatgctgactcagccagcctccctctcagcatctcctggagcatcagccagtctcacatgtaccttcagcggtggcatcaatgttgctggctacaacatactctggtaccagcagaaggcagggagtcctccccggtatcttctgaggtacaaatcagactcaactaaggaccagggctctggagtcccagccgcttctctggatccaaagatgcttcagcgaacacaggaattttacgcatctctgggctccagtctgaggatgaggctgactattactgtgccattgggcacagcagcggttgggtcttcggaggagggacccggctgaccgtcct |
| 152 | EVQLVQSGAEVKRPGESLKISCRTSGYSFTSTWINWVRQMPGKGLEWLGSIYPGDSETKYNPSFQGHVTISADKSVTTTYLKWSSLKASDTATYYCVKGSETWGQGVLVTVSS | 157 | KPMLTQPASLSASPGASASLTCTFSGGINVAGYNILWYQQKAGSPPRYLLRYKSDSTKDQGSGVPSRFSGSKDASANTGILRISGLQSEDEADYYCAIGHSSGWVFGGGTRLTVL |

FVM17:

| 161 | gaggtgcagctggtgcagtctggagcagaggtgaaaaggcccgggggaatctctgacgatctcctgtaagacttctggatacagttttaccgacagctggatcagctgggtgcgccagatgcccgggaaaggcctggagtggatgggagcatctatcctggtgattctgatgccagatacaacccgtccttccaaggccacgtcactatctcggccgacaagtccatcagcaccacctacctgaagtggagcagctgaaggcctcggacactgccacgtattactgtgtgaaaggaagtgagacctggggccagggagtcctggtcaccgtctcctca | 166 | caggctgtggtgactcagccagcctccctctcagcatctcctggaacatcagccagtctcacatgcaccttcagcggtggcatcaatgttgctggctacaacatattgtggtaccagcagaagccagggagtcctccccggtttcttctgaggtacaaatcagactcagataacgtccagggctctggagtcccagccacttctctggatccaaagatgcttcagcgaacacagggatcttacgcatctctgggctccagtctgaggatgaggctgactattactgtgccattgggcacagcagcggttggatattcggaggagggacccggctgaccgtcct |
| 162 | EVQLVQSGAEVKRPGESLTISCKTSGYSFTDSWISWVRQMPGKGLEWMGSIYPGDSDARYNPSFQGHVTISADKSISTTYLKWSSLKASDTATYYCVKGSETWGQGVLVTVSS | 167 | QAVVTQPASLSASPGTSASLTCTFSGGINVAGYNILWYQQKPGSPPRFLLRYKSDSDNVQGSGVPSHFSGSKDASANTGILRISGLQSEDEADYYCAIGHSSGWIFGGGTRLTVL |

FVM18:

| 171 | caggtgcagctggtgcaatctggagcagaggtgaaaaggcccgggggagtctctgaagatctctgtaagacttctggatacagctttaccaacatctggatcagttgggtgcgccagatgcccgggaaagggctggagtggttgggagcatctatcctggtgattctgaaacgaaatacaacccgtccttccaaggccacgtcactatctcagccgacaagtccgtcaccaccacctacctgaagtggagcagctgaaggcctcggacactgccacgtattactgtgtgaaaggaagtgagacctggggccagggagtcctggtcaccgtctcctca | 176 | aattttatgctgactcagccggcctccctctcagcatctcctggagcatcagccagtctcacatgcacggtggcatcaatgttgctggctaccacatattgtggtatcagcagagaagccagggagtcctccccggtatcttctgaggtataaatcagactcagagaaggaccagggctctggagtcccagccgcttctctggatccaaagatgcttcggccaacagagggattttacgcatctctgggctccagtctgaagatgaggctgactattactgtgccattgggcacagtagtagcggttgggtattcggaggagggacccggctgaccgtcctc |
| 172 | QVQLVQSGAEVKRPGESLKISCKTSGYSFTNIWISWVRQMPGKGLEWLGSIYPGDSETKYNPSFQGHVTISADKSVTTTYLKWSSLKASDTATYYCVKGSETWGQGVLVTVSS | 177 | NFMLTQPASLSASPGASASLTCTFSGGINVAGYHILWYQQKPGSPPRYLLRYKSDSEKDQGSGVPSRFSGSKDASANRGILRISGLQSEDEADYYCAIGHSSSGWVFGGGTRLTVL |

FVM19:

| 181 | caggtgcagctggtgcagtctggagcagaggtgaaaaggcccgggggaatctctgacgatctcctgtaagacttctggatacagctttaccgacagctgggtcgcctgggtgcgccagatgcccgggaaagggctggagtggttgggagcatctatcctggtgattctgataccaaatacaacccgtccttccaaggccacgtcactatctcagccgacaagtccgtcaccaccacctacctgaagtggagcagctgaaggcctcggacactgccacgtattactgtgtgaaaggaagtgagacctggggccagggagtcctggtcaccgtctcctca | 186 | aagcctatgctgactcagccagcctccctctcagcatctcctggagcatcagccagtctcacatgcaccttcagcggtggcatcaatgttgctggctaccacatattgtggtaccagcagaagccagggagtcctccccggtatcttctgaggtataaatcagactcagataagggccagggctctggagtcccagccgcttctctggatccaaagatgcttcagcgaacacagggattttacgcatctctgggctccagtctgaggatgaggctgactattactgtgccattgggcacagcagcggtctgttattcggaggagggacccggctgaccgtcctc |
| 182 | QVQLVQSGAEVKRPGESLTISCKTSGYSFTDSWVAWVRQMPGKGLEWLGSIYPGDSDTKYNPSFQGHVTISADKSVTTTYLKWSSLKASDTATYYCVKGSETWGQGVLVTVSS | 187 | KPMLTQPASLSASPGASASLTCTFSGGINVAGYHIFWYQQKPGSPPRYLLRYKSDSDKQGSGVPSRFSGSKDASANTGILRISGLQSEDEADYYCAIGHSSGLLFGGGTRLTVL |

TABLE 2-continued

Macaque Antibody VH and VL Sequences

| SEQ ID | Heavy Chain<br>Heavy Chain Variable region | SEQ ID | Light Chain<br>Light Chain variable region |
|---|---|---|---|
| | FVM20: | | |
| 191 | Gaggtgcagttggtggagtctggagcagaggtgaaaagg cccggggagtctctgacgatctcctgtaagacttctggatac agctttaccggcagctggatcagctgggtgcgccagatgc ccgggaaaggcctggagtggttggggagcatctatcctgg tgattctgaaacgaaatacaacccgtccttccaaggccacg tcactatctcagccgacaagtccgtcaccaccacctacctg aagtggagcagcctgaaggcctcggacactgccacgtatt actgtgtgaaaggaagtgagacctggggccagggagtcc tggtcaccgtctcctca | 196 | aatttttatgctgactcagtcggcctccctctcagcatctcctgga gcatcagccagtctcacatgcaccttcagcggtggcatcaatg ttgctggctaccacatattctggtaccagcagaacccagggag tcctccccgctatcttctgagatacaaatcagactcagagaagg accagggctctggagtccccagccgcttctctggatccaaaga tgcttcagcgaacacaggaattttacgcatctctggatccagt ctgaggatgaggctgactattactgtgccattgggcacag cggttggatattcggaggagggacccggctcaccgtcctc |
| 192 | EVQLVESGAEVKRPGESLTISCKTSGYSFT GSWISWVRQMPKGLEWLGSIYPGDSET KYNPSFQGHVTISADKSVTTTYLKWSSLK ASDTATYYCVKGSETWGQGVLVTVSS | 197 | NFMLTQSASLSASPGASASLTCTFSGGINVA GYHIFWYQQNPGSPPRYLLRYKSDSEKDQG SGVPSRFSGSKDASANTGILRISGLQSEDAD YYCAIGHSSGWIFGGGTRLTVL |
| | FVM21: | | |
| 201 | gaggtgcagttggtggagtctggagcagaggtgaaaagg cccggggaatctctgacgatctcctgtaagacttctggatac agctttaccgacagctgggtcgcctgggtgcgccagatgc ccgggaaagggctggagtggttggggagcatctatcctgg tgattctgaaacgaaatacaacccgtccttccaaggccacg tcactatctcagccgacaagtccatcagcaccaccacctacta cagtggagtagcctgagggcctcggacactgccacgtatt actgtgtgaaaggtgcggacgactggggcccaggactcct ggtcaccgtctcctca | 206 | tcctctgagctgactcagccagcctccctctcagcatctcctgg agcatcagccagtctcacatgtaccttcagcggtggcatcaat gttgctggctacaacatactctggtaccagcagaaggcaggg agtcctccccggtatcttctgaggtacaaatcagactcagataa gggccagggctctggagtccccagccgcttctctggatccaa agatgcttcagcgaacacagggattttacgcatctctgggtcc agtctgaggatgaggctgactattactgtgccattgggcacag cagcggttggatattcggaggagggacccggctcaccgtcct c |
| 202 | EVQLVESGAEVKRPGESLTISCKTSGYSFT DSWVAWVRQMPKGLEWLGSIYPGDSE TKYNPSFQGHVTISADKSISTTYLQWSSLR ASDTATYYCVKGADDWGPGLLVTVSS | 207 | SSELTQPASLSASPGASASLTCTFSGGINVA GYNILWYQQKAGSPPRYLLRYKSDSDKGQ GSGVPSRFSGSKDASANTGILRISGLQSEDA DYYCAIGHSSGWIFGGGTRLTVL |
| | FVM22: | | |
| 211 | gaggtgcagctggtgcagtctggagcagaggtgaaaagg cccggggaatctctgacgatctcctgtaagacttctggatac agctttaccgacagctgggtcgcctgggtgcgccagatgc ccgggaaagggctggagtggttggggagcatctatcctgg tgattctgaaacgaaatacaacccgtccttccaaggccacg tcactatctcagccgacaagtccatcagcaccgcctacctg cagtggagcagcctgaaggcctcggacaccgccacctatt actgtgcgaaaggaagtgagacctggggccagggagtcc tggtcaccgtctcctca | 216 | tcctccgggctgactcagccagcctccctctcagcatctcctgg agcatcagccagtctcacatgtaccttcagcggtggcatcaat gttgctggctacaacatactctggtaccaacagaaggcaggg agtcctccccggtatcttctgaggtacaaatcagactcaactaa ggaccagggctctggagtccccagccgcttctctggatccaa agatgcttcagcgaatacaggaattttacgcatctctgggctcc agtctgaggatgaggctgactattactgtgccattgggcacag cagcggttggatattcggaggagggacccggctaccgtcct c |
| 212 | EVQLVQSGAEVKRPGESLTISCKTSGYSF TDSWVAWVRQMPKGLEWLGSIYPGDS ETKYNPSFQGHVTISADKSISTAYLQWSS LKASDTATYYCAKGSETWGQGVLVTVSS | 217 | SSGLTQPASLSASPGASASLTCTFSGGINVA GYNILWYQQKAGSPPRYLLRYKSDSTKDQ GSGVPSRFSGSKDASANTGILRISGLQSEDA DYYCAIGHSSGWIFGGGTRLTVL |
| | FVM23: | | |
| 221 | caggtgcagctggtgcagtctggagcagaggtgaaaagg cccggggaatctctgacgatctcctgtaagacttctggatac agctttaccggcagctggatcagctgggtgcgccagatgc ccgggaaaggcctggagtggatggggagcatctatcctg gtgattctgataccacataccgtccttccaaggccacg tcactatctcagccacaagtccatcagtaccgcctacctg caatgactagtctgaaggcctcggacactgccacgtatta ctgtgtgaaaggaagtgagacctggggccagggagtcct ggtcaccgtctcctca | 226 | tcctatgagctgacacagccagcctccctctcagcatctcctgg agcatcagccagtctcacatgtaccttcagcggtggcatcaat gttgctggctacaacatactctggtaccagcagaaggcaggg agtcctccccggtatcttctgaggtacaaatcagactcaactaa ggaccagggctctggagtccccagccgcttctctggatccaa agatgcttcagcgaacacaggatcttacgcatctctggcctc cagtctgaggatgaggctgactattactgtgccattggccaca gcagcggtctcatcttcggtgctgggaccggctcaccgtcct c |
| 222 | QVQLVQSGAEVKRPGESLTISCKTSGYSF TGSWISWVRQMPKGLEWMGSIYPGDS DTTYNPSFQGHVTISADKSISTAYLQWTS LKASDTATYYCVKGSETWGQGVLVTVSS | 227 | SYELTQPASLSASPGASASLTCTFSGGINVA GYNILWYQQKAGSPPRYLLRYKSDSTKDQ GSGVPSRFSGSKDASANTGILRISGLQSEDA DYYCAIGHSSGLIFGAGTRLTVL |
| | FVM24: | | |
| 231 | gaggtgcagctggtgcagtctggagcagaggtgaaaagg cccggggagtctctgaagatctcctgtaagacttctggatac agctttaccgacagctgggtcgcctgggtgcgccagatgc ccgggaaaggcctggaatggatggggagcatctatcctgg tgattttcaaacgagatacaacccgtccttccaaggacac | 236 | tcctccgggctgactcagccagcctccctctcagcatctcctgg agcatcagccagtctcacatgtaccttcagcggtggcatcaat gttgctggctacaacatactctggtaccagcagaaggcaggg agtcctccccggtatcttctgaggtacaaatcagactcaactaa ggaccagggctctggagtccccagccgcttctctggatccaa |

TABLE 2-continued

Macaque Antibody VH and VL Sequences

| SEQ ID | Heavy Chain / Heavy Chain Variable region | SEQ ID | Light Chain / Light Chain variable region |
|---|---|---|---|
| | gtcactctctcagccgacaagtccatcagcaccacctacct<br>acagtggagcagcctgaaggcctcggacaccgccacgta<br>ttactgtgtgaaaggaagtgagacctggggcccggggagtc<br>ctggtcaccgtctcctca | | agatgtttcagcgaacacaggcatcttacgcatctctgggctcc<br>agtctgacgatgaggctgactattactgtgccattgggcacag<br>cagcggttggatattcggaggcgggacccggctgaccgtcct<br>c |
| 232 | EVQLVQSGAEVKRPGESLKISCKTSGYSF<br>TDSWVAWVRQMPGKGLEWMGSIYPGD<br>FQTRYNPSFQGHVTLSADKSISTTYLQWS<br>SLKASDTATYYCVKGSETWGPGVLVTVS<br>S | 237 | SSGLTQPASLSASPGASASLTCTFSGGINVA<br>GYNILWYQQKAGSPPRYLLRYKSDSTKDQ<br>GSGVPSRFSGSKDVSANTGILRISGLQSDDE<br>ADYYCAIGHSSGWIFGGGTRLTVL |

FVM25:

| 241 | gaggtgcagctggtgcattctggagcagaggtgaaaagg<br>cccggggaatctctgacgatctcctgtaagacttctggatac<br>accttttaccgactactgatcgcctgggtgcgccagatgcc<br>cgggaaaggggctggagtggatggcgagcatctatcctgat<br>gattctgataccagatacaacccgtccttccaaggccacgt<br>cactatctcagccgacaagtccatcagcaccacctacctac<br>agtggagtagcctgagggcctcggacactgccacgtatta<br>ctgtgtgaaaggaagtgagacctggggccaggggagtcct<br>ggtcaccgtctcctca | 246 | cagcttgtgctgactcagccagcctccctctcagcatctcctgg<br>aacatcagccagtctcacatgtgcccttcagcggtggcatcaat<br>gttggctacaacatattgtggtaccagcagaagccaggga<br>gtcctcccggttttcttctgaggtacaaatcagactcagataac<br>gtccagggctctggagtccccagccacttctctggatccaaag<br>atgcttcaacgaacacagggattttacgcatctctgggctccag<br>tctgaggatgaggctgactattactgtgccattggcacagca<br>gcggttgggtattcggaggagggacccggctgaccgtcctc |
| 242 | EVQLVHSGAEVKRPGESLTISCKTSGYTF<br>TDYWIAWVRQMPGKGLEWMASIYPDDS<br>DTRYNPSFQGHVTISADKSISTTYLQWSSL<br>RASDTATYYCVKGSETWGQGVLVTVSS | 247 | QLVLTQPASLSASPGTSASLTCTFSGGINVA<br>GYNILWYQQKPGSPPRFLLRYKSDSDNVQG<br>SGVPSHFSGSKDASTNTGILRISGLQSEDEAD<br>YYCAIGHSSGWVFGGGTRLTVL |

FVM26:

| 251 | caggtgcagctggtgcagtctggagcagaggtgaaaagg<br>cccggggaatctctgaggatctcctgtaagacttctggatac<br>accttttaccgactactgatcgcctgggtgcgccagatgcc<br>cggaaaaggcctggagtggatggggagcatctatcctggt<br>gattctgaaacgaaatacaacccgtccttccaaggccacgt<br>cactatctcagccgacaagtccgtcaccaccacctacctga<br>gtggagccgcctgaaggcctcggacactgccacgtatta<br>ctgtgtgaaaggaagtgagacctggggccaggggagtcct<br>ggtcaccgtctcctca | 256 | cagcctgtgctgactcagccagcctccctctcagcatctcctgg<br>agcatcagccagtctcacatgtaccttcagcggtggcatcaat<br>gttggctacaacatattgtggtaccagcagaaggcaggg<br>agtcctcccggtatcttctgaggtacaaatcagactcaactaa<br>ggaccagggctctggagtccccagccgcttctctggatccaaa<br>agatgcttcagcgaacacaggaattttacgcatctctgggctcc<br>agtctgaggatgaggctgactattactgtgccattgggcacag<br>cagcggttggatattcggaggagggacccggctgaccgtcct<br>c |
| 142 | QVQLVQSGAEVKRPGESLRISCKTSGYTF<br>TDYWIAWVRQMPGKGLEWMGSIYPGDS<br>ETKYNPSFQGHVTISADKSVTTTYLKWSR<br>LKASDTATYYCVKGSETWGQGVLVTVSS | 57 | QPVLTQPASLSASPGASASLTCTFSGGINVA<br>GYNILWYQQKAGSPPRYLLRYKSDSTKDQG<br>SGVPSRFSGSKDASANTGILRISGLQSEDEAD<br>YYCAIGHSSGWIFGGGTRLTVL |

FVM27:

| 261 | gaggtgcagctggtgcagtctggagcagaggtgaaaagg<br>cccggggagtctctgaagatctcctgtaagacttctggatac<br>agctttgccagcagttggatcagctgggtgcgccagatgc<br>ccgggaaaggcctggagtggatgggggcgattgatccta<br>gtgattctgctaccagatacagcccgtccttccaaggccag<br>gtcactatctcagccgacaagtccatcagtaccgcctacct<br>gcagtggagcagcctgaaggcctcggacactgccacgta<br>ttactgtgtgaaaggaagtgagacctggggccagggagtc<br>ctggtcaccgtctcctca | 266 | cagcctgtgctgactcagccggcctccctctcagcttctcctgg<br>agcatcagccagtctcacatgtaccttcagcggtggcatcaat<br>gttgctggctacaacatactctggtaccagcagaaggcaggg<br>agtcctcccggtatcttctgaggtacaaatcagactcaactaa<br>ggaccagggctctggagtccccagccgcttctctggatccaa<br>agatgcttcagcgaacacaggaattttacgcatctctgggctcc<br>agtctgaggatgaggctgactattactgtgccattgggcacag<br>cagcggttggatattcggaggagggacccgcctgaccgtcct<br>a |
| 262 | EVQLVQSGAEVKRPGESLKISCKTSGYSF<br>ASSWISWVRQMPGKGLEWMGAIDPSDS<br>ATRYSPSFQGVTISADKSISTAYLQWSSL<br>KASDTATYYCVKGSETWGQGVLVTVSS | 267 | QPVLTQPASLSASPGASASLTCTFSGGINVA<br>GYNILWYQQKAGSPPRYLLRYKSDSTKDQ<br>GSGVPSRFSGSKDASANTGILRISGLQSEDEA<br>DYYCAIGHSSGWIFGGGTRLIVL |

FVM28:

| 271 | gaggtgcagctggtgcagtctggagcagaggtgaaaagg<br>cccggggagtctctgaagatctcctgtcagacttctggatac<br>aggtttaccagcagctggatcagctgggtgcgccagatgc<br>ccgggaaaggcctggagtggatggggggcaattgatccta<br>gtgattctgagaccagatacagcccgtccttccaaggccag<br>gtcaccatctcagccgacaagtccatcagcaccgcctacct<br>gaagtggagcagcctgaaggcctcggacactgccacgta<br>ttactgtgtgaaaggaagtgagacctggggccagggagtc<br>ctggtcaccgtctcctca | 276 | caggctgccctgactcagccggcctccctctcagcatctcctg<br>gagcatcagccagtctcacatgtgcacttcagcggtggcatcaa<br>tgttgctggctaccacatattgtggtatcagcagaagccaggg<br>agtcctcccggtatcttctgaggtataaatcagactcagagaa<br>ggaccagggctctggagtccccagccgcttctctggatccaa<br>agatgcttcggccaacagagggattttacgcatctctgggctcc<br>agtctgaagatgaggctgactattactgtgccattgggcacagt<br>agtagcggttgggtattcggaggagggacccggctcaccgtc<br>ctc |

TABLE 2-continued

Macaque Antibody VH and VL Sequences

| SEQ ID | Heavy Chain / Heavy Chain Variable region | SEQ ID | Light Chain / Light Chain variable region |
|---|---|---|---|
| 272 | EVQLVQSGAEVKRPGESLKISCQTSGYRF TSSWISWVRQMPGKGLEWMGAIDPSDSE TRYSPSFQGQVTISADKSISTAYLKWSSLK ASDTATYYCVKGSETWGQGVLVTVSS | 277 | QAALTQPASLSASPGASASLTCTFSGGINVA GYHILWYQQKPGSPPRYLLRKSDSEKDQG SGVPSRFSGSKDASANRGILRISGLQSEDAD YYCAIGHSSSGWVFGGGTRLTVL |

FVM29:

| 281 | gaggtgcagctggtgcagtctggagcagaggtgaaaagg cccgggggagtctctgaagatctcctgtcagacttctggaaa cagctttaccaacaactggatcagctgggtgcgcagatg ccccggaaaaggcctggagtggatggggggcgattgatcct agtgattctgaaaccagatacagcccgtcctccaaggcca ggtcaccatctcagccgacaagtccatcaacaccgcctac ctgcagtggagcagcctgaaggcctcggacaccgccacg tattactgtgtgaaaggaagtgagacctggggccagggag tcctggtcaccgtctcctca | 286 | cagcctgtgctgactcagccggcctccctctcagcatctcctg gagcatcagccagtctcacatgtaccttcagcggtggcatcaa tgttgctggctacaacatactctggtaccagcagaaggcaggg agtcctcccccggtatcttctgaggtacaaatcagactcaactaa ggaccagggtctggagtccccagccgcttctctggatccaa agatgcttcagcgaacacaggaattttacgcatctctgggctcc agtctgaggatgaggctgactattactgtgccattgggcacag cagcggttggatattcggaggagggacccggctgaccgtcct c |

| 282 | EVQLVQSGAEVKRPGESLKISCQTSGNSF TNNWISWVRQMPGKGLEWMGAIDPSDS ETRYSPSFQGQVTISADKSINTAYLQWSS LKASDTATYYCVKGSETWGQGVLVTVSS | 57 | QPVLTQPASLSASPGASASLTCTFSGGINVA GYNILWYQQKAGSPPRYLLRYKSDSTKDQG SGVPSRFSGSKDASANTGILRISGLQSEDAD YYCAIGHSSGWIFGGGTRLTVL |

FVM31:

| 291 | caggtgcagctggtgcaatctggagcagaggtgaaaagg cccggggaatctctgacgatctcctgtaagacttctggatac agctttaccgacagctgggtcgcctgggtgcgccagatgc ccgggaaagggctggagtggttgggggagcatctatcctgg tgattctgatgccagatacaacccgtccttccaaggccacgt cactatctcggccgacacgtccgtcaccaccacctacctga agtggagcagcctgaaggcctcggacactgccacgtatta ctgtgtgaaaggaagtgagacctggggccagggagtcct ggtcaccgtctcctca | 296 | aagcctatgctgactcagccagcctccctctcagcatctcctgg agcatcagccagtctcacatgtaccttcagcggtggcatcaat gttgctggctacaacatactctggtaccagcagaaggcaggg agtcctcccccggtatcttctgaggtacaaatcagactcaactaa ggaccagggtctggagtcccccagccgcttctctggatccaa agatgcttcagcgaacacaggaattttacgcatctctgggctcc agtctgaggatgaggctgactattactgtgccattgggcacag cagcggttggatattcggaggagggacccggctgaccgtcct c |

| 292 | QVQLVQSGAEVKRPGESLTISCKTSGYSF TDSWVAVRQMPGKGLEWLGSIYPGDS DARYNPSFQGHVTISADTSVTTTYLKWSS LKASDTATYYCVKGSETWGQGVLVTVSS | 297 | KPMLTQPASLSASPGASASLTCTFSGGINVA GYNILWYQQKAGSPPRYLLRYKSDSTKDQ GSGVPSRFSGSKDASANTGILRISGLQSEDEA DYYCAIGHSSGWIFGGGTRLTVL |

FVM32:

| 301 | caggtgcagctggtgcagtctggagcagaggtgaaaagg cccggggaatctctgaggatctcctgtaagacttctggatac agctttaccgacagctgggtcgcctgggtgcgccagatgc ccgggaaagggctggagtggttgggggagcatctatcctgg tgattctgataccagatacagcccgtccttccaaggccagg tcaccatctcagccgacaagtccatcaccaccgcctactg aagtggagcagcctgaaggcctcggacactgccacgtatt actgtgtgaaaggaagtgagacctggggccagggagtcc tggtcaccgtctcctca | 306 | cagcctgtgctgactcagccggcctccctctcagcatctcctg gagcatcagccagtctcacatgcaccttcaacggtggcatcac tgttcctggctacgacatactctggtaccagcagaagtcaggg agtcctcccccggtatcttctgaggtacaaatcagactcaactaa ggaccagggtctggagtcccccagccgcttctctggatccaa agatgcttcaacgaacacagggattttacgcatctctgggctcc agtctgaggatgaggctgactattactgtgccattgggcacag cagcggttggatattcggaggagggacccggctgaccgtcct c |

| 302 | QVQLVQSGAEVKRPGESLRISCKTSGYSF TDSWVAWVRQMPGKGLEWLGSIYPGDS DTRYSPSFQGQVTISADKSITTAYLKWSSL KASDTATYYCVKGSETWGQGVLVTVSS | 307 | QPVLTQPASLSASPGASASLTCTFNGGITVP GYDILWYQQKSGSPPRYLLRYKSDSTKDQG SGVPSRFSGSKDASTNTGILRISGLQSEDEAD YYCAIGHSSGWIFGGGTRLTVL |

FVM33:

| 311 | caggtgcagctggtgcagtctggggcagaggtgaaaagg cccgggagtctctgaagatctcctgtaagacttctagatac agctttaccagcagctggctgggtgcgccagatgc ccgggaaagggctggagtggttgggggagcatctatcctgg tgattctgataccagatacaacccgtccttccaaggccacgt cactatctcagccgacaagtccgtcaccaccacctacctga agtggagcagcctgaaggcctcggacactgccacgtatta ctgtgtgaaaggaagtgagacctggggccagggagtcct ggtcaccgtctcctca | 316 | cagcctgtgctgactcagccagcctccctctcagcatctcctgg agcatcagccagtctcacatgtaccttcagcggtggcatcaat gttgctggctacaacatactctggtaccagcagaaggcaggg agtcctcccccggtatcttctgaggtacaaatcagactcaactaa ggaccagggtctggagtcccccagccgcttctctggatccaa agatgcttcagcgaacacaggaattttacgcatctctgggctcc agtctgaggatgaggctgactattactgtgccattgggcacag cagcggttggatattcggaggagggacccggctgaccgtcct c |

| 312 | QVQLVQSGAEVKRPGESLKISCKTSRYSF TSSWIGWVRQMPGKGLEWLGSIYPGDSD TRYNPSFQGHVTISADKSVTTTYLKWSSL KASDTATYYCVKGSETWGQGVLVTVSS | 57 | QPVLTQPASLSASPGASASLTCTFSGGINVA GYNILWYQQKAGSPPRYLLRYKSDSTKDQG SGVPSRFSGSKDASANTGILRISGLQSEDAD YYCAIGHSSGWIFGGGTRLTVL SEQ ID NO: 57 |

TABLE 2-continued

Macaque Antibody VH and VL Sequences

| SEQ ID | Heavy Chain<br>Heavy Chain Variable region | SEQ ID | Light Chain<br>Light Chain variable region |
|---|---|---|---|
| | FVM34: | | |
| 321 | gaggtgcagttggtggagtctggagcagaggtgaaaagg<br>cccggggaatctctgacgatctcctgtaagacttctggatac<br>agctttaccgacagctgggtcagctgggtgcgccagatgc<br>ccgggaaaggcctgagtggatggggagcatctatcctg<br>gtgattctgaaacgaaatacaacccgtccttccaaggccac<br>gtcactatctcagccgacaagtccgtcaccaccacctacct<br>gaagtggagcagcctgaaggcctcggacactgccacgta<br>ttactgtgtgaaaggaagtgagacctggggccagggagtc<br>ctggtcaccgtctcctca | 326 | cagcctgtgctgactcagccggcctccctctcagcatctcctggagca<br>tcagccagtctcacatgcaccttcagcggtggcatcaatgttgctggct<br>actacatacactggtaccagcagaagccaggagtcctcccggta<br>ccttctgaggtacaaatcagactcagataagcaccagggctctggag<br>tccccagccgcttctctggatccaaagatgcttcggccaacacaggg<br>attttacgcatctctgggctccagtctgaggatgaggctgactattact<br>gtgccattgggcacagcagcggttgggtattcggaggagggacccg<br>gctgaccgtcctc |
| 322 | EVQLVESGAEVKRPGESLTISCKTSGYSFT<br>DSWVSWVRQMPKGLEWMGSIYPGDSE<br>TKYNPSFQGHVTISADKSVTTTYLKWSSL<br>KASDTATYYCVKGSETWGQGVLVTVSS | 327 | QPVLTQPASLSASPGASASLTCTFSGGINVA<br>GYYIHWYQQKPGSPPRYLLRYKSDSDKHQ<br>GSGVPSRFSGSKDASANTGILRISGLQSEDEA<br>DYYCAIGHSSGWVFGGGTRLTVL |
| | FVM35: | | |
| 331 | Gaggtgcagctggtgcagtctggagcagaggtgaaaag<br>gcccggggaatctctgacgatctcctgtaagacttctggata<br>cagctttaccagctactggatcacctgggtgcgccagatgc<br>ccgggaaagggctgagtggttggggagcatctatcctgg<br>tgattctgaaacgaaatacaaccgtccttccaaggccacg<br>tcactatctcagccgacaagtccgtcaccaccacctactg<br>aagtggagcagcctgaaggcctcggacactgccacgtatt<br>actgtgtgaaaggaagtgagacctggggccagggagtcc<br>tggtcaccgtctcctca | 316 | Cagcctgtgctgactcagccagcctccctctcagcatctcctg<br>gagcatcagccagtctcacatgtaccttcagcggtggcatcaa<br>tgttgctggctacaacatactctggtaccagcagaaggcaggg<br>agtcctcccggtatcttctgaggtacaaatcagactcaactaa<br>ggacagggctctggagtccccagccgcttctctggatccaa<br>agatgcttcagcgaacacaggaattttacgcatctctgggctcc<br>agtctgaggatgaggctgactattactgtgccattgggcacag<br>cagcggtggatattcggaggagggacccggctgaccgtcct<br>c |
| 332 | EVQLVQSGAEVKRPGESLTISCKTSGYSF<br>TSYWITWVRQMPKGLEWLGSIYPGDSE<br>TKYNPSFQGHVTISADKSVTTTYLKWSSL<br>KASDTATYYCVKGSETWGQGVLVTVSS | 57 | QPVLTQPASLSASPGASASLTCTFSGGINVA<br>GYNILWYQQKAGSPPRYLLRYKSDSTKDQG<br>SGVPSRFSGSKDASANTGILRISGLQSEDAD<br>YYCAIGHSSGWIFGGGTRLTVL |
| | FVM36: | | |
| 341 | gaggtgcagctggtgcagtctggagcagaggtgaaaagg<br>cccggggaatctctgacgatctcctgtaagacttctggatac<br>agctttaccgacaactggatcagctgggtgcgccagatgc<br>ccgggaaaggcctgagtggatggggagcatctatcctg<br>gtgattctgaaacgaaatacaacccgtccttccaaggccac<br>gtcactatctcagccgacaagtccgtcaccaccacctacct<br>gaagtggagcagcctgaaggcctcggacactgccacgta<br>ttactgtgtgaaaggaagtgagacctggggccagggagtc<br>ctggtcaccgtctcctca | 346 | cagtctgtgctgacgcagccagcctccctctcagcatctcctg<br>gagcatcagccagtctcacatgtaccttcagcggtggcatcaa<br>tgttgctggctacaacatactctggtaccaacagaaggcaggg<br>agtcctcccggtatcttctgaggtacaaatcagactcaactaa<br>ggacagggctctggagtccccagccgcttctctggatccaa<br>agatgcttcagcgaatacaggaattttacgcatctctgggctcc<br>agtctgaggatgaggctgactattactgtgccattgggcacag<br>cagcggtggatattcggaggagggacccggctgaccgtcct<br>c |
| 342 | EVQLVQSGAEVKRPGESLTISCKTSGYSF<br>TDNWISWVRQMPKGLEWMGSIYPGDS<br>ETKYNPSFQGHVTISADKSVTTTYLKWSS<br>LKASDTATYYCVKGSETWGQGVLVTVSS | 347 | QSVLTQPASLSASPGASASLTCTFSGGINVA<br>GYNILWYQQKAGSPPRYLLRYKSDSTKDQ<br>GSGVPSRFSGSKDASANTGILRISGLQSEDEA<br>DYYCAIGHSSGWIFGGGTRLTVL |
| | FVM37: | | |
| 351 | caggtgcagctggtgcaatctggagcagaggtgaaaagg<br>cccggggagtctctgaagatctcctgtaagacttctggatac<br>aggtttaccagcagctggatcagctgggtgcgccagatgc<br>ccgggaaagggctgagtggttggggagcatctatcctgg<br>tgattctgaaacgaaatacaaccgtccttccaaggccacg<br>tcactatctcagccgacaagtccgtcaccaccacctacct<br>aagtggagcagcctgaaggcctcggacactgccacgtatt<br>actgtgtgaaaggaagtgagacctggggccagggagtcc<br>tggtcaccgtctcctca | 356 | tcctctgagctgactcagccagcctccctctcagcatctcctgg<br>agcatcagccagtctcacatgtaccttcagcggtggcatcaat<br>gttgctggctacaacatactctggtaccaacagaaggcaggg<br>agtcctcccggtatcttctgaggtacaaatcagactcaactaa<br>ggacagggctctggagtccccagccgcttctctggatccaa<br>agatgcttcagcgaatacaggaattttacgcatctctgggctcc<br>agtctgaggatgaggctgactattactgtgccattgggcacag<br>cagcggtggatattcggaggagggacccggctgaccgtcct<br>c |
| 352 | QVQLVQSGAEVKRPGESLKISCKTSGYRE<br>TSSWISWVRQMPKGLEWLGSIYPGDSE<br>TKYNPSFQGHVTISADKSVTTTYLKWSSL<br>KASDTATYYCVKGSETWGQGVLVTVSS | 357 | SSELTQPASLSASPGASASLTCTFSGGINVA<br>GYNILWYQQKAGSPPRYLLRYKSDSTKDQ<br>GSGVPSRFSGSKDASANTGILRISGLQSEDEA<br>DYYCAIGHSSGWIFGGGTRLTVL |
| | FVM38: | | |
| 361 | caggtgcagctggtgcagtctggagcagaggtgaaaagg<br>cccggggaatctctgacgatctcctgtaagacttctggatac<br>agctttaccgacagctggatcggctgggtgcgccagatgc<br>ccgggaaaggcctgagtggatggcgagcatctatcctga<br>tgattctgaaacgaaatacaacccgtccttccaaggccacg | 366 | cagcctgtgctgactcagccagcctccctctcagcatctcctgg<br>agcatcagccagtctcacatgtaccttcagcggtggcatcaat<br>gttgctggctacaaccatactctggtaccagcagaaggcaggg<br>agtcctcccggtatcttctgaggtacaaatcagactcaactaa<br>ggaccagggctctggagtccccagccgcttctctggatccaa |

TABLE 2-continued

Macaque Antibody VH and VL Sequences

| SEQ ID | Heavy Chain / Heavy Chain Variable region | SEQ ID | Light Chain / Light Chain variable region |
|---|---|---|---|
| | tcactatctcagccgacaagtccgtcaccaccacctactg aagtggagcagcctgaaggcctcggacactgccacgtatt actgtgtgaaaggaagtgagacctggggccagggagtcc tggtcaccgtctcctca | | agatgcttcagcgaatacaggaattttacgcatctctgggctcc agtctgaggatgaggctgactattactgtgccattgggcacag cagcggttggatattcggaggagggacccggctgaccgtcct c |
| 362 | QVQLVQSGAEVKRPGESLTISCKTSGYSF TDSWIGWVRQMPGKGLEWMASIYPDDS ETKYNPSFQGHVTISADKSVTTTYLKWSS LKASDTATYYCVKGSETWGQGVLVTVSS | 57 | QPVLTQPASLSASPGASASLTCTFSGGINVA GYNILWYQQKAGSPPRYLLRYKSDSTKDQG SGVPSRFSGSKDASANTGILRISGLQSEDEAD YYYCAIGHSSGWIFGGGTRLTVL |

FVM39:

| 371 | gaggtgcagctggtgcaatctggagcagaggtgaaaagg cccgggggaatctctgaggatctcctgtaagacttctggatac agcttttaccgacagctggatcagctgggtgcgccagatgc ccgggaaagggctggagtggttggggagcatctatcctg tgattctgaaacgaaatacaacccgtccttccaaggccacg tcactatctcagccgacaagtccgtcaccaccacctactg aagtggagcagcctgaaggcctcggacactgccacgtatt actgtgtgaaaggaagtgagacctggggccagggagtcc tggtcaccgtctcctca | | cagcctgtgctgactcagccgcctcctctcagcatctcctg gagcatcagccagtctcacatgcaccttcagcggtggcatcaa tgttgctggctacaacatactctggtaccagcagaaggcaggg agtcctcccccgtatcttctgaggtacaaatcagactcaactaa ggaccagggtctcgagtcccccagccgcttctctggatccaa agatgcttcagcgaacacaggaattttacgcatctctgggctcc agtctgaggatgaggctgactattactgtgccattgggcacag cagcggttggatattcggaggagggacccggctgaccgtcct c |
| 372 | EVQLVQSGAEVKRPGESLRISCKTSGYSF TDSWISWVRQMPGKGLEWLGSIYPGDSE TKYNPSFQGHVTISADKSVTTTYLKWSSL KASDTATYYCVKGSETWGQGVLVTVSS | 57 | QPVLTQPASLSASPGASASLTCTFSGGINVA GYNILWYQQKAGSPPRYLLRYKSDSTKDQ GSGVPSRFSGSKDASANTGILRISGLQSEDEA DYYCAIGHSSGWIFGGGTRLTVL |

FVM40:

| 381 | gaggtgcagctggtgcagtctggagcagaggtgaaaagg cccgggggaatctctgacgatctcctgtaagacttctggata cagttttaccgacagttggatcagctgggtgcgccagatgc ccggggaaaggcctggagtggatgggggagcatctatcctg gtgattctgaaacgaaatacaacccgtccttccaaggccac gtcactatctcagccgacaagtccgtcaccaccacctacct gaagtggagcagcctgaaggcctcggacactgccacgta ttactgtgtgaaaggaagtgagacctgggccagggagtc ctggtcaccgtctcctca | | Cagcctatgctgactcagccagcctccctctcagcatctcctg gagcatcagccagtctcacatgtaccttcagcggtggcatcaa tgttgctggctacaacatactctggtaccagcagaaggcaggg agtcctcccccgtatcttctgaggtacaaatcagactcaactaa ggaccagggtctcgagtcccccagccgcttctctggatccaa agatgcttcagcgaacacaggaattttacgcatctctgggctcc agtctgaggatgaggctgactattactgtgccattgggcacag cagcggttggatattcggaggagggacccggctgaccgtcct t |
| 382 | EVQLVQSGAEVKRPGESLTISCKTSGYSF TDSWISWVRQMPGKGLEWMGSIYPGDS ETKYNPSFQGHVTISADKSVTTTYLKWSS LKASDTATYYCVKGSETWGQGVLVTVSS | 387 | QPMLTQPASLSASPGASASLTCTFSGGINVA GYNILWYQQKAGSPPRYLLRYKSDSTKDQ GSGVPSRFSGSKDASANTGILRISGLQSEDEA DYYCAIGHSSGWIFGGGTRLTVL |

FVM41:

| 391 | gaggtgcagctggtgcagtctggagcagaggtgaaaagg cccgggggagtctctgaagatctcctgtaagacttctggatac agttttaccgacacctggatcagttgggtgcgccagatgcc cggggaaaggcctggagtggatggggggagcatctatcctggt gattctgaaacgaaatacaacccgtccttccaaggccacgt cactatctcagccgacaagtccgtcaccaccacctactga agtggagcagcctgaaggcctcggacactgccacgtatta ctgtgtgaaaggaagtgagacctggggccagggagtcct ggtcaccgtctcctca | | gagactgtggtgacccagccgcctcctctcagcatctcctg gagcatcagccagtctcacatgtaccttcagcggtggcatcaa tgttgctggctacaacatactctggtaccagcagaaggcaggg agtcctcccccgtatcttctgaggtacaaatcagactcaactaa ggaccagggtctcgagtcccccagccgcttctctggatccaa agatgcttcggccaacacagggattttacgcatctctgggctcc agtctgaggatgaggctgactattactgtgccattgggcacag cagcggtgtgttattcggaggagggacccggctgaccgtcct c |
| 392 | EVQLVQSGAEVKRPGESLKISCKTSGYSF TDTWISWVRQMPGKGLEWMGSIYPGDS ETKYNPSFQGHVTISADKSVTTTYLKWSS LKASDTATYYCVKGSETWGQGVLVTVSS | 397 | ETVVTQPASLSASPGASASLTCTFSGGINVA GYNILWYQQKAGSPPRYLLRYKSDSTKDQ GSGVPSRFSGSKDASANTGILRISGLQSEDEA DYYCAIGHSSGVLFGGGTRLTVL |

FVM42:

| 401 | gaggtgcagctggtggagtctggagcagaggtgaaaagg cccgggggaatctctgacgatctcctgtaagacttctggatac agcttttaccgacagctgggtcgcctggtgcgccagatgc ccggggaaaggcctggagtggatggggggagcatctatcctg gtgattctgaaacgaaatacaacccgtccttccaaggccac gtcactatctcagccgacaagtccgtcaccaccacctacct gaagtggagcagcctgaaggcctcggacactgccacgta ttactgtgtgaaaggaagtgagacctgggccagggagtc ctggtcaccgtctcctca | | cagactgtggtgactcagccagcctccctctcagcatctcctg gagcatcagccagtctcacatgtaccttcagcggtggcatcaa tgttgctggctacaacatactctggtaccagcagaaggcaggg agtcctcccccgtatcttctgaggtacaaatcagactcaactaa ggaccagggtctcgagtcccccagccgcttctctggatccaa agatgcttcagcgaatacaggaattttacgcatctctgggctcc agtctgaggatgaggctgactattactgtgccattgggcacag cagcggttggatattcggaggagggacccggctgaccgtcct c |
| 402 | EVQLVESGAEVKRPGESLTISCKTSGYSFT DSWVAWVRQMPGKGLEWMGSIYPGDSE | 407 | QTVVTQPASLSASPGASASLTCTFSGGINVA GYNILWYQQKAGSPPRYLLRYKSDSTKDQ |

TABLE 2-continued

Macaque Antibody VH and VL Sequences

| SEQ ID | Heavy Chain<br>Heavy Chain Variable region | SEQ ID | Light Chain<br>Light Chain variable region |
|---|---|---|---|
| | TKYNPSFQGHVTISADKSVTTTYLKWSSL<br>KASDTATYYCVKGSETWGQGVLVTVSS | | GSGVPSRFSGSKDASANTGILRISGLQSEDA<br>DYYCAIGHSSGWIFGGGTRLTVL |

TABLE 3

Macaque antibody CDR sequences

| Anti-body | VH | | | | | | VL | | | | | |
|---|---|---|---|---|---|---|---|---|---|---|---|---|
| | #* | CDR1 | # | CDR2 | # | CDR3 | # | CDR1 | # | CDR2 | # | CDR3 |
| FVM01P | 3 | GASISNYR | 4 | INGYSGST | 5 | PIIGGFTLEWFDV | 8 | QGIRNY | 9 | AAS | 10 | LQGYRTPFT |
| FVM02P | 13 | GFTFSDYA | 14 | IRGKAYGGTA | 15 | TSQGVTVATPYH | 18 | QSLLHSGGKTY | 19 | EVS | 20 | MQGIQLPLT |
| FVM03 | 23 | SGYSISSAYAWS | 24 | VGSSSD | 25 | ARDRANNSMDV | 28 | QSLLYSSNNKNY | 29 | WAS | 30 | QQYYSTPLT |
| FVM04 | 33 | GLSLSDYFMH | 34 | IQTKAFTYKT | 35 | IAVTPDFYY | 38 | QDITIN | 39 | VAS | 40 | QQYNNYPLT |
| FVM05 | 43 | GFSISSGYGWS | 44 | IGGSSGSTS | 45 | ARRYSSYRSWFDV | 48 | NIGSKS | 49 | ADS | 50 | QVWDSSSDHWV |
| FVM06 | 53 | GYSFTNYWIS | 54 | IDPSDSDTR | 55 | VKGSET | 58 | GGINVAGYN | 59 | YKSDSTK | 60 | AIGHSSGWI |
| FVM07 | 63 | GYSFTDSWIG | 64 | IYPGDSDTK | 65 | VAREAY | 68 | GGINVAGYH | 69 | YKSDSDK | 70 | AIGHSSGVL |
| FVM08 | 73 | GYSFTDSWVA | 74 | IYPGDSDTR | 75 | VKGADD | 58 | GGINVAGYN | 59 | YKSDSTK | 60 | AIGHSSGWI |
| FVM09 | 73 | GYSFTDSWVA | 84 | IYPGDSETK | 85 | VKGSET | 58 | GGINVAGYN | 59 | YKSDSTK | 60 | AIGHSSGWI |
| FVM10 | 73 | GYSFTDSWVA | 84 | IYPGDSETK | 95 | AKGSET | 58 | GGINVAGYN | 69 | YKSDSDK | 60 | AIGHSSGWI |
| FVM11 | 73 | GYSFTDSWVA | 84 | IYPGDSETK | 55 | VKGSET | 58 | GGINVAGYN | 59 | YKSDSTK | 60 | AIGHSSGWI |
| FVM12 | 113 | EYSFTGSWIS | 74 | IYPGDSDTR | 55 | VKGSET | 58 | GGINVAGYN | 119 | YKSDSDN | 120 | AIGHSTGWV |
| FVM13 | 123 | GYSFTSSWIS | 74 | IYPGDSDTR | 55 | VKGSET | 58 | GGINVAGYN | 59 | YKSDSTK | 60 | AIGHSSGWI |
| JM14 | 133 | GYSFTSTWIT | 84 | IYPGDSETK | 55 | VKGSET | 58 | GGINVAGYN | 59 | YKSDSTK | 60 | AIGHSSGWI |
| JM15 | 143 | GYTFTDYWIA | 84 | IYPGDSETK | 55 | VKGSET | 58 | GGINVAGYN | 59 | YKSDSTK | 60 | AIGHSSGWI |
| JM16 | 153 | GYSFTSTWIN | 84 | IYPGDSETK | 55 | VKGSET | 58 | GGINVAGYN | 59 | YKSDSTK | 120 | AIGHSTGWV |
| JM17 | 163 | GYSFTDSWIS | 164 | IYPGDSDAR | 55 | VKGSET | 58 | GGINVAGYN | 119 | YKSDSDN | 60 | AIGHSSGWI |
| JM18 | 173 | GYSFTNIWIS | 84 | IYPGDSETK | 55 | VKGSET | 68 | GGINVAGYH | 179 | YKSDSEK | 180 | AIGHSSSGWV |
| JM19 | 73 | GYSFTDSWVA | 64 | IYPGDSDTK | 55 | VKGSET | 68 | GGINVAGYH | 69 | YKSDSDK | 190 | AIGHSSGLL |
| FVM20 | 193 | GYSFTGSWIS | 84 | IYPGDSETK | 55 | VKGSET | 68 | GGINVAGYH | 179 | YKSDSEK | 60 | AIGHSSGWI |
| FVM21 | 73 | GYSFTDSWVA | 84 | IYPGDSETK | 75 | VKGADD | 58 | GGINVAGYN | 69 | YKSDSDK | 60 | AIGHSSGWI |
| FVM22 | 73 | GYSFTDSWVA | 84 | IYPGDSETK | 95 | AKGSET | 58 | GGINVAGYN | 59 | YKSDSTK | 60 | AIGHSSGWI |
| FVM23 | 193 | GYSFTGSWIS | 224 | IYPGDSDTT | 55 | VKGSET | 58 | GGINVAGYN | 59 | YKSDSTK | 230 | AIGHSSGLI |
| FVM24 | 73 | GYSFTDSWVA | 234 | IYPGDFQTR | 55 | VKGSET | 58 | GGINVAGYN | 59 | YKSDSTK | 60 | AIGHSSGWI |
| FVM25 | 143 | GYTFTDYWIA | 244 | IYPDDSDTR | 55 | VKGSET | 58 | GGINVAGYN | 119 | YKSDSDN | 120 | AIGHSTGWV |
| FVM26 | 143 | GYTFTDYWIA | 84 | IYPGDSETK | 55 | VKGSET | 58 | GGINVAGYN | 59 | YKSDSTK | 60 | AIGHSSGWI |
| FVM27 | 263 | GYSFASSWIS | 264 | IDPSDSATR | 55 | VKGSET | 58 | GGINVAGYN | 59 | YKSDSTK | 60 | AIGHSSGWI |
| FVM28 | 273 | GYRFTSSWIS | 274 | IDPSDSETR | 55 | VKGSET | 68 | GGINVAGYH | 179 | YKSDSEK | 180 | AIGHSSSGWV |
| FVM29 | 283 | GNSFTNNWIS | 274 | IDPSDSETR | 55 | VKGSET | 58 | GGINVAGYN | 59 | YKSDSTK | 60 | AIGHSSGWI |
| FVM31 | 73 | GYSFTDSWVA | 164 | IYPGDSDAR | 55 | VKGSET | 58 | GGINVAGYN | 59 | YKSDSTK | 60 | AIGHSSGWI |
| FVM32 | 73 | GYSFTDSWVA | 74 | IYPGDSDTR | 55 | VKGSET | 308 | GGITVPGYD | 59 | YKSDSTK | 60 | AIGHSSGWI |

TABLE 3-continued

Macaque antibody CDR sequences

| Anti-body | #* | VH CDR1 | # | VH CDR2 | # | VH CDR3 | # | VL CDR1 | # | VL CDR2 | # | VL CDR3 |
|---|---|---|---|---|---|---|---|---|---|---|---|---|
| FVM33 | 313 | RYSFTSSWIG | 74 | IYPGDSDTR | 55 | VKGSET | 58 | GGINVAGYN | 59 | YKSDSTK | 60 | AIGHSSGWI |
| FVM34 | 323 | GYSFTDSWVS | 84 | IYPGDSETK | 55 | VKGSET | 68 | GGINVAGYH | 69 | YKSDSDK | 120 | AIGHSTGWV |
| --JM35 | 333 | GYSFTSYWIT | 84 | IYPGDSETK | 55 | VKGSET | 58 | GGINVAGYN | 59 | YKSDSTK | 60 | AIGHSSGWI |
| JM36 | 343 | GYSFTDNWIS | 84 | IYPGDSETK | 55 | VKGSET | 58 | GGINVAGYN | 59 | YKSDSTK | 60 | AIGHSSGWI |
| JM37 | 123 | GYSFTSSWIS | 84 | IYPGDSETK | 55 | VKGSET | 58 | GGINVAGYN | 59 | YKSDSTK | 60 | AIGHSSGWI |
| JM38 | 63 | GYSFTDSWIG | 84 | IYPGDSETK | 55 | VKGSET | 58 | GGINVAGYN | 59 | YKSDSTK | 60 | AIGHSSGWI |
| JM39 | 163 | GYSFTDSWIS | 84 | IYPGDSETK | 55 | VKGSET | 58 | GGINVAGYN | 59 | YKSDSTK | 60 | AIGHSSGWI |
| JM40 | 163 | GYSFTDSWIS | 84 | IYPGDSETK | 55 | VKGSET | 58 | GGINVAGYN | 59 | YKSDSTK | 60 | AIGHSSGWI |
| FVM41 | 393 | GYSFTDTWIS | 84 | IYPGDSETK | 55 | VKGSET | 58 | GGINVAGYN | 59 | YKSDSTK | 60 | AIGHSSGWI |
| FVM42 | 73 | GYSFTDSWVA | 404 | IYPGDSETR | 55 | VKGSET | 58 | GGINVAGYN | 59 | YKSDSTK | 60 | AIGHSSGWI |

*SEQ ID NO 1.6 Isolation of Anti-Filovirus Macaque Antibodies by Screening Yeast Surface Display scFv.

The methods for generation of the yeast surface single-chain variable fragment antibody (scFv)-displayed library, selection of antigen-specific scFv (single chain fragment variable), have been described in detail previously (Keck Z Y, 2012, *PLoS Pathogens,* 8:e1002653). Screening strategy for this study is summarized in FIG. 4. Briefly, primers used in primary PCR reactions to amplify the gamma heavy chain, kappa and lambda light chains were described previously (Sundling et al., 2012, *J Immunol Methods,* 386:85-93) with the following modifications: for VH primers, the sequences

```
(5'-C GGG GCC ATG GCC-3' SEQ ID NO: 411,
underlined is a NcoI site)
and (5'-ACC TGT CGA CCC-3' SEQ ID NO: 412,
underlined is a SalI site)

For VL primers, the sequences
(5'-GT GGC TCC GGA GGT GGC GGA TCG-3'
SEQ ID NO: 413, underlined is a BspEl site),
and (5'-C GCC TGC GGC CGC-3' SEQ ID NO: 414,
underlined is a NotI site)
``` were added respectively to all forward Vλ and Vκ primers, and all reverse Vλ and Vκ primers. The yeast library (~$1\times10^8$ in size) was grown in synthetic dextrose Casamino acids (SD-CAA) with glucose replaced by galactose (SG-CAA) for 48 h at 18° C. $1\times10^7$ cells were FACS sorted with GPddmuc of combined triple antigens mixture (SUDV/EBOV/MARV). $1\times10^7$ cells were FACS sorted with GPdTM of combined triple antigens mixture (SUDV/EBOV/MARV). Between each round of selection, the collected cells were grown in SD-CAA and induced in SG-CAA medium. Selection was performed using a BD Bioscience FACS Vantage sorter. A portion of the collected cells were plated on SD-CAA 96-well plates. Individual clones reactive to different GP forms were screened by flow cytometry analysis. A second portion of the sorted cells were FACS sorted 1-2 rounds with alternated GP antigens and then plated on SD-CAA 96-well plates, followed by single clone screening by flow analysis. The third portion of FACS sorted cells was screened three more rounds with a peptide (EBOV GP aa79-96: VPSATKRWGFRSGVPPKV (SEQ ID NO: 415). The resulting positive cells were plated on SD-CAA 96-well plates followed by single clone screening by flow analysis. ScFv genes were extracted from individual clones that are positive by flow analysis and were sequenced (Elim Biopharmaceuticals, Inc., Hayward, Calif.). ScFvs having unique CDR3 were converted to full-length $IgG_1$ using the same vector as described above in direct Ig gene cloning from B cells (section 1.1.5. above). Antibodies that were generated from this pathway were designated as FVM03-FVM29 and FVM31-FVM42, as shown in Tables 2 and 3.

Example 2: Antibody Characterization 2.1 Reactivity to Filovirus Glycoproteins:

Data generated from the following three different binding assays are summarized in Table 4.

"Native" ELISA:

The binding specificity to filovirus glycoproteins by ELISA was performed, as described previously with slight modifications (Keck Z Y, 2012, *PLoS Pathogens,* 8:e1002653). Briefly, microtiter plates were pre-coated with 50 ng/well of each GP (SUDV, EBOV or MARV) in both forms of GPddmuc or GPdTM separately at 4° C. for overnight. The wells were blocked with 2.5% non-fat dry milk and 2.5% normal goat serum. Antibody supernatants collected on day 5 were added to the pre-coated wells. After wash, the bound antibodies in the supernatants were detected by anti-human immunoglobulin G (IgG)-horseradish peroxidase (Sigma) and TMB (3,3', 5', 5'-tetramethylbenzidine, sigma) substrate. Absorbance was measured at 450 nm and 570 nm. Vaccinated macaques 20667 serum/plasma was used as positive control at 1:1000 dilutions and No antigen coating wells was used as negative control.

"Denatured" ELISA:

To determine if the antibodies recognize a linear or conformational epitope "denatured" ELISA was performed as described previously (Keck Z Y, 2013, *J Virol.*, 87:37-51). Briefly, wells of 96-well plates were coated with filovirus GPs under native or denaturing conditions. For denaturation, filovirus GPs were denatured by incubation with 0.5% sodium dodecyl sulfate and 5 mM dithiothreitol for 15 min at 56° C. Filovirus GPs in coating buffer served as native antigens. Subsequent ELISA was performed as described above.

Competitive ELISA:

To determine if the antibodies recognize epitopes shared by a set of mouse monoclonal antibodies the competition between macaque and mouse antibodies for binding to filovirus glycoproteins was measured by ELISA as described previously (Keck Z Y, 2013, *J Virol.*, 87:37-51). Briefly, 50 μg of macaque antibody was added GP pre-coated well at a saturation concentration. After 1 h, 2 μg of purified mouse antibody was added. Subsequent ELISAs were performed as described above. The mouse antibodies used in these studies were: 5E4, 2D8, 21D10, 4F3, 4B8, 16G8, 17C6, 21B2, 2E4 and 8C4.

TABLE 4

Isotype and Binding pattern of 41 chimeric macaque-human (Fc) monoclonal antibodies.

| Macaque antibody | Isotype | Reactivity to Filovirus glycoproteins[a] | | | | | | | Compete with mouse Mab |
|---|---|---|---|---|---|---|---|---|---|
| | | SUDV Gpddmuc | EBOV Gpddmuc | MARV Gpddmuc | SUDV GPdTM | EBOV GPdTM | MARV GPdTM | DNT[b] | |
| FVM01P | IgG1 κ | + | + | − | + | + | − | + | NC |
| FVM02P | IgG1 κ | + | + | + | + | + | + | − | NC |
| FVM03 | IgG1 κ | − | − | + | − | − | + | + | 2D8 |
| FVM04 | IgG1 κ | + | + | − | + | + | − | − | 17C6, 8C4 |
| FVM05 | IgG1 κ | + | + | − | + | + | − | − | NC |
| FVM06 | IgG1 λ | + | + | − | + | + | − | + | NC |
| FVM07 | IgG1 λ | + | + | − | + | + | − | + | NC |
| FVM08 | IgG1 λ | + | + | − | + | + | − | + | NC |
| FVM09 | IgG1 λ | + | + | − | + | + | − | + | NC |
| FVM10 | IgG1 λ | + | + | − | + | + | − | + | NC |
| FVM11 | IgG1 λ | + | + | − | + | + | − | + | NC |
| FVM12 | IgG1 λ | + | + | − | + | + | − | + | NC |
| FVM13 | IgG1 λ | + | + | − | + | + | − | + | NC |
| FVM14 | IgG1 λ | + | + | − | + | + | − | + | NC |
| FVM15 | IgG1 λ | + | + | − | + | + | − | + | NC |
| FVM16 | IgG1 λ | + | + | − | + | + | − | + | NC |
| FVM17 | IgG1 λ | + | + | − | + | + | − | + | NC |
| FVM18 | IgG1 λ | + | + | − | + | + | − | + | NC |
| FVM19 | IgG1 λ | + | + | − | + | + | − | + | NC |
| FVM20 | IgG1 λ | + | + | − | + | + | − | + | NC |
| FVM21 | IgG1 λ | + | + | − | + | + | − | + | NC |
| FVM22 | IgG1 λ | + | + | − | + | + | − | + | NC |
| FVM23 | IgG1 λ | + | + | − | + | + | − | + | NC |
| FVM24 | IgG1 λ | + | + | − | + | + | − | + | NC |
| FVM25 | IgG1 λ | + | + | − | + | + | − | + | NC |
| FVM26 | IgG1 λ | + | + | − | + | + | − | + | NC |
| FVM27 | IgG1 λ | + | + | − | + | + | − | + | NC |
| FVM28 | IgG1 λ | + | + | − | + | + | − | + | NC |
| FVM29 | IgG1 λ | + | + | − | + | + | − | + | NC |
| FVM31 | IgG1 λ | + | + | − | + | + | − | + | NC |
| FVM32 | IgG1 λ | + | + | − | + | + | − | + | NC |
| FVM33 | IgG1 λ | + | + | − | + | + | − | + | NC |
| FVM34 | IgG1 λ | + | + | − | + | + | − | + | NC |
| FVM35 | IgG1 λ | + | + | − | + | + | − | + | NC |
| FVM36 | IgG1 λ | + | + | − | + | + | − | + | NC |
| FVM37 | IgG1 λ | + | + | − | + | + | − | + | NC |
| FVM38 | IgG1 λ | + | + | − | + | + | − | + | NC |
| FVM39 | IgG1 λ | + | + | − | + | + | − | + | NC |
| FVM40 | IgG1 λ | + | + | − | + | + | − | + | NC |
| FVM41 | IgG1 λ | + | + | − | + | + | − | + | NC |
| FVM42 | IgG1 λ | + | + | − | + | + | − | + | NC |

[a]Reactivity was measured by ELISA. [b]Reactivity of the macaque-human MAbs to SDS and heat denatured filovirus glycoproteins: + indicates antibody to linear epitope, − indicates antibody to conformational epitope. [c]Neutralization was determined using an ELISA-based microneutralization assay. NC: No competition. ND: not determined.

2.2 Determination of Relative Binding of Macaque-Human Chimeric Antibodies to Filovirus Glycoproteins or Virus-Like Particles (VLP):

Relative binding of the antibodies to different filovirus glycoproteins and VLPs was determined by ELISA at various concentrations of the antibodies and the effective concentration at 50% maximal binding ($EC_{50}$) determined. Purified GPddmuc, GPdTM, or VLPs from the three filovirus species (SUDV, EBOV, and MARV) were immobilized on 96-well Nunc MaxiSorp plates (ThermoFisher Scientific) and incubated with serial dilutions of the macaque-human chimeric antibodies. Bound antibodies were detected using an HRP-conjugated anti-mouse secondary antibody (KPL) and TMB substrate (Life Technologies). Absorbance values determined at 650 nm were transformed using Softmax® 4 parameter curve-fit (Molecular Devices). Table 5 shows the $EC_{50}$ values.

as a positive control. All assays utilized a luminescent substrate (SuperSignal ELISA Pico, Pierce) for detection in the cell-based ELISA assays. As shown in Table 6, several macaque antibodies showed significant neutralization of both EBOV and SUDV.

TABLE 5

Binding $EC_{50}$ (nM) of chimeric macaque-human antibodies to filovirus glycoproteins and virus-like particles (VLP).

| Clone ID | SUDV-VLP | SUDV-GPdTM | SUDV-GPddmuc | EBOV-VLP | EBOV-GdTM | EBOV-GPddmuc | MARV-VLP | MARV-GPdTM | MARV-GPddmuc |
|---|---|---|---|---|---|---|---|---|---|
| FVM01 | 0.319 | 0.111 | 0.047 | 0.459 | 0.115 | 0.057 | ND | ND | ND |
| FVM02P | 0.351 | 0.787 | 0.158 | 0.489 | 0.193 | 0.127 | 7.733 | >10 | >10 |
| FVM03 | ND | ND | ND | ND | ND | ND | 0.793 | 0.317 | 0.306 |
| FVM04 | 0.193 | 0.326 | 0.164 | 0.306 | 0.275 | 0.149 | ND | ND | ND |
| FVM05 | 61.533 | 5.833 | 8.600 | 18.000 | 1.633 | 2.673 | ND | ND | ND |
| FVM06 | 0.213 | 0.062 | 0.050 | 0 215 | 0.071 | 0.059 | ND | ND | ND |
| FVM07 | 18.200 | 0.847 | 0.491 | 1.707 | 0.111 | 0.119 | ND | ND | ND |
| FVM08 | 0.135 | 0.071 | 0.048 | 0.193 | 0.075 | 0.461 | ND | ND | ND |
| FVM09 | 21.267 | 9.733 | 7.733 | 24.200 | 7.200 | 7.067 | ND | ND | ND |
| FVM10 | 0.687 | 0.140 | 0.082 | 0.653 | 0.126 | 0.079 | ND | ND | ND |
| FVM11 | 0.189 | 0.069 | 0.053 | 0.219 | 0.083 | 0.059 | ND | ND | ND |
| FVM12 | 0.673 | 0.129 | 0.081 | 0.622 | 0.095 | 0.091 | ND | ND | ND |
| FVM13 | 0.144 | 0.070 | 0.051 | 0.198 | 0.078 | 0.062 | ND | ND | ND |
| FVM14 | 0.157 | 0.137 | 0.077 | 0.780 | 0.113 | 0.086 | ND | ND | ND |
| FVM15 | 0.129 | 0.057 | 0.035 | 0.151 | 0.059 | 0.042 | ND | ND | ND |
| FVM16 | 1.427 | 0.108 | 0.059 | 0.655 | 0.101 | 0.066 | ND | ND | ND |
| FVM17 | 1.433 | 0.179 | 0.113 | 0.767 | 0.096 | 0.096 | ND | ND | ND |
| FVM18 | 1.080 | 0.168 | 0.108 | 1.027 | 0.150 | 0.101 | ND | ND | ND |
| FVM19 | 5.400 | 0.415 | 0.267 | 0.967 | 0.121 | 0.120 | ND | ND | ND |
| FVM20 | 32.933 | 0.713 | 0.119 | 1.293 | 0.135 | 0.081 | ND | ND | ND |
| FVM21 | 0.373 | 0.113 | 0.067 | 0.320 | 0.080 | 0.067 | ND | ND | ND |
| FVM22 | 0.173 | 0.093 | 0.600 | 0.253 | 0.087 | 0.067 | ND | ND | ND |
| FVM23 | 0.353 | 0.120 | 0.080 | 0.367 | 0.113 | 0.087 | ND | ND | ND |
| FVM24 | 3.200 | 0.167 | 0.120 | 0.513 | 0.173 | 0.153 | ND | ND | ND |
| FVM25 | 0.960 | 0.300 | 0.180 | 0.473 | 0.153 | 0.120 | ND | ND | ND |
| FVM26 | 0.153 | 0.133 | 0.080 | 0.260 | 0.113 | 0.100 | ND | ND | ND |
| FVM27 | 0.120 | 0.053 | 0.040 | 0.233 | 0.053 | 0.047 | ND | ND | ND |
| FVM28 | 0.580 | 0.073 | 0.047 | 0.593 | 0.073 | 0.047 | ND | ND | ND |
| FVM29 | 24.067 | 15.133 | 12.800 | 30.333 | 11.467 | 11.600 | ND | ND | ND |
| FVM31 | 0.193 | 0.153 | 0.093 | 0.320 | 0.153 | 0.107 | ND | ND | ND |
| FVM32 | 0.187 | 0.273 | 0.127 | 0.660 | 0.113 | 0.073 | ND | ND | ND |
| FVM33 | 0.080 | 0.067 | 0.040 | 0.173 | 0.080 | 0.040 | ND | ND | ND |
| FVM34 | 0.227 | 0.047 | 0.027 | 0.193 | 0.033 | 0.027 | ND | ND | ND |
| FVM35 | 0.140 | 0.047 | 0.033 | 0.233 | 0.053 | 0.033 | ND | ND | ND |
| FVM37 | 0.127 | 0.067 | 0.033 | 0.227 | 0.080 | 0.047 | ND | ND | ND |
| FVM38 | 0.147 | 0.100 | 0.053 | 0.253 | 0.080 | 0.060 | ND | ND | ND |
| FVM39 | 0.047 | 0.040 | 0.020 | 0.080 | 0.033 | 0.027 | ND | ND | ND |
| FVM40 | 0.113 | 0.060 | 0.033 | 0.173 | 0.060 | 0.040 | ND | ND | ND |
| FVM41 | 0.320 | 0.087 | 0.053 | 0.360 | 0.067 | 0.047 | ND | ND | ND |

2.3 In Vitro Neutralization of Live Filovirus by EBOV and SUDV in Microneutralization Assays:

Vero E6 cells seeded at a density of 4.0E+05 cells/well were incubated for 24 hours at 37° C. with 5% $CO_2$. Virus stock (1.20E+04 pfu) was incubated with antibody for 1 hour then split equally into 3 wells (replicates) containing cells to achieve 4.0E+03 pfu per well. The inoculum was removed after one hour at 37° C. with 5% $CO_2$ and replaced with fresh media. For EBOV microneutralization, cells were permeabilized with methanol then fixed using 10% phosphate buffered formalin for cell-based ELISA. Rabbit polyclonal antibody was used for the detection of EBOV matrix protein (VP40). Monoclonal antibody known to neutralize EBOV was used as a positive control. For SUDV microneutralization, cells were fixed using 10% phosphate buffered formalin for cell-based ELISA. Rabbit polyclonal antibody was used for the detection of SUDV glycoprotein (GP). Monoclonal antibody known to neutralize SUDV was used

TABLE 6

Neutralization of EBOV, and SUDV by supernatants from 293T cells transfected with cDNA for light and heavy chain of anti-filovirus macaque-human chimeric antibodies

| Macaque antibody | Neutralization of live filovirus | |
|---|---|---|
|  | EBOV | SUDV |
| FVM01P | ++ | ++ |
| FVM02P | ND | ++ |
| FVM03 | + | ++ |
| FVM04 | +++ | +++ |
| FVM05 | ND | ND |
| FVM06 | ND | + |
| FVM07 | ++ | ++ |
| FVM08 | ++ | ++ |
| FVM09 | +++ | ++ |
| FVM10 | − | ++ |
| FVM11 | +++ | ++ |
| FVM12 | ++ | + |
| FVM13 | ++ | ++ |
| FVM14 | ++ | ++ |

TABLE 6-continued

Neutralization of EBOV, and SUDV by supernatants from 293T cells transfected with cDNA for light and heavy chain of anti-filovirus macaque-human chimeric antibodies

| Macaque antibody | Neutralization of live filovirus | |
|---|---|---|
| | EBOV | SUDV |
| FVM15 | ++ | + |
| FVM16 | − | + |
| FVM17 | ++ | ++ |
| FVM18 | + | + |
| FVM19 | − | + |
| FVM20 | ++ | ++ |
| FVM21 | ++ | +++ |
| FVM22 | − | +++ |
| FVM23 | ++ | +++ |
| FVM24 | +++ | +++ |
| FVM25 | +++ | +++ |
| FVM26 | − | +++ |
| FVM27 | − | +++ |
| FVM28 | − | +++ |
| FVM29 | − | +++ |
| FVM31 | − | +++ |
| FVM32 | − | − |
| FVM33 | − | − |
| FVM34 | ++ | +++ |
| FVM35 | +++ | +++ |
| FVM36 | − | − |
| FVM37 | − | +++ |
| FVM38 | − | +++ |
| FVM39 | − | +++ |
| FVM40 | − | +++ |
| FVM41 | − | +++ |
| FVM42 | − | − |

2.4 Binding Profile of Chimeric Macaque-Human Antibodies

Upon consideration of the breadth of reactivity, expression level, and exclusion of nearly identical clones, an initial set of six chimeric antibodies was selected for further characterization: FVM01p, FVM02p, FVM04, FVM09, FVM13, and FVM20. These antibodies were produced by transfecting 293T cells with the heavy and light chain encoding plasmids, purified by protein G chromatography, and tested for binding to GP from four ebolavirus species as well as MARV (Musoke strain). All six mAbs bound tightly to EBOV GPΔTM with $EC_{50}$ values ranging from 50 to 100 pM (Table 7). FVM09 and FVM13 showed the strongest binding to all four ebolavirus species with $EC_{50}$ values below 15 ng/ml (100 pM) (Table 7). Strong binding to SUDV, BDBV, and RESTV was also observed for FVM02p, and FVM04 (Table 7). FVM20 and FVM01p showed lower levels of binding to SUDV and RESTV, respectively (Table 7). The initial screen of cell supernatants suggested that only FVM02p showed weak binding to MARV GPΔTM (data not shown). Recently, we observed that direct coating of ELISA plates with MARV GPΔTM reduced binding of several antibodies specific to MARV GP, while observing higher binding to His-tagged MARV presented on nickel-coated plates (data not shown). Therefore, we tested the binding of several purified mAbs to His-tagged MARV GPΔTM on Ni plates and observed low to moderate binding by FVM02p and FVM04 to MARV (FIG. 5).

TABLE 7

Binding $EC_{50}$ (μg/ml) values of the selected macaque filovirus mAbs to GP from various species of filoviruses.

| | GP ELISA EC50 (μg/ml) | | | | |
|---|---|---|---|---|---|
| | EBOV | SUDV | BDBV | RESTV | MARV |
| FVM01p | 0.017 | 0.026 | 0.050 | 2.000 | NR |
| FVM02p | 0.011 | 0.062 | 0.050 | 0.050 | 1.000 |
| FVM04 | 0.017 | 0.026 | 0.050 | 0.050 | >10 |
| FVM09 | 0.008 | 0.011 | 0.020 | 0.010 | NR |
| FVM13 | 0.008 | 0.009 | 0.020 | 0.010 | NR |
| FVM20 | 0.008 | 0.329 | 0.100 | 0.010 | NR |

NR: non-reactive

Example 3: Epitope Mapping 3.1 General Binding Region of the Antibodies

EBOV GP consists of a receptor-binding GP1 linked by a disulfide bond to GP2 which is responsible for fusion with host membrane. GP1, in turn, consists of the RBR, glycan cap (GC), and mucin-like domain (MLD). Crystal structure of trimeric GP shows that RBR and GC form a chalice-like structure (Lee, et al., 2008, Nature, 454 (7201):177-182) (FIG. 6). GP2 wraps around this structure and along with the N-terminal tail of GP1 forms the base of the chalice (FIG. 6). Upon entry in endosomes and cleavage by cathepsins, the GC is removed from this structure; this cleaved GP (GPcl) (FIG. 6) can be produced in vitro using thermolysin (Hashiguchi, et al. 2015, Cell 160:904-912). During EBOV infection, the unedited GP gene encodes for a truncated form of GP with a unique C-terminus and a proteolytically cleaved short Delta peptide (Sanchez, et al., 1996, Proc Natl Acad Sci USA 93:3602-3607). The mature form of this soluble GP (sGP) consists of amino acids 31-295 followed by a unique 29-residue C-terminal tail and lacks both MLD and GP2 but retains most of the GC (FIG. 6). To determine the overall binding region of the antibodies we examined the binding of each mAb to GPΔmuc, GPcl, and sGP. As expected, all mAbs bound well to GPΔmuc (FIG. 6) and the binding $EC_{50}$ values were comparable with GPΔTM (compare with Table 7) suggesting that the MLD does not significantly block access to these epitopes. FVM09 failed to bind to GPcl, while binding by FVM13 and FVM20 to GPcl was severely reduced compared to GPΔmuc (FIG. 6), suggesting that the primary binding site for these three mAbs lies within the GC. In contrast, binding of FVM01p, FVM02p, and FVM04 was not affected by removal of GC (FIG. 6). Since they all bind to sGP (FIG. 6), the binding site of these three mAbs must lie within residues 31-200 in GP1 encompassing the RBR (Kuhn, et al., 2006, J Biol Chem, 281 (23):15951-15958). The complete loss of FVM02p binding to sGP (FIG. 6) indicated that FVM02p epitope lies within GP2.

3.2 Conformational or Continuous Nature of the Epitopes

Antibodies were tested for binding to chemically denatured glycoproteins by Western blotting and ELISA. For denatured ELISA antigen (GPΔTM) was chemically denatured using 0.2 M $Na_2CO_3$ pH 10.6 containing 10 mM DTT before coating ELISA plates. FVM04 binding to GP was completely lost upon denaturation of the antigen, while FVM09 and FVM02p binding were not affected. Binding of the other antibodies was reduced but not abrogated. Based on these data, we concluded that FVM09 and FVM02 react with continuous epitopes while FVM04 recognizes a conformational epitope. The epitopes for the other antibodies contain a linear core with additional discontinuous contact sites.

3.3 Identification of Linear Epitopes

To identify the linear epitopes for FVM02p and FVM09, we employed a competition assay using overlapping peptides spanning the entire GP sequences for EBOV and SUDV. ELISA plates were coated with EBOV or SUDV GPΔTM (1 µg/ml) as described above. 0.01 µg/ml of FVM02p or FVM09 were incubated for 1 hour with 27 different pools of 4-5 peptides spanning EBOV or SUDV GPΔTM in blocking buffer at a 100-fold molar excess to the mAbs. The peptide:FVM mixture was then added on top of the coated ELISA plates and allowed to binding for 1 hour at room temperature. The plates were washed and bound mAbs detected using Goat-Anti-human-HRP (KPL, Gaithersburg, Md.) and TMB substrate and absorbance values determined at 650 nm on a VersaMax plate reader. A decrease in optical density (OD) compared to the control peptide suggested that pool contained a peptide with the epitope of the corresponding mAb. These pools were selected for individual peptide screening performed in the same manner as above Peptides sharing the EBOV GP residues 286-290 (GEWAF) effectively blocked the binding of FVM09 to EBOV GP (FIG. 7A) and SUDV GP (data not shown). This region is located within a disordered loop connecting β17 and β18 (Lee, et al., 2008, Nature, 454 (7201):177-182) within the glycan cap on the side of the GP chalice (FIG. 7B) and is 100% conserved across all ebolavirus species (FIG. 7C). Using the same approach we found that peptides containing EBOV GP residues 526-535 competed with binding of FVM02p to EBOV GP (FIG. 7D) and SUDV GP (data not shown). This region is located at the tip of the fusion loop in GP2 (Lee, et al., 2008, Nature, 454 (7201):177-182) (FIG. 7E) and is conserved within the ebolavirus species (FIG. 7F). Seven out of ten residues of the putative FVM02p epitope are also identical between ebolavirus and marburgvirus species (FIG. 7F).

3.4 Identification of Conformational Epitopes

Alanine scanning mutagenesis was used to identify the conformational epitope of FVM04. In this EBOV GP alanine mutant library developed by Integral Molecular (Philadelphia, Pa.) residues 33-676 of full-length EBOV GP are mutagenized to create a library of clones, each with an individual point mutant. Residues are changed to alanine (with alanine residues changed to serine). Cells expressing EBOV alanine mutants were immunostained with FVM04 and mean cellular fluorescence was measured by flow cytometer. Mutations within critical clones were identified as critical to the MAb epitope if they did not support reactivity of the MAb, but did support reactivity of other conformation-dependent MAbs.

Using this method we identified three surface exposed residues in the Core GP (K115, D117, and G118) as critical contact points of FVM04. These residues are located on the top of GP1 between the glycan cap and the axis of trimer (FIG. 8A). This region forms a basic patch that is adjacent to a hydrophobic cavity referred to a crest and trough, respectively (Hashiguchi, et al. 2015, Cell 160:904-912). Both the crest and trough are needed for binding to the filovirus receptor NPC1 (Hashiguchi, et al. 2015, Cell 160: 904-912). The trough is occupied by the β14-β15 loop from the glycan cap thus preventing an interaction with the NPC1 receptor before this loop (FIG. 8C) is removed along with the rest of glycan cap by cathepsin cleavage in the endosome (Hashiguchi, et al. 2015, Cell 160:904-912) (FIG. 8B). The occlusion of the trough in EBOV GP structure is the reason why several panfilovirus antibodies targeting this region do not bind full EBOV GP but can bind cleaved GP (Hashiguchi, et al. 2015, Cell 160:904-912; Flyak et al. 2015, Cell 160:893-903). In contrast to the trough, the crest is well exposed on the top of GP (FIG. 8B). No antibodies recognizing this critical exposed region have been identified before discovery of FVM04. Thus FVM04 bound to the crest on the surface of the virus is likely to co-migrate to the endosomes and disrupt the engagement of NPC1 receptor in endosomes that is required for viral entry into the cytosol (Carette, et al. 2011, Nature 477(7364):340-3).

Example 4: Neutralization Activity of the Filovirus Antibodies

The neutralizing activity of the mAbs was first tested in a VSV-GP pseudotype assay. Briefly, Vero cells were plated at 60,000 cells per well in 96-well plates and incubated overnight at 37° C.+5% $CO_2$. The next day, mAbs were diluted and mixed independently with vesicular stomatitis virus lacking G protein and expressing various filovirus GP (VSV-GP) (for EBOV, SUDV, and MARV). After 1 hour, 100 µL of the mixture was added to Vero cells, with a final MOI of 0.04. Plates were incubated for 1 hour at 37° C.+5% C02 to allow virus to adhere to cells before adding an additional 100 µL of EMEM and incubating at 37° C.+5% $CO_2$ overnight. 24 hours later, the medium was removed from wells and cells were lysed with 30 µL of 1× Passive Lysis Buffer (Promega). Plates were rocked at 1.5 rpm for 30 min before the addition of 30 µL of luciferase substrate (Promega). Luminescence was immediately recorded using a TECAN M200 plate reader. Percent neutralization was calculated based on wells containing virus only. In this assay FVM04 and to a lesser extent FVM09, exhibited neutralizing activity (data not shown).

To further confirm these data we used a high content imaging-based assay using authentic EBOV and SUDV. Briefly, antibodies were diluted in PBS, mixed with equal volume of live virus (EBOV or SUDV), and the mixture was incubated at 37° C. for 1 hour before adding to Vero cells in 96 well plates. The cells were incubated with mAb/virus inoculum (MOI~1) for 1 hour at 37° C., washed with PBS, and growth media alone without antibody was added to all wells. Cells were fixed at 48 hours post infection and infected cells were determined by immunofluorescence (IFA) using virus specific mAbs and fluorescently labeled secondary antibodies. Percent of infected cells were determined using an Operetta and Harmony software. Data is expressed as the percent of inhibition relative to vehicle control treated cells for both EBOV (FIG. 9A) and SUDV (FIG. 9B). As shown in FIG. 9A and FIG. 9B, significant neutralization of both viruses was observed only for FVM04 in this assay.

Example 5: In Vivo Efficacy of Filovirus Antibodies

In vivo efficacy of the chimeric antibodies was evaluated in BALB/c mice using mouse-adapted EBOV (MA-EBOV) (Bray, et al. 1998, J Infect Dis 178:651-61). Mice were infected with 1,000 plaque-forming units (PFU) of MA-EBOV and treated either with two doses of antibody at 2 hours and three days post challenge, or a single dose 3 days post challenge. All control mice succumbed to infection within 6-9 days post infection, while mice treated twice with FVM04, FVM09, FVM20, or FVM02p showed, respectively, 100%, 67%, 60%, and 47% survival (FIG. 10A). In contrast, all the mice treated with FVM01p died from infection (FIG. 10A). Delayed treatment with a single injection of FVM04 three days after challenge also led to survival of 40% of mice (FIG. 10A). Animals treated with the protective mAbs lost less weight as compared to control animals and those treated with FVM01p (FIG. 10B). In particular, mice treated with FVM04 lost no more than 5% weight compared to over 25% weight loss in controls. Although FVM02p binding to MARV GPΔTM was very low, we tested the efficacy of FVM02p in a mouse model of Marburg infection. In two experiments, we observed 20% and 30% protection from lethal challenge when mice were treated respectively with FVM02p on days 0 and 3 or 0 and 4 (FIG. 11A and FIG. 11B), however the protection was not statistically significant.

The breadth and scope of this disclosure should not be limited by any of the above-described exemplary aspects, but should be defined only in accordance with the following claims and their equivalents.

What is claimed is:

1. An isolated antibody or antigen-binding fragment thereof comprising a binding domain that specifically binds to a filovirus glycoprotein epitope, wherein the binding domain comprises VH-CDR1, VH-CDR2, VH-CDR3, VL-CDR1, VL-CDR2, and VL-CDR3 amino acid sequences identical to SEQ ID NOs: 33, 34, 35, 38, 39, and 40, respectively.

2. The antibody or antigen-binding fragment thereof of claim 1, wherein the binding domain comprises heavy chain variable region (VH) and light chain variable region (VL) amino acid sequences comprising SEQ ID NO: 32 and SEQ ID NO: 37, respectively.

3. The antibody or antigen-binding fragment thereof of claim 1 which is a non-human primate (NHP) antibody, a humanized antibody, a chimeric antibody, or a fragment thereof.

4. The antibody or antigen-binding fragment thereof of claim 1, which is a monoclonal antibody, a component of a polyclonal antibody mixture, a recombinant antibody, a multispecific antibody, or any combination thereof.

5. The antibody or antigen-binding fragment thereof of claim 1, comprising an Fv fragment, an Fab fragment, an F(ab')2 fragment, an Fab' fragment, a dsFv fragment, an scFv fragment, an scFab fragment, an sc(Fv)2 fragment, or any combination thereof.

6. The antibody or antigen-binding fragment thereof of claim 1, wherein binding of the binding domain to the epitope on a filovirus fully or partially neutralizes infectivity of the filovirus.

7. The antibody or antigen-binding fragment thereof of claim 1, which is conjugated to an antiviral agent, a protein, a lipid, a detectable label, a polymer, or any combination thereof.

8. A composition comprising the antibody or antigen-binding fragment thereof of claim 1, and a carrier.

9. A method of making the antibody or antigen-binding fragment thereof of claim 1, comprising:
   (a) culturing a host cell wherein the host cell comprises a vector comprising an isolated polynucleotide or a combination of polynucleotides encoding the antibody or antigen-binding fragment thereof of claim 1; and
   (b) isolating and purifying the antibody or fragment thereof.

10. The isolated antibody or antigen-binding fragment thereof of claim 1, wherein the binding domain specifically binds to the epitope on two or more filovirus species or strains.

11. The isolated antibody or antigen-binding fragment thereof of claim 1, wherein the binding domain is derived from a non-human primate (NHP) antibody.

\* \* \* \* \*

SEQUENCE LISTING

```
<160> NUMBER OF SEQ ID NOS: 444

<210> SEQ ID NO 1
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tgcaggagtc gggcccagga ctggtgaagc cctcggagac cctgtccctc      60
acctgcactg tctctggtgc ctccattagt aattacaggt ggaactggat ccgccagccc     120
ccagggaagg gactggagtg gattggggag atcaatggtt atagtgggag caccaactac     180
aaccccctcc tcaagagtcg agtcaccatt tcaaaagacg cgtccaagaa ccagttctcc     240
ctgaagctga cctctgtgac cgccgcggac acggccgtgt attactgtcc aataattggg     300
ggctttactt tagagtggtt cgatgtctgg ggcccgggag tcctggtcac cgtctcctca     360

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Asn Tyr
            20                  25                  30

Arg Trp Asn Trp Ile Arg Gln Pro Pro Gly Lys Gly Leu Glu Trp Ile
        35                  40                  45

Gly Glu Ile Asn Gly Tyr Ser Gly Ser Thr Asn Tyr Asn Pro Ser Leu
    50                  55                  60

Lys Ser Arg Val Thr Ile Ser Lys Asp Ala Ser Lys Asn Gln Phe Ser
65                  70                  75                  80

Leu Lys Leu Thr Ser Val Thr Ala Ala Asp Thr Ala Val Tyr Tyr Cys
            85                  90                  95

Pro Ile Ile Gly Gly Phe Thr Leu Glu Trp Phe Asp Val Trp Gly Pro
        100                 105                 110

Gly Val Leu Val Thr Val Ser Ser
    115                 120

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 3

Gly Ala Ser Ile Ser Asn Tyr Arg
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Asn Gly Tyr Ser Gly Ser Thr
1               5

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Ile Ile Gly Gly Phe Thr Leu Glu Trp Phe Asp Val
1               5                   10

<210> SEQ ID NO 6
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gatgttgtgc tgacccagtc tccatcctcc ctgtctgcat ctgtaggaga cagagtcacc      60
atcacttgca gggcaagtca gggcattaga aattatttaa attggtatca gcagaaacca     120
agaaaagctc ctaagctcct gatctatgct gcatccagtt tgcaaagtgg ggtcccatca     180
aggttcagcg gcagtggatc tgggacagaa ttcactctca ccatcagcag cctgcaggct     240
gaagattttg ctacttacta ctgtctacag ggttatagaa ccccattcac tttcggcccc     300
gggaccaaac tggatatcaa acgtacggtg                                      330

<210> SEQ ID NO 7
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Val Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Asn Trp Tyr Gln Gln Lys Pro Arg Lys Ala Pro Lys Leu Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Glu Phe Thr Leu Thr Ile Ser Ser Leu Gln Ala
65                  70                  75                  80

Glu Asp Phe Ala Thr Tyr Tyr Cys Leu Gln Gly Tyr Arg Thr Pro Phe
                85                  90                  95

Thr Phe Gly Pro Gly Thr Lys Leu Asp Ile Lys Arg Thr Val
            100                 105                 110

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gly Ile Arg Asn Tyr
1               5

<210> SEQ ID NO 9
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Ser
1

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Gln Gly Tyr Arg Thr Pro Phe Thr
1               5

<210> SEQ ID NO 11
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gaggtgcagc tggtggagtc cggggggaggc ttggtccagc ctggcgggtc cctgagactc      60
tcctgtgcag cctctggatt cactggattc accttcagtg attatgcttt ctactgggtc     120
cgccaggctc caggaaaggg gctagaatgg gtgggtttca ttagaggcaa agcttatggt     180
gggacagcag attacgccgc gtctgtgaaa ggcagattca ccatctccag agataattca     240
aagaatacgg cgtatctgca aatgagcagc ctgaaaaccg aggactcggc cgtatattat     300
tgtactagtc agggtgtaac agtagccaca ccttaccact ggggccaggg agtcctggtc     360
accgtctcct ca                                                         372

<210> SEQ ID NO 12
```

<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Phe
            20                  25                  30

Ser Asp Tyr Ala Phe Tyr Trp Val Arg Gln Ala Pro Gly Lys Gly Leu
        35                  40                  45

Glu Trp Val Gly Phe Ile Arg Gly Lys Ala Tyr Gly Gly Thr Ala Asp
    50                  55                  60

Tyr Ala Ala Ser Val Lys Gly Arg Phe Thr Ile Ser Arg Asp Asn Ser
65                  70                  75                  80

Lys Asn Thr Ala Tyr Leu Gln Met Ser Ser Leu Lys Thr Glu Asp Ser
                85                  90                  95

Ala Val Tyr Tyr Cys Thr Ser Gln Gly Val Thr Val Ala Thr Pro Tyr
            100                 105                 110

His Trp Gly Gln Gly Val Leu Val Thr Val Ser Ser
        115                 120

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Phe Thr Phe Ser Asp Tyr Ala
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Arg Gly Lys Ala Tyr Gly Gly Thr Ala
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Ser Gln Gly Val Thr Val Ala Thr Pro Tyr His
1               5                   10

<210> SEQ ID NO 16
<211> LENGTH: 345
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 16
gacattgtgc tgacccagtc tccactctcc ctgcccgtca cccctggaga gccggcctcc      60
atctcctgca ggtctagtca gagcctcctg catagtggtg aaaaaccta tttgtattgg     120 tacctgcaga agccaggcca gtctccacag ctcttgatcc atgaggtttc caaccgggcc    180
tctggagtcc ctgacaggtt cagtggcagt gggtcaggca ctgatttcac actgaaaatc    240
agccgggtgg aggctgagga tgttgggggtt tattactgca tgcaaggtat acagcttcct   300
ctcactttcg gcggagggac caaggtggag atcaaacgta cggtg                    345

<210> SEQ ID NO 17
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Gly Gly Lys Thr Tyr Leu Tyr Trp Tyr Leu Gln Lys Pro Gly Gln Ser
            35                  40                  45

Pro Gln Leu Leu Ile His Glu Val Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile Gln Leu Pro Leu Thr Phe Gly Gly Gly Thr Lys Val Glu Ile Lys
            100                 105                 110

Arg Thr Val
        115

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Leu Leu His Ser Gly Gly Lys Thr Tyr
1               5                   10

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19
```

Glu Val Ser
1

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Gln Gly Ile Gln Leu Pro Leu Thr
1               5

<210> SEQ ID NO 21
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
caggtgcagc tgcaggagtc gggcccagta ctggtgaagc cttcggagac cctgtccctc      60
acctgcgctg tctctggtta ctccatcagc agtgcttatg cctggagctg gatccgccag    120
cccccaggga aggggctgga gtgggttgga tatgtcggta gtagtgatga ctacaatccc    180
tccctcaaga gtcgagtcac catttcaaga gacacgtcca agaaccggat cttcctgaac    240
ctgaggtctc tgaccgccgc ggacacggcc gtgtattact gtgcgagaga cagggcgaac    300
aactcaatgg atgtctgggg ccggggagtt ctggtcaccg tctcctca                348

<210> SEQ ID NO 22
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Glu Ser Gly Pro Val Leu Val Lys Pro Ser Glu
1               5                   10                  15

Thr Leu Ser Leu Thr Cys Ala Val Ser Gly Tyr Ser Ile Ser Ser Ala
                20                  25                  30

Tyr Ala Trp Ser Trp Ile Arg Gln Pro Pro Gly Lys Gly Leu Glu Trp
            35                  40                  45

Val Gly Tyr Val Gly Ser Ser Asp Tyr Asn Pro Ser Leu Lys Ser
        50                  55                  60

Arg Val Thr Ile Ser Arg Asp Thr Ser Lys Asn Arg Ile Phe Leu Asn
65                  70                  75                  80

Leu Arg Ser Leu Thr Ala Ala Asp Thr Ala Val Tyr Tyr Cys Ala Arg
                85                  90                  95

Asp Arg Ala Asn Asn Ser Met Asp Val Trp Gly Arg Gly Val Leu Val
            100                 105                 110

Thr Val Ser Ser
        115

<210> SEQ ID NO 23
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 23

Ser Gly Tyr Ser Ile Ser Ser Ala Tyr Ala Trp Ser
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Gly Ser Ser Ser Asp
1               5

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Arg Asp Arg Ala Asn Asn Ser Met Asp Val
1               5                   10

<210> SEQ ID NO 26
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gaaattgtgc tgactcagtc tccagactcc ctgggtgtgt ctctgggaga gagggtcacc    60
atcaactgca gtccagccag agtctttta tacagctcca acaataagaa ctacttagcc    120
tggtaccagc agaaaccagg acaggctcct aagctgctca tttactgggc atctactcgg    180
gaatctgggg tccctaaccg attcagtggc agcgggtctg ggacagattt cactctcacc    240
atcagtggcc tgcaggctga agatgtggca gtgtattact gtcagcagta ttatagtact    300
cctctgacgt tcggccaagg gaccaaggtg gaaatcaaac gtacggtg               348

<210> SEQ ID NO 27
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Ile Val Leu Thr Gln Ser Pro Asp Ser Leu Gly Val Ser Leu Gly
1               5                   10                  15

Glu Arg Val Thr Ile Asn Cys Lys Ser Ser Gln Ser Leu Leu Tyr Ser
            20                  25                  30

Ser Asn Asn Lys Asn Tyr Leu Ala Trp Tyr Gln Gln Lys Pro Gly Gln
```

```
            35                  40                  45
Ala Pro Lys Leu Leu Ile Tyr Trp Ala Ser Thr Arg Glu Ser Gly Val
        50                  55                  60
Pro Asn Arg Phe Ser Gly Ser Gly Thr Asp Phe Thr Leu Thr
 65                 70                  75                  80
Ile Ser Gly Leu Gln Ala Glu Asp Val Ala Val Tyr Tyr Cys Gln Gln
                85                  90                  95
Tyr Tyr Ser Thr Pro Leu Thr Phe Gly Gln Gly Thr Lys Val Glu Ile
            100                 105                 110
Lys Arg Thr Val
        115

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Leu Leu Tyr Ser Ser Asn Asn Lys Asn Tyr
1               5                   10

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Ala Ser
1

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Gln Tyr Tyr Ser Thr Pro Leu Thr
1               5

<210> SEQ ID NO 31
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gaggtgcagc tggtgcagtc tggggggaggc ttggtgcagc ctggggggtc catgagactc    60
tcctgtgaag cctctggatt aagtctcagt gactacttca tgcactgggt ccgccaggct   120
caagggaaag gactagagtg gataggttta atacaaacca aagctttcac ttacaagaca   180
gaatatcctg cggctgtgaa aggcagattc accatctcaa gagatgattc aaagaacacg   240
ctgtatctac aaatgagcag cctgaaaccc gaggacacag ccctctatta ctgtattgca   300
```

```
gtaactccag acttttacta ttggggccag ggagtcctgg tcaccgtctc ctca        354
```

<210> SEQ ID NO 32
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Gln Ser Gly Gly Gly Leu Val Gln Pro Gly Gly
1               5                   10                  15

Ser Met Arg Leu Ser Cys Glu Ala Ser Gly Leu Ser Leu Ser Asp Tyr
            20                  25                  30

Phe Met His Trp Val Arg Gln Ala Gln Gly Lys Gly Leu Glu Trp Ile
        35                  40                  45

Gly Leu Ile Gln Thr Lys Ala Phe Thr Tyr Lys Thr Glu Tyr Pro Ala
    50                  55                  60

Ala Val Lys Gly Arg Phe Thr Ile Ser Arg Asp Asp Ser Lys Asn Thr
65                  70                  75                  80

Leu Tyr Leu Gln Met Ser Ser Leu Lys Pro Glu Asp Thr Ala Leu Tyr
                85                  90                  95

Tyr Cys Ile Ala Val Thr Pro Asp Phe Tyr Tyr Trp Gly Gln Gly Val
            100                 105                 110

Leu Val Thr Val Ser Ser
        115

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Leu Ser Leu Ser Asp Tyr Phe Met His
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Gln Thr Lys Ala Phe Thr Tyr Lys Thr
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ile Ala Val Thr Pro Asp Phe Tyr Tyr
1               5

<210> SEQ ID NO 36
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
gatgttgtga tgactcagtc tccatctttc ctgtctgcat ctgtaggaga cagagtcacc    60
atcacttgca gggcaagtca ggacattacc attaatttaa attggtttca gcataaacca   120
ggaaaagctc ctaagcgcct gatctatgtt gcatctagat tggaaagggg ggtcccatca   180
aggttcagtg gcagtggatc tgggacagaa ttcactctca ctatcagcag ccttcagcct   240
gaagattttg caacttatta ctgtcaacaa tataataatt accctctcac tttcggcccc   300
gggaccaaac tggatatcaa acgtacggtg                                     330
```

<210> SEQ ID NO 37
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Asp Val Val Met Thr Gln Ser Pro Ser Phe Leu Ser Ala Ser Val Gly
1               5                   10                  15

Asp Arg Val Thr Ile Thr Cys Arg Ala Ser Gln Asp Ile Thr Ile Asn
            20                  25                  30

Leu Asn Trp Phe Gln His Lys Pro Gly Lys Ala Pro Lys Arg Leu Ile
        35                  40                  45

Tyr Val Ala Ser Arg Leu Glu Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Pro Gly Thr Lys Leu Asp Ile Lys Arg Thr Val
            100                 105                 110
```

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Gln Asp Ile Thr Ile Asn
1               5
```

<210> SEQ ID NO 39
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Ala Ser
1

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Tyr Asn Asn Tyr Pro Leu Thr
1               5

<210> SEQ ID NO 41
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
caggtgcagc tgcaggagtc gggcccagga ctggtgaagc cttcggagac cctgtccctc      60
acctgcgctg tctctggttt ctccatcagc agtggttatg ctggagctg  atccgccag     120 cccccaggga aggggctgga gtggattggc tatatcgggg gtagtagtgg tagcaccagc    180
tacaacccct ccctcaagag tcgagtcacc ctgtcagcag acacgtccaa gaatcagttc    240
tccctgaaac tgagctctgt gaccgccgcg gacacggccg tgtattactg cgagaagg     300 tatagttctt atcggagctg gttcgatgtc tggggcccgg gagtcctggt caccgtctcc    360
tca                                                                  363

<210> SEQ ID NO 42
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Glu Ser Gly Pro Gly Leu Val Lys Pro Ser Glu
1               5                   10                  15

Thr Leu Ser Leu Thr Cys Ala Val Ser Gly Phe Ser Ile Ser Ser Gly
            20                  25                  30

Tyr Gly Trp Ser Trp Ile Arg Gln Pro Pro Gly Lys Gly Leu Glu Trp
        35                  40                  45

Ile Gly Tyr Ile Gly Gly Ser Ser Gly Ser Thr Ser Tyr Asn Pro Ser
    50                  55                  60

Leu Lys Ser Arg Val Thr Leu Ser Ala Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Tyr Ser Ser Tyr Arg Ser Trp Phe Asp Val Trp Gly
            100                 105                 110

Pro Gly Val Leu Val Thr Val Ser Ser
        115                 120

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Phe Ser Ile Ser Ser Gly Tyr Gly Trp Ser
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Gly Gly Ser Ser Gly Ser Thr Ser
1               5

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Arg Arg Tyr Ser Ser Tyr Arg Ser Trp Phe Asp Val
1               5                   10

<210> SEQ ID NO 46
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
tcctctgggc tgactcagcc acgctcagtg tccgtgtccc caggacagac ggccaggatc      60
acctgtgggg gagacaacat tggaagtaaa agtgtgcact ggtaccagca gaagccaccg     120
caggcccctg tgctggtcat ctatgctgat agcgaacggc cctcagggat ccctgagcga     180
ttctctggct ccaactcagg gaacaccgcc accctgacca tcagcggggt cgaggccggg     240
gatgaggctg actattactg tcaggtgtgg gacagtagta gtgatcattg ggtattcgga     300
ggagggaccc ggctgaccgt cctt                                            324

<210> SEQ ID NO 47
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ser Ser Gly Leu Thr Gln Pro Arg Ser Val Ser Val Ser Pro Gly Gln
1               5                   10                  15

Thr Ala Arg Ile Thr Cys Gly Gly Asp Asn Ile Gly Ser Lys Ser Val
            20                  25                  30

His Trp Tyr Gln Gln Lys Pro Pro Gln Ala Pro Val Leu Val Ile Tyr
        35                  40                  45

Ala Asp Ser Glu Arg Pro Ser Gly Ile Pro Glu Arg Phe Ser Gly Ser
 50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Arg Leu Thr Val Leu
            100                 105

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asn Ile Gly Ser Lys Ser
1               5

<210> SEQ ID NO 49
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Asp Ser
1

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Val Trp Asp Ser Ser Ser Asp His Trp Val
1               5                   10

<210> SEQ ID NO 51
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gaggtgcagc tggtgcagtc tggagcagag gtgaaaaggc ccggggaatc tctgacgatc      60
tcctgtaaga cttctggata cagctttacc aactactgga tcagctgggt gcgccagatg    120
cccggagaag gcctggagtg gatgggggcg attgatccta gtgattctga taccagatat    180
agcccgtcct tccaaggcca ggtcaccatg tcagccgaca gtccatcac caccgcctac    240

```
ctgcagtgga gcagcctgaa ggcctcggac actgccacgt attactgtgt gaaaggaagt    300
gagacctggg gccagggagt cctggtcacc gtctcctca                           339
```

<210> SEQ ID NO 52
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Val Gln Ser Gly Ala Glu Val Lys Arg Pro Gly Glu
1               5                   10                  15

Ser Leu Thr Ile Ser Cys Lys Thr Ser Gly Tyr Ser Phe Thr Asn Tyr
            20                  25                  30

Trp Ile Ser Trp Val Arg Gln Met Pro Gly Glu Gly Leu Glu Trp Met
        35                  40                  45

Gly Ala Ile Asp Pro Ser Asp Ser Asp Thr Arg Tyr Ser Pro Ser Phe
    50                  55                  60

Gln Gly Gln Val Thr Met Ser Ala Asp Lys Ser Ile Thr Thr Ala Tyr
65                  70                  75                  80

Leu Gln Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Tyr Ser Phe Thr Asn Tyr Trp Ile Ser
1               5                   10

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Asp Pro Ser Asp Ser Asp Thr Arg
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Val Lys Gly Ser Glu Thr
1               5

```
<210> SEQ ID NO 56
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
cagcctgtgc tgactcagcc ggcctccctc tcagcatctc ctggagcatc agccagtctc     60
acatgtacct tcagcggtgg catcaatgtt gctggctaca acatactctg gtaccagcag    120
aaggcaggga gtcctccccg gtatcttctg aggtacaaat cagactcaac taaggaccag    180
ggctctggag tccccagccg cttctctgga tccaaagatg cttcagcgaa cacaggaatt    240
ttacgcatct ctgggctcca gtctgaggat gaggctgact attactgtgc cattgggcac    300
agcagcggtt ggatattcgg aggagggacc cggctcaccg tcctc                    345

<210> SEQ ID NO 57
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Pro Val Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Asn Ile Leu Trp Tyr Gln Gln Lys Ala Gly Ser Pro Pro Arg Tyr
        35                  40                  45

Leu Leu Arg Tyr Lys Ser Asp Ser Thr Lys Asp Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Ile Phe Gly Gly Thr Arg Leu
            100                 105                 110

Thr Val Leu
        115

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Ile Asn Val Ala Gly Tyr Asn
1               5

<210> SEQ ID NO 59
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 59

Tyr Lys Ser Asp Ser Thr Lys
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Ile Gly His Ser Ser Gly Trp Ile
1               5

<210> SEQ ID NO 61
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gaggtgcagc tggtgcagtc tggagcagag gtgaaaaggc ccggggaatc tctgacgatc      60
tcctgtaaga cttctggata tagtttttacc gacagctgga tcggctgggt gcgccagatg    120
cccgggaaag gcctagagtg gatggggagc atctatcctg gtgattctga taccaaatac    180
aacccgtcct tccaaggcca cgtcactatc tcagccgaca gtccatcag caccacctac     240 ctgcagtgga gcagcctgaa ggcctcggac actgccacgt attactgtgt ggctcgtgaa    300
gcctactggg gccagggagt cctggtcacc gtctcctca                           339

<210> SEQ ID NO 62
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Gln Ser Gly Ala Glu Val Lys Arg Pro Gly Glu
1               5                   10                  15

Ser Leu Thr Ile Ser Cys Lys Thr Ser Gly Tyr Ser Phe Thr Asp Ser
            20                  25                  30

Trp Ile Gly Trp Val Arg Gln Met Pro Gly Lys Gly Leu Glu Trp Met
        35                  40                  45

Gly Ser Ile Tyr Pro Gly Asp Ser Asp Thr Lys Tyr Asn Pro Ser Phe
    50                  55                  60

Gln Gly His Val Thr Ile Ser Ala Asp Lys Ser Ile Ser Thr Thr Tyr
65                  70                  75                  80

Leu Gln Trp Ser Ser Leu Lys Ala Ser Asp Thr Ala Thr Tyr Tyr Cys
                85                  90                  95

Val Ala Arg Glu Ala Tyr Trp Gly Gln Gly Val Leu Val Thr Val Ser
            100                 105                 110

Ser

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Gly Tyr Ser Phe Thr Asp Ser Trp Ile Gly
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Ile Tyr Pro Gly Asp Ser Asp Thr Lys
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Val Ala Arg Glu Ala Tyr
1               5

<210> SEQ ID NO 66
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66
cagcctgtgc tgactcagcc agcctccctc tcagcatctc ctggagcatc agccagtctc      60
acatgcacct tcagcggtgg catcaatgtt gctggctacc acatattctg gtaccagcag     120
aagccaggga gtcctccccg gtatcttctg aggtacaaat cagactcaga taagggccag     180
ggctctggag tccccagccg cttctctgga tccaaagatg cttcagcgaa cacagggatt     240
ttacgcatct ctgggctcca gtctgaggat gaggctgact attactgtgc cattgggcac     300
agcagcggcg tgttattcgg aggagggacc cggctgaccg tcctc                     345

<210> SEQ ID NO 67
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Gln Pro Val Leu Thr Gln Pro Ala Ser Leu Ser Ala Ser Pro Gly Ala
1               5                   10                  15

```
Ser Ala Ser Leu Thr Cys Thr Phe Ser Gly Gly Ile Asn Val Ala Gly
            20                  25                  30

Tyr His Ile Phe Trp Tyr Gln Gln Lys Pro Ser Pro Pro Arg Tyr
        35                  40                  45

Leu Leu Arg Tyr Lys Ser Asp Ser Asp Lys Gly Gln Gly Ser Gly Val
 50                  55                  60

Pro Ser Arg Phe Ser Gly Ser Lys Asp Ala Ser Ala Asn Thr Gly Ile
65                   70                  75                  80

Leu Arg Ile Ser Gly Leu Gln Ser Glu Asp Glu Ala Asp Tyr Tyr Cys
                85                  90                  95

Ala Ile Gly His Ser Ser Gly Val Leu Phe Gly Gly Gly Thr Arg Leu
            100                 105                 110

Thr Val Leu
        115

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Gly Ile Asn Val Ala Gly Tyr His
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Tyr Lys Ser Asp Ser Asp Lys
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Ile Gly His Ser Ser Gly Val Leu
1               5

<210> SEQ ID NO 71
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gaggtgcagc tggtgcagtc tggagcagag gtgaaaaggc ccggggaatc tctgacgatc     60
tcctgtaaga cttctggata cagctttacc gacagctggg tcgcctgggt gcgccagatg    120
cccgggaaag gcctggagtg gatggggagt atctatcctg gtgattctga taccagatac    180
```

```
aacccgtcct tcgaaggcca ggtcactatc tcagccgaca agtccatcag caccacctac    240
ctacagtgga gtagcctgag ggcctcggac actgccacgt attactgtgt gaaaggtgcg    300
gacgactggg gccagggagt cctggtcacc gtctcctca                           339
```

```
<210> SEQ ID NO 72
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Gln Ser Gly Ala Glu Val Lys Arg Pro Gly Glu
1               5                   10                  15

Ser Leu Thr Ile Ser Cys Lys Thr Ser Gly Tyr Ser Phe Thr Asp Ser
            20                  25                  30

Trp Val Ala Trp Val Arg Gln Met Pro Gly Lys Gly Leu Glu Trp Met
        35                  40                  45

Gly Ser Ile Tyr Pro Gly Asp Ser Asp Thr Arg Tyr Asn Pro Ser Phe
    50                  55                  60

Glu Gly Gln Val Thr Ile Ser Ala Asp Lys Ser Ile Ser Thr Thr Tyr
65                  70                  75                  80

Leu Gln Trp Ser Ser Leu Arg Ala Ser Asp Thr Ala Thr Tyr Tyr Cys
                85                  90                  95

Val Lys Gly Ala Asp Asp Trp Gly Gln Gly Val Leu Val Thr Val Ser
            100                 105                 110

Ser

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Tyr Ser Phe Thr Asp Ser Trp Val Ala
1               5                   10

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Tyr Pro Gly Asp Ser Asp Thr Arg
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75
```

Val Lys Gly Ala Asp Asp
1               5

<210> SEQ ID NO 76
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
cagcctgtgc tgactcagcc agcctccctc tcagcatctc ctggagcatc agccagtctc    60
acatgtacct tcagcggtgg catcaatgtt gctggctaca acatactctg gtaccagcag   120
aaggcaggga gtcctccccg gtatcttctg aggtacaaat cagactcaac taaggaccag   180
ggctctggag tccccagccg cttctctgga tccaaagatg cttcagcgaa cacaggaatt   240
ttacgcatct ctgggctcca gtctgaggat gaggctgact attactgtgc cattgggcac   300
agcagcggtt ggatattcgg aggagggacc cggctgaccg tcctc                   345

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
gaggtgcagc tggtgcagtc tggggcagag gtgaaaaggc ccggggaatc tctgacgatc    60
tcctgtaaga cttctggata cagctttacc gacagctggg tcgcctgggt gcgccagatg   120
cccgggaaag gctggagtg gttgggagc atctatcctg gtgattctga aacgaaatac   180
aacccgtcct tccaaggcca cgtcactatc tcagccgaca gtccgtcac caccacctac   240 ctgaagtgga gcagcctgaa ggcctcggac actgccacgt attactgtgt gaaaggaagt   300
gagacctggg gccagggagt cctggtcacc gtctcctca                          339

<210> SEQ ID NO 82
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Glu Val Gln Leu Val Gln Ser Gly Ala Glu Val Lys Arg Pro Gly Glu
1               5                   10                  15

Ser Leu Thr Ile Ser Cys Lys Thr Ser Gly Tyr Ser Phe Thr Asp Ser
            20                  25                  30

Trp Val Ala Trp Val Arg Gln Met Pro Gly Lys Gly Leu Glu Trp Leu
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser
```

<210> SEQ ID NO 83

<400> SEQUENCE: 83

000

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

```
Ile Tyr Pro Gly Asp Ser Glu Thr Lys
1               5
```

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

```
Val Lys Gly Ser Glu Thr
1               5
```

<210> SEQ ID NO 86
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86

```
cagcttgtgc tgactcagcc agcctccctc tcagcatctc ctggagcatc agccagtctc    60
acatgtacct tcagcggtgg catcaatgtt gctggctaca acatactctg gtaccagcag   120
aaggcaggga gtcctccccg gtatcttctg aggtacaaat cagactcaac taaggaccag   180
ggctctggag tccccagccg cttctctgga tccaaagatg cttcagcgaa cacaggaatt   240
ttacgcatct ctgggctcca gtctgaggat gaggctgact attactgtgc cattgggcac   300
agcagcggtt ggatattcgg aggagggacc cggctcaccg tcctc                   345
```

<210> SEQ ID NO 87
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Gln Leu Val Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Asn Ile Leu Trp Tyr Gln Gln Lys Ala Gly Ser Pro Arg Tyr
        35                  40                  45

Leu Leu Arg Tyr Lys Ser Asp Ser Thr Lys Asp Gln Gly Ser Gly Val
50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Ile Phe Gly Gly Thr Arg Leu
            100                 105                 110

Thr Val Leu
        115
```

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

-continued

```
caggtgcagc tggtgcaatc tggagcagag gtgaaaaggc ccggggagtc tctgaagatc        60
tcctgtcaga cttctggata cagctttacc gacagctggg tcgcctgggt gcgccagatg       120
cccgggaaag ggctggagtg gttggggagc atctatcctg gtgattctga aacgaaatac       180
aacccgtcct tccaaggcca cgtcactatc tcagccgaca gtccatcag caccgcctac        240 ctgcagtgga gcagcctgaa ggcctcggac actgccacgt attactgtgc gaaaggaagt       300
gagacctggg gccaagggct cagggtcacc gtctcttca                              339
```

<210> SEQ ID NO 92
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Val Gln Ser Gly Ala Glu Val Lys Arg Pro Gly Glu
1               5                   10                  15

Ser Leu Lys Ile Ser Cys Gln Thr Ser Gly Tyr Ser Phe Thr Asp Ser
            20                  25                  30

Trp Val Ala Trp Val Arg Gln Met Pro Gly Lys Gly Leu Glu Trp Leu
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Thr Tyr Tyr Cys
                85                  90                  95

Ala Lys Gly Ser Glu Thr Trp Gly Gln Gly Leu Arg Val Thr Val Ser
            100                 105                 110

Ser

<210> SEQ ID NO 93

<400> SEQUENCE: 93

000

<210> SEQ ID NO 94

<400> SEQUENCE: 94

000

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Lys Gly Ser Glu Thr
1               5

<210> SEQ ID NO 96
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

```
caggcagggc tgactcagcc ggcctccctc tcagcatctc ctggagcatc agccagtctc      60
acatgcacct tcagcggtgg catcaatgtt gctggctata acatactctg gtaccagcag     120
aagccaggga gtcctccccg gtatcttctg aggtacaaat cagactcaga taaggaccag     180
ggctctggag tccccagccg cttctctgga tccaaagatg cttcggccaa cacagggatt     240
ttacgcatct ctggcctcca gtctgaggat gaggctgact attactgtgc cattgggcac     300
agcagcggtt ggatattcgg aggagggacc cggctgaccg tcctt                     345
```

<210> SEQ ID NO 97
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Ala Gly Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Asn Ile Leu Trp Tyr Gln Gln Lys Pro Gly Ser Pro Pro Arg Tyr
        35                  40                  45

Leu Leu Arg Tyr Lys Ser Asp Ser Asp Lys Asp Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Ile Phe Gly Gly Gly Thr Arg Leu
            100                 105                 110

Thr Val Leu
        115

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 339
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 101
gaggtgcagc tggtgcagtc tggagcagag gtgaaaaggc ccggggaatc tctgacgatc      60
tcctgtaaga cttctggata cagctttacc gacagctggg tcgcctgggt gcgccagatg    120
cccgggaaag gctggagtg gttggggagc atctatcctg gtgattctga acgaaatac     180 aacccgtcct tccaaggcca cgtcactatc tcagccgaca agtccgtcac caccacctac    240
ctgaagtgga gcagcctgaa ggcctcggac actgccacgt attactgtgt gaaaggaagt    300
gagacctggg gccagggagt cctggtcacc gtctcctca                            339

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
aattttatgc tgactcagcc agcctccctc tcagcatctc ctggagcatc agccagtctc     60
acatgtacct tcagcggtgg catcaatgtt gctggctaca acatactctg gtaccagcag    120
aaggcaggga gtcctccccg gtatcttctg aggtacaaat cagactcaac taaggaccag    180
ggctctggag tccccagccg cttctctgga tccaaagatg cttcagcgaa cacaggaatt    240
ttacgcatct ctgggctcca gtctgaggat gaggctgact attactgtgc cattgggcac    300
agcagcggtt ggatattcgg aggagggacc cggctcaccg tcctc                    345

<210> SEQ ID NO 107
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107
```

```
Asn Phe Met Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Asn Ile Leu Trp Tyr Gln Gln Lys Ala Gly Ser Pro Pro Arg Tyr
        35                  40                  45

Leu Leu Arg Tyr Lys Ser Asp Ser Thr Lys Asp Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Ile Phe Gly Gly Gly Thr Arg Leu
                100                 105                 110

Thr Val Leu
        115
```

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
gaggtgcagc tggtgcagtc tggagcagag gtgaaaaggc ccggggaatc tctgacgatc      60
tcctgtaaga cttctgaata cagctttacc ggcagctgga tcagctgggt gcgccagatg     120
cccgggaaag gctggagtg gatggggagc atctatcctg gtgattctga taccagatac      180
agcccgtcct tccaaggcca ggtcaccatc tcagccgaca gtccgtcac caccacctac      240 ctgaagtgga gcagcctgaa ggcctcggac actgccacgt attactgtgt gaaaggaagt     300
gagacctggg gccagggagt cctggtcacc gtctcctca                            339

<210> SEQ ID NO 112
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Val Gln Leu Val Gln Ser Gly Ala Glu Val Lys Arg Pro Gly Glu
1               5                   10                  15

Ser Leu Thr Ile Ser Cys Lys Thr Ser Glu Tyr Ser Phe Thr Gly Ser
            20                  25                  30

Trp Ile Ser Trp Val Arg Gln Met Pro Gly Lys Gly Leu Glu Trp Met
        35                  40                  45

Gly Ser Ile Tyr Pro Gly Asp Ser Asp Thr Arg Tyr Ser Pro Ser Phe
    50                  55                  60

Gln Gly Gln Val Thr Ile Ser Ala Asp Lys Ser Val Thr Thr Thr Tyr
65              70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Glu Tyr Ser Phe Thr Gly Ser Trp Ile Ser
1               5                   10

<210> SEQ ID NO 114

<400> SEQUENCE: 114

000

<210> SEQ ID NO 115

<400> SEQUENCE: 115

000

<210> SEQ ID NO 116
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
cagcctgtgc tgactcagcc ggcctccctc tcagcatctc ttggagcatc agccagtctc      60
acatgcacct tcagcggtgg catcaatgtt gctggctaca acatattgtg gtaccagcag     120
aagccaggga gtcctccccg gtttcttctg aggtacaaat cagactcaga taacgtccag     180
ggctctggag tccccagcca cttctctgga tccaaagatg cttcaacgaa cacagggatt     240
ttacgcatct ctgggctcca gtctgaggat gaggctgact attactgtgc cattggccac     300
agcagcggtt gggtattcgg aggagggacc cggctgaccg tcctc                     345

<210> SEQ ID NO 117
<211> LENGTH: 115
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 117

Gln Pro Val Leu Thr Gln Pro Ala Ser Leu Ser Ala Ser Leu Gly Ala
1               5                   10                  15

Ser Ala Ser Leu Thr Cys Thr Phe Ser Gly Gly Ile Asn Val Ala Gly
                20                  25                  30

Tyr Asn Ile Leu Trp Tyr Gln Gln Lys Pro Gly Ser Pro Pro Arg Phe
            35                  40                  45

Leu Leu Arg Tyr Lys Ser Asp Ser Asp Asn Val Gln Gly Ser Gly Val
    50                  55                  60

Pro Ser His Phe Ser Gly Ser Lys Asp Ala Ser Thr Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Val Phe Gly Gly Gly Thr Arg Leu
            100                 105                 110

Thr Val Leu
        115

<210> SEQ ID NO 118

<400> SEQUENCE: 118

000

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Tyr Lys Ser Asp Ser Asp Asn
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Ile Gly His Ser Thr Gly Trp Val
1               5

<210> SEQ ID NO 121
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
gaggtgcagc tggtgcagtc tggagcagag gtgaaaaggc ccggggagtc tctgaagatc    60
```

```
tcctgtaaga cttctggata caccttacc agcagctgga tcagctgggt gcgccagatg    120
cccgggaaag gcctggagtg gttggggagc atctatcctg gtgattctga tacgagatac    180
aacccgtcct tccaaggcca cgtcactatc tcagccgaca cgtccatcat caccacccac    240
ctgcagtgga gcagcctgaa ggcctcggac actgccacgt attactgtgt gaaaggaagt    300
gagacctggg gccagggagt cctggtcacc gtctcctca                           339
```

```
<210> SEQ ID NO 122
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Val Gln Leu Val Gln Ser Gly Ala Glu Val Lys Arg Pro Gly Glu
1               5                   10                  15

Ser Leu Lys Ile Ser Cys Lys Thr Ser Gly Tyr Thr Phe Thr Ser Ser
            20                  25                  30

Trp Ile Ser Trp Val Arg Gln Met Pro Gly Lys Gly Leu Glu Trp Leu
        35                  40                  45

Gly Ser Ile Tyr Pro Gly Asp Ser Asp Thr Arg Tyr Asn Pro Ser Phe
    50                  55                  60

Gln Gly His Val Thr Ile Ser Ala Asp Thr Ser Ile Ile Thr Thr His
65                  70                  75                  80

Leu Gln Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser
```

```
<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Tyr Ser Phe Thr Ser Ser Trp Ile Ser
1               5                   10
```

```
<210> SEQ ID NO 124

<400> SEQUENCE: 124

000
```

```
<210> SEQ ID NO 125

<400> SEQUENCE: 125

000
```

```
<210> SEQ ID NO 126
<211> LENGTH: 345
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 126

```
aagcctatgc tgactcagcc aacctccctc tcagcatctc ctggagcatc agccagtctc      60
acatgtacct tcagcggtgg catcaatgtt gctggctaca acatactctg gtaccagcag     120
aaggcaggga gtcctccccg gtatcttctg aggtacaaat cagactcaac taaggaccag     180
ggctctggag tccccagccg cttctctgga tccaaagatg cttcagcgaa cacaggaatt     240
ttacgcatct ctgggctcca gtctgaggat gaggctgact attactgtgc cattgggcac     300
agcagcggtt ggatattcgg aggagggacc cggctgaccg tcctc                     345
```

<210> SEQ ID NO 127
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Lys Pro Met Leu Thr Gln Pro Thr Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Asn Ile Leu Trp Tyr Gln Gln Lys Ala Gly Ser Pro Arg Tyr
        35                  40                  45

Leu Leu Arg Tyr Lys Ser Asp Ser Thr Lys Asp Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Ile Phe Gly Gly Gly Thr Arg Leu
            100                 105                 110

Thr Val Leu
        115
```

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131

```
gaggtgcagc tggtgcagtc tggagcagag gtgaaaaggc ccggggagtc tctgaagatc      60
tcctgtcaga cttctggata cagctttacc agcacctgga tcacctgggt gcgccagatg    120
cccgggaaag ggctggagtg gttggggagc atctatcctg gtgattctga aacgaaatac    180
aacccgtcct ccaaggcca cgtcaccatt tcagccgaca agtccatcag caccacctac    240
ctgcagtgga acagcctgaa ggcctcggac actgccacgt attactgtgt gaaaggaagt    300
gagacctggg gccagggagt cctggtcacc gtctcctca                           339
```

<210> SEQ ID NO 132
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Glu Val Gln Leu Val Gln Ser Gly Ala Glu Val Lys Arg Pro Gly Glu
1               5                   10                  15
Ser Leu Lys Ile Ser Cys Gln Thr Ser Gly Tyr Ser Phe Thr Ser Thr
            20                  25                  30
Trp Ile Thr Trp Val Arg Gln Met Pro Gly Lys Gly Leu Glu Trp Leu
        35                  40                  45
Gly Ser Ile Tyr Pro Gly Asp Ser Glu Thr Lys Tyr Asn Pro Ser Phe
    50                  55                  60
Gln Gly His Val Thr Ile Ser Ala Asp Lys Ser Ile Ser Thr Thr Tyr
65                  70                  75                  80
Leu Gln Trp Asn Ser Leu Lys Ala Ser Asp Thr Ala Thr Tyr Tyr Cys
                85                  90                  95
Val Lys Gly Ser Glu Thr Trp Gly Gln Gly Val Leu Val Thr Val Ser
            100                 105                 110
Ser
```

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

```
Gly Tyr Ser Phe Thr Ser Thr Trp Ile Thr
1               5                   10
```

<210> SEQ ID NO 134

<400> SEQUENCE: 134

000

<210> SEQ ID NO 135

<400> SEQUENCE: 135

000

```
<210> SEQ ID NO 136
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
caggctgtgg tgactcagcc agcctccctc tcagcatctc ctggagcatc agccagtctc      60
acatgtacct tcagcggtgg catcaatgtt gctggctaca acatactctg gtaccagcag     120
aaggcaggga gtcctccccg gtatcttctg aggtacaaat cagactcaac taaggaccag     180
ggctctggag tccccagccg cttctctgga tccaaagatg cttcagcgaa cacaggaatt     240
ttacgcatct ctgggctcca gtctgaggat gaggctgact attactgtgc cattgggcac     300
agcagcggtt ggatattcgg aggagggacc cggctgaccg tcctc                    345

<210> SEQ ID NO 137
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Ala Val Val Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Asn Ile Leu Trp Tyr Gln Gln Lys Ala Gly Ser Pro Pro Arg Tyr
        35                  40                  45

Leu Leu Arg Tyr Lys Ser Asp Ser Thr Lys Asp Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Ile Phe Gly Gly Gly Thr Arg Leu
            100                 105                 110

Thr Val Leu
        115

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000
```

<210> SEQ ID NO 141
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
caggtgcagc tggtgcagtc tggagcagag gtgaaaaggc ccggggaatc tctgaggatc      60
tcctgtaaga cttctggata caccttttacc gactactgga tcgcctgggt gcgccagatg    120
cccggaaaag gcctggagtg gatggggagc atctatcctg gtgattctga acgaaatac     180 aacccgtcct tccaaggcca cgtcactatc tcagccgaca gtccgtcac caccacctac     240 ctgaagtgga gccgcctgaa ggcctcggac actgccacgt attactgtgt gaaaggaagt    300
gagacctggg gccagggagt cctggtcacc gtctcctca                           339

<210> SEQ ID NO 142
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Val Gln Leu Val Gln Ser Gly Ala Glu Val Lys Arg Pro Gly Glu
1               5                   10                  15

Ser Leu Arg Ile Ser Cys Lys Thr Ser Gly Tyr Thr Phe Thr Asp Tyr
            20                  25                  30

Trp Ile Ala Trp Val Arg Gln Met Pro Gly Lys Gly Leu Glu Trp Met
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Arg Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Tyr Thr Phe Thr Asp Tyr Trp Ile Ala
1               5                   10

<210> SEQ ID NO 144

<400> SEQUENCE: 144

000

<210> SEQ ID NO 145

<400> SEQUENCE: 145

000

<210> SEQ ID NO 146
<211> LENGTH: 345
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 146
cagcctgtgc tgactcagcc agcctccctc tcagcatctc ctggagcatc agccagtctc      60
acatgtacct tcagcggtgg catcaatgtt gctggctaca acatactctg gtaccagcag     120
aaggcaggga gtcctccccg gtatcttctg aggtacaaat cagactcaac taaggaccag     180
ggctctggag tccccagccg cttctctgga tccaaagatg cttcagcgaa cacaggaatt     240
ttacgcatct ctgggctcca gtctgaggat gaggctgact attactgtgc cattgggcac     300
agcagcggtt ggatattcgg aggagggacc cggctgaccg tcctc                    345

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151
<211> LENGTH: 339
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 151
gaggtgcagc tggtgcagtc tggagcagag gtgaaaaggc ccggggagtc tctaaagatc      60
tcctgtagga cttctggata cagctttacc agtacctgga tcaactgggt gcgccagatg     120
cccgggaaag gcctggagtg gttggggagc atctatcctg gtgattctga acgaaatac      180 aacccgtcct tccaaggcca cgtcactatc tcagccgaca gtccgtcac caccacctac     240 ctgaagtgga gcagcctgaa ggcctcggac actgccacgt attactgtgt gaaaggaagt     300
gagacctggg gccagggagt cctggtcacc gtctcctca                           339

<210> SEQ ID NO 152
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Glu Val Gln Leu Val Gln Ser Gly Ala Glu Val Lys Arg Pro Gly Glu
1               5                   10                  15

Ser Leu Lys Ile Ser Cys Arg Thr Ser Gly Tyr Ser Phe Thr Ser Thr
            20                  25                  30

Trp Ile Asn Trp Val Arg Gln Met Pro Gly Lys Gly Leu Glu Trp Leu
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Tyr Ser Phe Thr Ser Thr Trp Ile Asn
1               5                   10

<210> SEQ ID NO 154

<400> SEQUENCE: 154

000

<210> SEQ ID NO 155

<400> SEQUENCE: 155

000

<210> SEQ ID NO 156
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
aagcctatgc tgactcagcc agcctccctc tcagcatctc ctggagcatc agccagtctc     60
acatgtacct tcagcggtgg catcaatgtt gctggctaca acatactctg gtaccagcag    120
aaggcaggga gtcctccccg gtatcttctg aggtacaaat cagactcaac taaggaccag    180

```
ggctctggag tccccagccg cttctctgga tccaaagatg cttcagcgaa cacaggaatt    240
ttacgcatct ctgggctcca gtctgaggat gaggctgact attactgtgc cattgggcac    300
agcagcggtt gggtcttcgg aggagggacc cggctgaccg tcctc                    345
```

<210> SEQ ID NO 157
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

```
Lys Pro Met Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Asn Ile Leu Trp Tyr Gln Gln Lys Ala Gly Ser Pro Pro Arg Tyr
        35                  40                  45

Leu Leu Arg Tyr Lys Ser Asp Ser Thr Lys Asp Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Val Phe Gly Gly Gly Thr Arg Leu
            100                 105                 110

Thr Val Leu
        115
```

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161

```
gaggtgcagc tggtgcagtc tggagcagag gtgaaaaggc ccggggaatc tctgacgatc     60
tcctgtaaga cttctggata cagttttacc gacagctgga tcagctgggt gcgccagatg    120
cccgggaaag gcctggagtg gatggggagc atctatcctg gtgattctga tgccagatac    180
```

```
aacccgtcct tccaaggcca cgtcactatc tcggccgaca agtccatcag caccacctac    240
ctgaagtgga gcagcctgaa ggcctcggac actgccacgt attactgtgt gaaaggaagt    300
gagacctggg gccagggagt cctggtcacc gtctcctca                           339
```

<210> SEQ ID NO 162
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

```
Glu Val Gln Leu Val Gln Ser Gly Ala Glu Val Lys Arg Pro Gly Glu
1               5                   10                  15

Ser Leu Thr Ile Ser Cys Lys Thr Ser Gly Tyr Ser Phe Thr Asp Ser
            20                  25                  30

Trp Ile Ser Trp Val Arg Gln Met Pro Gly Lys Gly Leu Glu Trp Met
        35                  40                  45

Gly Ser Ile Tyr Pro Gly Asp Ser Asp Ala Arg Tyr Asn Pro Ser Phe
    50                  55                  60

Gln Gly His Val Thr Ile Ser Ala Asp Lys Ser Ile Ser Thr Thr Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser
```

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

```
Gly Tyr Ser Phe Thr Asp Ser Trp Ile Ser
1               5                   10
```

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

```
Ile Tyr Pro Gly Asp Ser Asp Ala Arg
1               5
```

<210> SEQ ID NO 165

<400> SEQUENCE: 165

000

<210> SEQ ID NO 166
<211> LENGTH: 345
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 166

```
caggctgtgg tgactcagcc agcctccctc tcagcatctc ctggaacatc agccagtctc    60
acatgcacct tcagcggtgg catcaatgtt gctggctaca acatattgtg gtaccagcag   120
aagccaggga gtcctccccg gtttcttctg aggtacaaat cagactcaga taacgtccag   180
ggctctggag tccccagcca cttctctgga tccaaagatg cttcagcgaa cacagggatc   240
ttacgcatct ctgggctcca gtctgaggat gaggctgact attactgtgc cattgggcac   300
agcagcggtt ggatattcgg aggagggacc cggctgaccg tcctc                   345
```

<210> SEQ ID NO 167
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

Gln Ala Val Val Thr Gln Pro Ala Ser Leu Ser Ala Ser Pro Gly Thr
1               5                   10                  15
Ser Ala Ser Leu Thr Cys Thr Phe Ser Gly Gly Ile Asn Val Ala Gly
                20                  25                  30
Tyr Asn Ile Leu Trp Tyr Gln Gln Lys Pro Gly Ser Pro Pro Arg Phe
            35                  40                  45
Leu Leu Arg Tyr Lys Ser Asp Ser Asp Asn Val Gln Gly Ser Gly Val
        50                  55                  60
Pro Ser His Phe Ser Gly Ser Lys Asp Ala Ser Ala Asn Thr Gly Ile
65                  70                  75                  80
Leu Arg Ile Ser Gly Leu Gln Ser Glu Asp Glu Ala Asp Tyr Tyr Cys
                85                  90                  95
Ala Ile Gly His Ser Ser Gly Trp Ile Phe Gly Gly Gly Thr Arg Leu
            100                 105                 110
Thr Val Leu
        115

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171
<211> LENGTH: 339
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 171

```
caggtgcagc tggtgcaatc tggagcagag gtgaaaaggc ccggggagtc tctgaagatc      60
tcctgtaaga cttctggata cagctttacc aacatctgga tcagttgggt gcgccagatg     120
cccgggaaag gctggagtg gttggggagc atctatcctg gtgattctga acgaaatac       180
aacccgtcct tccaaggcca cgtcactatc tcagccgaca agtccgtcac caccacctac     240
ctgaagtgga gcagcctgaa ggcctcggac actgccacgt attactgtgt gaaaggaagt     300
gagacctggg gccagggagt cctggtcacc gtctcctca                            339
```

<210> SEQ ID NO 172
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

```
Gln Val Gln Leu Val Gln Ser Gly Ala Glu Val Lys Arg Pro Gly Glu
1               5                   10                  15
Ser Leu Lys Ile Ser Cys Lys Thr Ser Gly Tyr Ser Phe Thr Asn Ile
            20                  25                  30
Trp Ile Ser Trp Val Arg Gln Met Pro Gly Lys Gly Leu Glu Trp Leu
        35                  40                  45
Gly Ser Ile Tyr Pro Gly Asp Ser Glu Thr Lys Tyr Asn Pro Ser Phe
    50                  55                  60
Gln Gly His Val Thr Ile Ser Ala Asp Lys Ser Val Thr Thr Thr Tyr
65                  70                  75                  80
Leu Lys Trp Ser Ser Leu Lys Ala Ser Asp Thr Ala Thr Tyr Tyr Cys
                85                  90                  95
Val Lys Gly Ser Glu Thr Trp Gly Gln Gly Val Leu Val Thr Val Ser
            100                 105                 110
Ser
```

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

```
Gly Tyr Ser Phe Thr Asn Ile Trp Ile Ser
1               5                   10
```

<210> SEQ ID NO 174

<400> SEQUENCE: 174

000

<210> SEQ ID NO 175

<400> SEQUENCE: 175

-continued

000

<210> SEQ ID NO 176
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176

```
aattttatgc tgactcagcc ggcctccctc tcagcatctc ctggagcatc agccagtctc      60
acatgcacct tcagcggtgg catcaatgtt gctggctacc acatattgtg gtatcagcag     120
aagccaggga gtcctccccg gtatcttctg aggtataaat cagactcaga gaaggaccag     180
ggctctggag tccccagccg cttctctgga tccaaagatg cttcggccaa cagagggatt     240
ttacgcatct ctgggctcca gtctgaagat gaggctgact attactgtgc cattgggcac     300
agtagtagcg gttgggtatt cggaggaggg acccggctga ccgtcctc                  348
```

<210> SEQ ID NO 177
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Asn Phe Met Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr His Ile Leu Trp Tyr Gln Gln Lys Pro Gly Ser Pro Pro Arg Tyr
        35                  40                  45

Leu Leu Arg Tyr Lys Ser Asp Ser Glu Lys Asp Gln Gly Ser Gly Val
    50                  55                  60

Pro Ser Arg Phe Ser Gly Ser Lys Asp Ala Ser Ala Asn Arg Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Ser Gly Trp Val Phe Gly Gly Gly Thr Arg
            100                 105                 110

Leu Thr Val Leu
        115

<210> SEQ ID NO 178

<400> SEQUENCE: 178

000

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Tyr Lys Ser Asp Ser Glu Lys

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 180

Ala Ile Gly His Ser Ser Ser Gly Trp Val
1               5                   10

<210> SEQ ID NO 181
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 181
caggtgcagc tggtgcagtc tggagcagag gtgaaaaggc ccggggaatc tctgacgatc      60
tcctgtaaga cttctggata cagctttacc gacagctggg tcgcctgggt gcgccagatg     120
cccgggaaag gctggagtg gttggggagc atctatcctg gtgattctga taccaaatac     180
aacccgtcct tccaaggcca cgtcactatc tcagccgaca gtccgtcac caccacctac      240 ctgaagtgga gcagcctgaa ggcctcggac actgccacgt attactgtgt gaaaggaagt     300
gagacctggg gccagggagt cctggtcacc gtctcctca                            339

<210> SEQ ID NO 182
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

Gln Val Gln Leu Val Gln Ser Gly Ala Glu Val Lys Arg Pro Gly Glu
1               5                   10                  15

Ser Leu Thr Ile Ser Cys Lys Thr Ser Gly Tyr Ser Phe Thr Asp Ser
            20                  25                  30

Trp Val Ala Trp Val Arg Gln Met Pro Gly Lys Gly Leu Glu Trp Leu
        35                  40                  45

Gly Ser Ile Tyr Pro Gly Asp Ser Asp Thr Lys Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186
<211> LENGTH: 345
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 186

```
aagcctatgc tgactcagcc agcctccctc tcagcatctc ctggagcatc agccagtctc    60
acatgcacct tcagcggtgg catcaatgtt gctggctacc acatattctg gtaccagcag   120
aagccaggga gtcctccccg gtatcttctg aggtataaat cagactcaga taagggccag   180
ggctctggag tccccagccg cttctctgga tccaaagatg cttcagcgaa cacagggatt   240
ttacgcatct ctgggctcca gtctgaggat gaggctgact attactgtgc cattgggcac   300
agcagcggtc tgttattcgg aggagggacc cggctgaccg tcctc                    345
```

<210> SEQ ID NO 187
<211> LENGTH: 115
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 187

```
Lys Pro Met Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr His Ile Phe Trp Tyr Gln Gln Lys Pro Gly Ser Pro Pro Arg Tyr
        35                  40                  45

Leu Leu Arg Tyr Lys Ser Asp Ser Asp Lys Gly Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Leu Leu Phe Gly Gly Thr Arg Leu
            100                 105                 110

Thr Val Leu
        115
```

<210> SEQ ID NO 188

<400> SEQUENCE: 188

000

<210> SEQ ID NO 189

<400> SEQUENCE: 189

000

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ala Ile Gly His Ser Ser Gly Leu Leu
1               5

<210> SEQ ID NO 191
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191
gaggtgcagt tggtggagtc tggagcagag gtgaaaaggc ccggggagtc tctgacgatc    60
tcctgtaaga cttctggata cagctttacc ggcagctgga tcagctgggt gcgccagatg   120
cccgggaaag gcctggagtg gttggggagc atctatcctg gtgattctga acgaaatac    180 aacccgtcct tccaaggcca cgtcactatc tcagccgaca gtccgtcac caccacctac    240 ctgaagtgga gcagcctgaa ggcctcggac actgccacgt attactgtgt gaaaggaagt   300
gagacctggg gccagggagt cctggtcacc gtctcctca                          339

<210> SEQ ID NO 192
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Glu Val Gln Leu Val Glu Ser Gly Ala Glu Val Lys Arg Pro Gly Glu
1               5                   10                  15

Ser Leu Thr Ile Ser Cys Lys Thr Ser Gly Tyr Ser Phe Thr Gly Ser
            20                  25                  30

Trp Ile Ser Trp Val Arg Gln Met Pro Gly Lys Gly Leu Glu Trp Leu
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Tyr Ser Phe Thr Gly Ser Trp Ile Ser
1               5                   10

<210> SEQ ID NO 194

<400> SEQUENCE: 194

000

<210> SEQ ID NO 195

<400> SEQUENCE: 195

000

<210> SEQ ID NO 196
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196
aattttatgc tgactcagtc ggcctccctc tcagcatctc ctggagcatc agccagtctc     60
acatgcacct tcagcggtgg catcaatgtt gctggctacc acatattctg gtaccagcag    120
aacccaggga gtcctccccg ctatcttctg agatacaaat cagactcaga gaaggaccag    180
ggctctggag tccccagccg cttctctgga tccaaagatg cttcagcgaa cacaggaatt    240
ttacgcatct ctgggctcca gtctgaggat gaggctgact attactgtgc cattgggcac    300
agcagcggtt ggatattcgg aggagggacc cggctcaccg tcctc                   345

<210> SEQ ID NO 197
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Asn Phe Met Leu Thr Gln Ser Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr His Ile Phe Trp Tyr Gln Gln Asn Pro Gly Ser Pro Pro Arg Tyr
        35                  40                  45

Leu Leu Arg Tyr Lys Ser Asp Ser Glu Lys Asp Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Ile Phe Gly Gly Gly Thr Arg Leu
            100                 105                 110

Thr Val Leu
        115

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201
gaggtgcagt tggtggagtc tggagcagag gtgaaaaggc ccggggaatc tctgacgatc      60
tcctgtaaga cttctggata cagctttacc gacagctggg tcgcctgggt gcgccagatg    120
cccgggaaag gctggagtg gttggggagc atctatcctg gtgattctga aacgaaatac     180
aacccgtcct tccaaggcca cgtcactatc tcagccgaca gtccatcag caccacctac      240 ctacagtgga gtagcctgag ggcctcggac actgccacgt attactgtgt gaaaggtgcg    300
gacgactggg gcccaggact cctggtcacc gtctcctca                            339

<210> SEQ ID NO 202
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Glu Val Gln Leu Val Glu Ser Gly Ala Glu Val Lys Arg Pro Gly Glu
1               5                   10                  15

Ser Leu Thr Ile Ser Cys Lys Thr Ser Gly Tyr Ser Phe Thr Asp Ser
            20                  25                  30

Trp Val Ala Trp Val Arg Gln Met Pro Gly Lys Gly Leu Glu Trp Leu
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Ile Ser Thr Thr Tyr
65                  70                  75                  80

Leu Gln Trp Ser Ser Leu Arg Ala Ser Asp Thr Ala Thr Tyr Tyr Cys
                85                  90                  95

Val Lys Gly Ala Asp Asp Trp Gly Pro Gly Leu Leu Val Thr Val Ser
            100                 105                 110
Ser

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206
tcctctgagc tgactcagcc agcctccctc tcagcatctc ctggagcatc agccagtctc      60
acatgtacct tcagcggtgg catcaatgtt gctggctaca acatactctg gtaccagcag     120
aaggcaggga gtcctccccg gtatcttctg aggtacaaat cagactcaga taagggccag     180
ggctctggag tccccagccg cttctctgga tccaaagatg cttcagcgaa cacagggatt     240
ttacgcatct ctgggctcca gtctgaggat gaggctgact attactgtgc cattgggcac     300
agcagcggtt ggatattcgg aggagggacc cggctcaccg tcctc                     345

<210> SEQ ID NO 207
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Ser Ser Glu Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Asn Ile Leu Trp Tyr Gln Gln Lys Ala Gly Ser Pro Pro Arg Tyr
        35                  40                  45

Leu Leu Arg Tyr Lys Ser Asp Ser Asp Lys Gly Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

```
Ala Ile Gly His Ser Ser Gly Trp Ile Phe Gly Gly Gly Thr Arg Leu
            100                 105                 110

Thr Val Leu
        115
```

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211

```
gaggtgcagc tggtgcagtc tggagcagag gtgaaaaggc ccggggaatc tctgacgatc      60
tcctgtaaga cttctggata cagctttacc gacagctggg tcgcctgggt gcgccagatg     120
cccgggaaag ggctggagtg gttggggagc atctatcctg gtgattctga acgaaatac     180
aacccgtcct tccaaggcca cgtcactatc tcagccgaca gtccatcag caccgcctac     240
ctgcagtgga gcagcctgaa ggcctcggac accgccacct attactgtgc gaaaggaagt     300
gagacctggg gccagggagt cctggtcacc gtctcctca                           339
```

<210> SEQ ID NO 212
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

```
Glu Val Gln Leu Val Gln Ser Gly Ala Glu Val Lys Arg Pro Gly Glu
1               5                   10                  15

Ser Leu Thr Ile Ser Cys Lys Thr Ser Gly Tyr Ser Phe Thr Asp Ser
            20                  25                  30

Trp Val Ala Trp Val Arg Gln Met Pro Gly Lys Gly Leu Glu Trp Leu
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Thr Tyr Tyr Cys
                85                  90                  95
```

```
Ala Lys Gly Ser Glu Thr Trp Gly Gln Gly Val Leu Val Thr Val Ser
                100                 105                 110

Ser

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 216
tcctccgggc tgactcagcc agcctccctc tcagcatctc ctggagcatc agccagtctc      60
acatgtacct tcagcggtgg catcaatgtt gctggctaca acatactctg gtaccaacag     120
aaggcaggga gtcctccccg gtatcttctg aggtacaaat cagactcaac taaggaccag     180
ggctctggag tccccagccg cttctctgga tccaaagatg cttcagcgaa tacaggaatt     240
ttacgcatct ctgggctcca gtctgaggat gaggctgact attactgtgc cattgggcac     300
agcagcggtt ggatattcgg aggagggacc cggctgaccg tcctc                    345

<210> SEQ ID NO 217
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Ser Ser Gly Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
                20                  25                  30

Tyr Asn Ile Leu Trp Tyr Gln Gln Lys Ala Gly Ser Pro Pro Arg Tyr
            35                  40                  45

Leu Leu Arg Tyr Lys Ser Asp Ser Thr Lys Asp Gln Gly Ser Gly Val
        50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Ile Phe Gly Gly Gly Thr Arg Leu
```

```
                  100                 105                 110

Thr Val Leu
        115

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221
caggtgcagc tggtgcagtc tggagcagag gtgaaaaggc ccggggaatc tctgacgatc      60
tcctgtaaga cttctggata cagctttacc ggcagctgga tcagctgggt gcgccagatg     120
cccgggaaag gcctggagtg gatggggagc atctatcctg gtgattctga taccacatac     180
aatccgtcct tccaaggcca cgtcactatc tcagccgaca agtccatcag taccgcctac     240
ctgcaatgga ctagtctgaa ggcctcggac actgccacgt attactgtgt gaaaggaagt     300
gagacctggg gccagggagt cctggtcacc gtctcctca                            339

<210> SEQ ID NO 222
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Gln Val Gln Leu Val Gln Ser Gly Ala Glu Val Lys Arg Pro Gly Glu
1               5                   10                  15

Ser Leu Thr Ile Ser Cys Lys Thr Ser Gly Tyr Ser Phe Thr Gly Ser
            20                  25                  30

Trp Ile Ser Trp Val Arg Gln Met Pro Gly Lys Gly Leu Glu Trp Met
        35                  40                  45

Gly Ser Ile Tyr Pro Gly Asp Ser Asp Thr Thr Tyr Asn Pro Ser Phe
    50                  55                  60

Gln Gly His Val Thr Ile Ser Ala Asp Lys Ser Ile Ser Thr Ala Tyr
65                  70                  75                  80

Leu Gln Trp Thr Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
```

Ser

<210> SEQ ID NO 223

<400> SEQUENCE: 223

000

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ile Tyr Pro Gly Asp Ser Asp Thr Thr
1               5

<210> SEQ ID NO 225

<400> SEQUENCE: 225

000

<210> SEQ ID NO 226
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 226
tcctatgagc tgacacagcc agcctccctc tcagcatctc ctggagcatc agccagtctc      60
acatgtacct tcagcggtgg catcaatgtt gctggctaca atactctg gtaccagcag       120 aaggcaggga gtcctcccg gtatcttctg aggtacaaat cagactcaac taaggaccag      180
ggctctggag tccccagccg cttctctgga tccaaagatg cttcagcgaa cacagggatc     240
ttacgcatct ctggcctcca gtctgaggat gaggctgact attactgtgc cattggccac     300
agcagcggtc tcatcttcgg tgctgggacc cggctcaccg tcctc                     345

<210> SEQ ID NO 227
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Ser Tyr Glu Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
                20                  25                  30

Tyr Asn Ile Leu Trp Tyr Gln Gln Lys Ala Gly Ser Pro Pro Arg Tyr
            35                  40                  45

Leu Leu Arg Tyr Lys Ser Asp Ser Thr Lys Asp Gln Gly Ser Gly Val
        50                  55                  60

Pro Ser Arg Phe Ser Gly Ser Lys Asp Ala Ser Ala Asn Thr Gly Ile 65                  70                  75                  80
Leu Arg Ile Ser Gly Leu Gln Ser Glu Asp Glu Ala Asp Tyr Tyr Cys
                85                  90                  95
Ala Ile Gly His Ser Ser Gly Leu Ile Phe Gly Ala Gly Thr Arg Leu
            100                 105                 110
Thr Val Leu
        115

<210> SEQ ID NO 228

<400> SEQUENCE: 228

000

<210> SEQ ID NO 229

<400> SEQUENCE: 229

000

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ala Ile Gly His Ser Ser Gly Leu Ile
1               5

<210> SEQ ID NO 231
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231
gaggtgcagc tggtgcagtc tggagcagag gtgaaaaggc ccggggagtc tctgaagatc      60
tcctgtaaga cttctggata cagctttacc gacagctggg tcgcctgggt gcgccagatg     120
cccgggaaag gcctggaatg gatggggagc atctatcctg gtgattttca aacgagatac     180
aacccgtcct tccaaggaca cgtcactctc tcagccgaca gtccatcagc caccacctac     240
ctacagtgga gcagcctgaa ggcctcggac accgccacgt attactgtgt gaaaggaagt     300
gagacctggg gcccgggagt cctggtcacc gtctcctca                            339

<210> SEQ ID NO 232
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Glu Val Gln Leu Val Gln Ser Gly Ala Glu Val Lys Arg Pro Gly Glu
1               5                   10                  15
Ser Leu Lys Ile Ser Cys Lys Thr Ser Gly Tyr Ser Phe Thr Asp Ser
            20                  25                  30

Trp Val Ala Trp Val Arg Gln Met Pro Gly Lys Gly Leu Glu Trp Met
            35                  40                  45

Gly Ser Ile Tyr Pro Gly Asp Phe Gln Thr Arg Tyr Asn Pro Ser Phe
 50                  55                  60

Gln Gly His Val Thr Leu Ser Ala Asp Lys Ser Ile Ser Thr Thr Tyr
65                  70                  75                  80

Leu Gln Trp Ser Ser Leu Lys Ala Ser Asp Thr Ala Thr Tyr Tyr Cys
                85                  90                  95

Val Lys Gly Ser Glu Thr Trp Gly Pro Gly Val Leu Val Thr Val Ser
            100                 105                 110

Ser

<210> SEQ ID NO 233

<400> SEQUENCE: 233

000

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ile Tyr Pro Gly Asp Phe Gln Thr Arg
1               5

<210> SEQ ID NO 235

<400> SEQUENCE: 235

000

<210> SEQ ID NO 236
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 236
tcctccgggc tgactcagcc agcctccctc tcagcatctc ctggagcatc agccagtctc      60
acatgtacct tcagcggtgg catcaatgtt gctggctaca acatactctg gtaccagcag     120
aaggcaggga gtcctccccg gtatcttctg aggtacaaat cagactcaac taaggaccag     180
ggctctggag tccccagccg cttctctgga tccaaagatg tttcagcgaa cacaggcatc     240
ttacgcatct ctgggctcca gtctgacgat gaggctgact attactgtgc cattgggcac     300
agcagcggtt ggatattcgg aggcgggacc cggctgaccg tcctc                     345

<210> SEQ ID NO 237
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

-continued

```
Ser Ser Gly Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Asn Ile Leu Trp Tyr Gln Gln Lys Ala Gly Ser Pro Pro Arg Tyr
        35                  40                  45

Leu Leu Arg Tyr Lys Ser Asp Ser Thr Lys Asp Gln Gly Ser Gly Val
    50                  55                  60

Pro Ser Arg Phe Ser Gly Ser Lys Asp Val Ser Ala Asn Thr Gly Ile
65                  70                  75                  80

Leu Arg Ile Ser Gly Leu Gln Ser Asp Asp Glu Ala Asp Tyr Tyr Cys
                85                  90                  95

Ala Ile Gly His Ser Ser Gly Trp Ile Phe Gly Gly Gly Thr Arg Leu
            100                 105                 110

Thr Val Leu
        115
```

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241

```
gaggtgcagc tggtgcattc tggagcagag gtgaaaaggc ccggggaatc tctgacgatc      60
tcctgtaaga cttctggata caccttacc gactactgga tcgcctgggt gcgccagatg     120
cccgggaaag gctggagtg gatggcgagc atctatcctg atgattctga taccagatac     180
aacccgtcct tccaaggcca cgtcactatc tcagccgaca agtccatcag caccacctac     240
ctacagtgga gtagcctgag ggcctcggac actgccacgt attactgtgt gaaaggaagt     300
gagacctggg gccagggagt cctggtcacc gtctcctca                            339
```

<210> SEQ ID NO 242
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

```
Glu Val Gln Leu Val His Ser Gly Ala Glu Val Lys Arg Pro Gly Glu
1               5                   10                  15

Ser Leu Thr Ile Ser Cys Lys Thr Ser Gly Tyr Thr Phe Thr Asp Tyr
                20                  25                  30

Trp Ile Ala Trp Val Arg Gln Met Pro Gly Lys Gly Leu Glu Trp Met
                35                  40                  45

Ala Ser Ile Tyr Pro Asp Asp Ser Asp Thr Arg Tyr Asn Pro Ser Phe
            50                  55                  60

Gln Gly His Val Thr Ile Ser Ala Asp Lys Ser Ile Ser Thr Thr Tyr
65                  70                  75                  80

Leu Gln Trp Ser Ser Leu Arg Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser
```

<210> SEQ ID NO 243

<400> SEQUENCE: 243

000

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

```
Ile Tyr Pro Asp Asp Ser Asp Thr Arg
1               5
```

<210> SEQ ID NO 245

<400> SEQUENCE: 245

000

<210> SEQ ID NO 246
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 246

```
cagcttgtgc tgactcagcc agcctccctc tcagcatctc ctggaacatc agccagtctc    60
acatgcacct tcagcggtgg catcaatgtt gctggctaca acatattgtg gtaccagcag   120
aagccaggga gtcctccccg gtttcttctg aggtacaaat cagactcaga taacgtccag   180
ggctctggag tccccagcca cttctctgga tccaaagatg cttcaacgaa cacagggatt   240
ttacgcatct ctgggctcca gtctgaggat gaggctgact attactgtgc cattggccac   300
agcagcggtt gggtattcgg aggagggacc cggctgaccg tcctc                   345
```

<210> SEQ ID NO 247
<211> LENGTH: 115
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 247

Gln Leu Val Leu Thr Gln Pro Ala Ser Leu Ser Ala Ser Pro Gly Thr
1               5                   10                  15

Ser Ala Ser Leu Thr Cys Thr Phe Ser Gly Gly Ile Asn Val Ala Gly
                20                  25                  30

Tyr Asn Ile Leu Trp Tyr Gln Gln Lys Pro Gly Ser Pro Pro Arg Phe
            35                  40                  45

Leu Leu Arg Tyr Lys Ser Asp Ser Asp Asn Val Gln Gly Ser Gly Val
    50                  55                  60

Pro Ser His Phe Ser Gly Ser Lys Asp Ala Ser Thr Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Val Phe Gly Gly Thr Arg Leu
            100                 105                 110

Thr Val Leu
        115

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251
caggtgcagc tggtgcagtc tggagcagag gtgaaaaggc ccggggaatc tctgaggatc        60
tcctgtaaga cttctggata cacctttacc gactactgga tcgcctgggt gcgccagatg       120
cccggaaaag gcctggagtg gatggggagc atctatcctg tgattctgaa acgaaatac        180 aacccgtcct tccaaggcca cgtcactatc tcagccgaca gtccgtcac caccacctac        240 ctgaagtgga gccgcctgaa ggcctcggac actgccacgt attactgtgt gaaaggaagt       300
gagacctggg gccagggagt cctggtcacc gtctcctca                              339

<210> SEQ ID NO 252

<400> SEQUENCE: 252
```

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 256

```
cagcctgtgc tgactcagcc agcctccctc tcagcatctc ctggagcatc agccagtctc    60
acatgtacct tcagcggtgg catcaatgtt gctggctaca acatactctg gtaccagcag   120
aaggcaggga gtcctccccg gtatcttctg aggtacaaat cagactcaac taaggaccag   180
ggctctggag tccccagccg cttctctgga tccaaagatg cttcagcgaa cacaggaatt   240
ttacgcatct ctgggctcca gtctgaggat gaggctgact attactgtgc cattgggcac   300
agcagcggtt ggatattcgg aggagggacc cggctgaccg tcctc                   345
```

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261
gaggtgcagc tggtgcagtc tggagcagag gtgaaaaggc ccggggagtc tctgaagatc    60
tcctgtaaga cttctggata cagctttgcc agcagttgga tcagctgggt gcgccagatg   120
cccgggaaag gcctggagtg gatgggggcg attgatccta gtgattctgc taccagatac   180
agcccgtcct tccaaggcca ggtcactatc tcagccgaca gtccatcag taccgcctac    240 ctgcagtgga gcagcctgaa ggcctcggac actgccacgt attactgtgt gaaaggaagt   300
gagacctggg gccagggagt cctggtcacc gtctcctca                          339

<210> SEQ ID NO 262
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Glu Val Gln Leu Val Gln Ser Gly Ala Glu Val Lys Arg Pro Gly Glu
1               5                   10                  15

Ser Leu Lys Ile Ser Cys Lys Thr Ser Gly Tyr Ser Phe Ala Ser Ser
            20                  25                  30

Trp Ile Ser Trp Val Arg Gln Met Pro Gly Lys Gly Leu Glu Trp Met
        35                  40                  45

Gly Ala Ile Asp Pro Ser Asp Ser Ala Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 263
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gly Tyr Ser Phe Ala Ser Ser Trp Ile Ser
1               5                   10

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ile Asp Pro Ser Asp Ser Ala Thr Arg
1               5

<210> SEQ ID NO 265

<400> SEQUENCE: 265

000

<210> SEQ ID NO 266
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 266

```
cagcctgtgc tgactcagcc ggcctccctc tcagcttctc ctggagcatc agccagtctc      60
acatgtacct tcagcggtgg catcaatgtt gctggctaca acatactctg gtaccagcag     120
aaggcaggga gtcctccccg gtatcttctg aggtacaaat cagactcaac taaggaccag     180
ggctctggag tccccagccg cttctctgga tccaaagatg cttcagcgaa cacaggaatt     240
ttacgcatct ctgggctcca gtctgaggat gaggctgact attactgtgc cattgggcac     300
agcagcggtt ggatattcgg aggagggacc cgcctgaccg tccta                     345
```

<210> SEQ ID NO 267
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Gln Pro Val Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
                20                  25                  30

Tyr Asn Ile Leu Trp Tyr Gln Gln Lys Ala Gly Ser Pro Pro Arg Tyr
            35                  40                  45

Leu Leu Arg Tyr Lys Ser Asp Ser Thr Lys Asp Gln Gly Ser Gly Val
        50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Ile Phe Gly Gly Gly Thr Arg Leu
            100                 105                 110

Ile Val Leu
        115

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 271

```
gaggtgcagc tggtgcagtc tggagcagag gtgaaaaggc ccggggagtc tctgaagatc      60
tcctgtcaga cttctggata caggtttacc agcagctgga tcagctgggt gcgccagatg     120
cccgggaaag gcctggagtg gatgggggca attgatccta gtgattctga gaccagatac     180
agcccgtcct tccaaggcca ggtcaccatc tcagccgaca gtccatcag caccgcctac      240 ctgaagtgga gcagcctgaa ggcctcggac actgccacgt attactgtgt gaaaggaagt     300
gagacctggg gccagggagt cctggtcacc gtctcctca                            339
```

<210> SEQ ID NO 272
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Glu Val Gln Leu Val Gln Ser Gly Ala Glu Val Lys Arg Pro Gly Glu
1               5                   10                  15

Ser Leu Lys Ile Ser Cys Gln Thr Ser Gly Tyr Arg Phe Thr Ser Ser
            20                  25                  30

Trp Ile Ser Trp Val Arg Gln Met Pro Gly Lys Gly Leu Glu Trp Met
        35                  40                  45

Gly Ala Ile Asp Pro Ser Asp Ser Glu Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 273
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gly Tyr Arg Phe Thr Ser Ser Trp Ile Ser
1               5                   10

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 274

Ile Asp Pro Ser Asp Ser Glu Thr Arg
1               5

<210> SEQ ID NO 275

<400> SEQUENCE: 275

000

<210> SEQ ID NO 276
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 276
caggctgccc tgactcagcc ggcctccctc tcagcatctc ctggagcatc agccagtctc      60
acatgcacct tcagcggtgg catcaatgtt gctggctacc acatattgtg gtatcagcag     120
aagccaggga gtcctccccg gtatcttctg aggtataaat cagactcaga gaaggaccag     180
ggctctggag tccccagccg cttctctgga tccaaagatg cttcggccaa cagagggatt     240
ttacgcatct ctgggctcca gtctgaagat gaggctgact attactgtgc cattgggcac     300
agtagtagcg gttgggtatt cggaggaggg acccggctca ccgtcctc                  348

<210> SEQ ID NO 277
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 277

Gln Ala Ala Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr His Ile Leu Trp Tyr Gln Gln Lys Pro Gly Ser Pro Pro Arg Tyr
        35                  40                  45

Leu Leu Arg Tyr Lys Ser Asp Ser Glu Lys Asp Gln Gly Ser Gly Val
    50                  55                  60

Pro Ser Arg Phe Ser Gly Ser Lys Asp Ala Ser Ala Asn Arg Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Ser Gly Trp Val Phe Gly Gly Gly Thr Arg
            100                 105                 110

Leu Thr Val Leu
        115

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 281

```
gaggtgcagc tggtgcagtc tggagcagag gtgaaaaggc ccggggagtc tctgaagatc      60
tcctgtcaga cttctggaaa cagctttacc aacaactgga tcagctgggt gcgccagatg     120
cccggaaaag gcctggagtg gatgggggcg attgatccta gtgattctga aaccagatac     180
agcccgtcct tccaaggcca ggtcaccatc tcagccgaca gtccatcaa caccgcctac      240 ctgcagtgga gcagcctgaa ggcctcggac accgccacgt attactgtgt gaaaggaagt     300
gagacctggg gccagggagt cctggtcacc gtctcctca                            339
```

<210> SEQ ID NO 282
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 282

```
Glu Val Gln Leu Val Gln Ser Gly Ala Glu Val Lys Arg Pro Gly Glu
1               5                   10                  15

Ser Leu Lys Ile Ser Cys Gln Thr Ser Gly Asn Ser Phe Thr Asn Asn
            20                  25                  30

Trp Ile Ser Trp Val Arg Gln Met Pro Gly Lys Gly Leu Glu Trp Met
        35                  40                  45

Gly Ala Ile Asp Pro Ser Asp Ser Glu Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser
```

<210> SEQ ID NO 283
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Gly Asn Ser Phe Thr Asn Asn Trp Ile Ser
1               5                   10

<210> SEQ ID NO 284

<400> SEQUENCE: 284

000

<210> SEQ ID NO 285

<400> SEQUENCE: 285

000

<210> SEQ ID NO 286
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 286
cagcctgtgc tgactcagcc ggcctccctc tcagcatctc ctggagcatc agccagtctc     60
acatgtacct tcagcggtgg catcaatgtt gctggctaca acatactctg gtaccagcag    120
aaggcaggga gtcctccccg gtatcttctg aggtacaaat cagactcaac taaggaccag    180
ggctctggag tccccagccg cttctctgga tccaaagatg cttcagcgaa cacaggaatt    240
ttacgcatct ctgggctcca gtctgaggat gaggctgact attactgtgc cattgggcac    300
agcagcggtt ggatattcgg aggagggacc cggctgaccg tcctc                    345

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

```
<210> SEQ ID NO 291
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 291
caggtgcagc tggtgcaatc tggagcagag gtgaaaaggc ccggggaatc tctgacgatc      60
tcctgtaaga cttctggata cagctttacc gacagctggg tcgcctgggt gcgccagatg     120
cccgggaaag gctggagtg gttggggagc atctatcctg gtgattctga tgccagatac      180
aacccgtcct tccaaggcca cgtcactatc tcggccgaca cgtccgtcac caccacctac     240
ctgaagtgga gcagcctgaa ggcctcggac actgccacgt attactgtgt gaaaggaagt     300
gagacctggg gccagggagt cctggtcacc gtctcctca                            339

<210> SEQ ID NO 292
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gln Val Gln Leu Val Gln Ser Gly Ala Glu Val Lys Arg Pro Gly Glu
 1               5                  10                  15

Ser Leu Thr Ile Ser Cys Lys Thr Ser Gly Tyr Ser Phe Thr Asp Ser
             20                  25                  30

Trp Val Ala Trp Val Arg Gln Met Pro Gly Lys Gly Leu Glu Trp Leu
         35                  40                  45

Gly Ser Ile Tyr Pro Gly Asp Ser Asp Ala Arg Tyr Asn Pro Ser Phe
     50                  55                  60

Gln Gly His Val Thr Ile Ser Ala Asp Thr Ser Val Thr Thr Thr Tyr
 65                  70                  75                  80

Leu Lys Trp Ser Ser Leu Lys Ala Ser Asp Thr Ala Thr Tyr Tyr Cys
                 85                  90                  95

Val Lys Gly Ser Glu Thr Trp Gly Gln Gly Val Leu Val Thr Val Ser
            100                 105                 110

Ser

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296
```

```
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 296
aagcctatgc tgactcagcc agcctccctc tcagcatctc ctggagcatc agccagtctc    60
acatgtacct tcagcggtgg catcaatgtt gctggctaca acatactctg gtaccagcag   120
aaggcaggga gtcctccccg gtatcttctg aggtacaaat cagactcaac taaggaccag   180
ggctctggag tccccagccg cttctctgga tccaaagatg cttcagcgaa cacaggaatt   240
ttacgcatct ctgggctcca gtctgaggat gaggctgact attactgtgc cattgggcac   300
agcagcggtt ggatattcgg aggagggacc cggctgaccg tcctc                   345

<210> SEQ ID NO 297
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Lys Pro Met Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Asn Ile Leu Trp Tyr Gln Gln Lys Ala Gly Ser Pro Pro Arg Tyr
        35                  40                  45

Leu Leu Arg Tyr Lys Ser Asp Ser Thr Lys Asp Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Ile Phe Gly Gly Gly Thr Arg Leu
            100                 105                 110

Thr Val Leu
        115

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301
```

```
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 301
caggtgcagc tggtgcagtc tggagcagag gtgaaaaggc ccggggaatc tctgaggatc      60
tcctgtaaga cttctggata cagctttacc gacagctggg tcgcctgggt gcgccagatg     120
cccgggaaag ggctggagtg gttggggagc atctatcctg gtgattctga taccagatac     180
agcccgtcct ccaaggcca ggtcaccatc tcagccgaca gtccatcac caccgcctac      240 ctgaagtgga gcagcctgaa ggcctcggac actgccacgt attactgtgt gaaaggaagt     300
gagacctggg gccagggagt cctggtcacc gtctcctca                            339

<210> SEQ ID NO 302
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Gln Val Gln Leu Val Gln Ser Gly Ala Glu Val Lys Arg Pro Gly Glu
1               5                   10                  15

Ser Leu Arg Ile Ser Cys Lys Thr Ser Gly Tyr Ser Phe Thr Asp Ser
            20                  25                  30

Trp Val Ala Trp Val Arg Gln Met Pro Gly Lys Gly Leu Glu Trp Leu
        35                  40                  45

Gly Ser Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306
<211> LENGTH: 345
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 306

```
cagcctgtgc tgactcagcc ggcctccctc tcagcatctc ctggagcatc agccagtctc    60
acatgcacct tcaacggtgg catcactgtt cctggctacg atatactctg gtaccagcag   120
aagtcaggga gtcctccccg gtatcttctg aggtacaaat cagactcaac taaggaccag   180
ggctctggag tccccagccg cttctctgga tccaaagatg cttcaacgaa cacagggatt   240
ttacgcatct ctgggctcca gtctgaggat gaggctgact attactgtgc cattgggcac   300
agcagcggtt ggatattcgg aggagggacc cggctgaccg tcctc                   345
```

<210> SEQ ID NO 307
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 307

```
Gln Pro Val Leu Thr Gln Pro Ala Ser Leu Ser Ala Ser Pro Gly Ala
1               5                  10                  15

Ser Ala Ser Leu Thr Cys Thr Phe Asn Gly Gly Ile Thr Val Pro Gly
            20                  25                  30

Tyr Asp Ile Leu Trp Tyr Gln Gln Lys Ser Gly Ser Pro Pro Arg Tyr
        35                  40                  45

Leu Leu Arg Tyr Lys Ser Asp Ser Thr Lys Asp Gln Gly Ser Gly Val
    50                  55                  60

Pro Ser Arg Phe Ser Gly Ser Lys Asp Ala Ser Thr Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Ile Phe Gly Gly Thr Arg Leu
            100                 105                 110

Thr Val Leu
        115
```

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

```
Gly Gly Ile Thr Val Pro Gly Tyr Asp
1               5
```

<210> SEQ ID NO 309

<400> SEQUENCE: 309

000

<210> SEQ ID NO 310

<400> SEQUENCE: 310

000

<210> SEQ ID NO 311
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 311
caggtgcagc tggtgcagtc tggggcagag gtgaaaaggc ccggggagtc tctgaagatc      60
tcctgtaaga cttctagata cagctttacc agcagctgga tcggctgggt gcgccagatg     120
cccgggaaag gctggagtg gttggggagc atctatcctg gtgattctga taccagatac      180
aacccgtcct tccaaggcca cgtcactatc tcagccgaca gtccgtcac caccacctac      240 ctgaagtgga gcagcctgaa ggcctcggac actgccacgt attactgtgt gaaaggaagt      300
gagacctggg gccagggagt cctggtcacc gtctcctca                            339

<210> SEQ ID NO 312
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Gln Val Gln Leu Val Gln Ser Gly Ala Glu Val Lys Arg Pro Gly Glu
1               5                   10                  15

Ser Leu Lys Ile Ser Cys Lys Thr Ser Arg Tyr Ser Phe Thr Ser Ser
            20                  25                  30

Trp Ile Gly Trp Val Arg Gln Met Pro Gly Lys Gly Leu Glu Trp Leu
        35                  40                  45

Gly Ser Ile Tyr Pro Gly Asp Ser Asp Thr Arg Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 313
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Arg Tyr Ser Phe Thr Ser Ser Trp Ile Gly
1               5                   10

<210> SEQ ID NO 314

<400> SEQUENCE: 314

<210> SEQ ID NO 315

<400> SEQUENCE: 315

000

<210> SEQ ID NO 316
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 316
cagcctgtgc tgactcagcc agcctccctc tcagcatctc ctggagcatc agccagtctc    60
acatgtacct tcagcggtgg catcaatgtt gctggctaca acatactctg gtaccagcag   120
aaggcaggga gtcctccccg gtatcttctg aggtacaaat cagactcaac taaggaccag   180
ggctctggag tccccagccg cttctctgga tccaaagatg cttcagcgaa cacaggaatt   240
ttacgcatct ctgggctcca gtctgaggat gaggctgact attactgtgc cattgggcac   300
agcagcggtt ggatattcgg aggagggacc cggctgaccg tcctc                   345

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 321
gaggtgcagt tggtggagtc tggagcagag gtgaaaaggc ccggggaatc tctgacgatc    60
tcctgtaaga cttctggata cagctttacc gacagctggg tcagctgggt gcgccagatg   120
cccgggaaag gcctggagtg gatggggagc atctatcctg gtgattctga acgaaatac    180 aacccgtcct tccaaggcca cgtcactatc tcagccgaca gtccgtcac caccacctac   240 ctgaagtgga gcagcctgaa ggcctcggac actgccacgt attactgtgt gaaaggaagt      300
gagacctggg gccagggagt cctggtcacc gtctcctca      339

<210> SEQ ID NO 322
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Glu Val Gln Leu Val Glu Ser Gly Ala Glu Val Lys Arg Pro Gly Glu
1               5                   10                  15

Ser Leu Thr Ile Ser Cys Lys Thr Ser Gly Tyr Ser Phe Thr Asp Ser
            20                  25                  30

Trp Val Ser Trp Val Arg Gln Met Pro Gly Lys Gly Leu Glu Trp Met
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 323
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Gly Tyr Ser Phe Thr Asp Ser Trp Val Ser
1               5                   10

<210> SEQ ID NO 324

<400> SEQUENCE: 324

000

<210> SEQ ID NO 325

<400> SEQUENCE: 325

000

<210> SEQ ID NO 326
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 326
cagcctgtgc tgactcagcc ggcctccctc tcagcatctc ctggagcatc agccagtctc      60

```
acatgcacct tcagcggtgg catcaatgtt gctggctact acatacactg gtaccagcag    120
aagccaggga gtcctccccg gtaccttctg aggtacaaat cagactcaga taagcaccag    180
ggctctggag tccccagccg cttctctgga tccaaagatg cttcggccaa cacagggatt    240
ttacgcatct ctgggctcca gtctgaggat gaggctgact attactgtgc cattgggcac    300
agcagcggtt gggtattcgg aggagggacc cggctgaccg tcctc                    345
```

<210> SEQ ID NO 327
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

```
Gln Pro Val Leu Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Tyr Ile His Trp Tyr Gln Gln Lys Pro Gly Ser Pro Pro Arg Tyr
        35                  40                  45

Leu Leu Arg Tyr Lys Ser Asp Ser Asp Lys His Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Val Phe Gly Gly Gly Thr Arg Leu
            100                 105                 110

Thr Val Leu
        115
```

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 331

```
gaggtgcagc tggtgcagtc tggagcagag gtgaaaaggc ccggggaatc tctgacgatc    60
```

```
tcctgtaaga cttctggata cagctttacc agctactgga tcacctgggt gcgccagatg    120
cccgggaaag ggctggagtg gttggggagc atctatcctg gtgattctga aacgaaatac    180
aacccgtcct tccaaggcca cgtcactatc tcagccgaca agtccgtcac caccacctac    240
ctgaagtgga gcagcctgaa ggcctcggac actgccacgt attactgtgt gaaaggaagt    300
gagacctggg gccagggagt cctggtcacc gtctcctca                           339
```

<210> SEQ ID NO 332
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 332

```
Glu Val Gln Leu Val Gln Ser Gly Ala Glu Val Lys Arg Pro Gly Glu
1               5                   10                  15

Ser Leu Thr Ile Ser Cys Lys Thr Ser Gly Tyr Ser Phe Thr Ser Tyr
            20                  25                  30

Trp Ile Thr Trp Val Arg Gln Met Pro Gly Lys Gly Leu Glu Trp Leu
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser
```

<210> SEQ ID NO 333
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 333

```
Gly Tyr Ser Phe Thr Ser Tyr Trp Ile Thr
1               5                   10
```

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 341

```
gaggtgcagc tggtgcagtc tggagcagag gtgaaaaggc ccggggaatc tctgacgatc      60
tcctgtaaga cttctggata cagctttacc gacaactgga tcagctgggt cgcgcagatg     120
cccggaaaag gcctggagtg gatgggagc atctatcctg gtgattctga acgaaatac       180 aacccgtcct tccaaggcca cgtcactatc tcagccgaca gtccgtcac caccacctac      240 ctgaagtgga gcagcctgaa ggcctcggac actgccacgt attactgtgt gaaaggaagt     300
gagacctggg gccagggagt cctggtcacc gtctcctca                             339
```

<210> SEQ ID NO 342
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 342

```
Glu Val Gln Leu Val Gln Ser Gly Ala Glu Val Lys Arg Pro Gly Glu
1               5                   10                  15

Ser Leu Thr Ile Ser Cys Lys Thr Ser Gly Tyr Ser Phe Thr Asp Asn
            20                  25                  30

Trp Ile Ser Trp Val Arg Gln Met Pro Gly Lys Gly Leu Glu Trp Met
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Ser Leu Lys Ala Ser Asp Thr Ala Thr Tyr Tyr Cys
```

```
                    85                  90                  95
Val Lys Gly Ser Glu Thr Trp Gly Gln Gly Val Leu Val Thr Val Ser
            100                 105                 110
Ser
```

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

```
Gly Tyr Ser Phe Thr Asp Asn Trp Ile Ser
1               5                   10
```

<210> SEQ ID NO 344

<400> SEQUENCE: 344

000

<210> SEQ ID NO 345

<400> SEQUENCE: 345

000

<210> SEQ ID NO 346
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 346

```
cagtctgtgc tgacgcagcc agcctccctc tcagcatctc ctggagcatc agccagtctc    60
acatgtacct tcagcggtgg catcaatgtt gctggctaca acatactctg gtaccaacag   120
aaggcaggga gtcctccccg gtatcttctg aggtacaaat cagactcaac taaggaccag   180
ggctctggag tccccagccg cttctctgga tccaaagatg cttcagcgaa tacaggaatt   240
ttacgcatct ctgggctcca gtctgaggat gaggctgact attactgtgc cattgggcac   300
agcagcggtt ggatattcgg aggagggacc cggctgaccg tcctc                   345
```

<210> SEQ ID NO 347
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

```
Gln Ser Val Leu Thr Gln Pro Ala Ser Leu Ser Ala Ser Pro Gly Ala
1               5                   10                  15
Ser Ala Ser Leu Thr Cys Thr Phe Ser Gly Gly Ile Asn Val Ala Gly
                20                  25                  30
Tyr Asn Ile Leu Trp Tyr Gln Gln Lys Ala Gly Ser Pro Pro Arg Tyr
            35                  40                  45
Leu Leu Arg Tyr Lys Ser Asp Ser Thr Lys Asp Gln Gly Ser Gly Val
```

```
                    50                  55                  60
Pro Ser Arg Phe Ser Gly Ser Lys Asp Ala Ser Ala Asn Thr Gly Ile
 65                  70                  75                  80

Leu Arg Ile Ser Gly Leu Gln Ser Glu Asp Glu Ala Asp Tyr Tyr Cys
                 85                  90                  95

Ala Ile Gly His Ser Ser Gly Trp Ile Phe Gly Gly Gly Thr Arg Leu
            100                 105                 110

Thr Val Leu
        115

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 351
caggtgcagc tggtgcaatc tggagcagag gtgaaaaggc ccggggagtc tctgaagatc      60
tcctgtaaga cttctggata caggtttacc agcagctgga tcagctgggt gcgccagatg     120
cccgggaaag ggctggagtg gttggggagc atctatcctg gtgattctga aacgaaatac     180
aacccgtcct tccaaggcca cgtcactatc tcagccgaca gtccgtcac caccacctac      240 ctgaagtgga gcagcctgaa ggcctcggac actgccacgt attactgtgt gaaaggaagt     300
gagacctggg gccagggagt cctggtcacc gtctcctca                            339

<210> SEQ ID NO 352
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Gln Val Gln Leu Val Gln Ser Gly Ala Glu Val Lys Arg Pro Gly Glu
 1               5                  10                  15

Ser Leu Lys Ile Ser Cys Lys Thr Ser Gly Tyr Arg Phe Thr Ser Ser
                20                  25                  30

Trp Ile Ser Trp Val Arg Gln Met Pro Gly Lys Gly Leu Glu Trp Leu
            35                  40                  45

Gly Ser Ile Tyr Pro Gly Asp Ser Glu Thr Lys Tyr Asn Pro Ser Phe
```

| | | | | | | | 50 | | | | | 55 | | | | | 60 | | |
|---|---|---|---|---|---|---|---|---|---|---|---|---|---|---|---|---|---|---|---|

Gln Gly His Val Thr Ile Ser Ala Asp Lys Ser Val Thr Thr Thr Tyr
65      70      75      80

Leu Lys Trp Ser Ser Leu Lys Ala Ser Asp Thr Ala Thr Tyr Tyr Cys
     85      90      95

Val Lys Gly Ser Glu Thr Trp Gly Gln Gly Val Leu Val Thr Val Ser
    100      105      110

Ser

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356
<211> LENGTH: 345
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 356

```
tcctctgagc tgactcagcc agcctccctc tcagcatctc ctggagcatc agccagtctc      60
acatgtacct tcagcggtgg catcaatgtt gctggctaca acatactctg gtaccaacag     120
aaggcaggga gtcctccccg gtatcttctg aggtacaaat cagactcaac taaggaccag     180
ggctctggag tccccagccg cttctctgga tccaaagatg cttcagcgaa tacaggaatt     240
ttacgcatct ctgggctcca gtctgaggat gaggctgact attactgtgc cattgggcac     300
agcagcggtt ggatattcgg aggagggacc cggctgaccg tcctc                     345
```

<210> SEQ ID NO 357
<211> LENGTH: 115
<212> TYPE: PRT
<213> ORGANISM: Artificial Sequence
<220> FEATURE:
<223> OTHER INFORMATION: Description of Artificial Sequence: Synthetic
   polypeptide

<400> SEQUENCE: 357

Ser Ser Glu Leu Thr Gln Pro Ala Ser Leu Ser Ala Ser Pro Gly Ala
1      5      10      15

Ser Ala Ser Leu Thr Cys Thr Phe Ser Gly Gly Ile Asn Val Ala Gly
     20      25      30

Tyr Asn Ile Leu Trp Tyr Gln Gln Lys Ala Gly Ser Pro Pro Arg Tyr
    35      40      45

Leu Leu Arg Tyr Lys Ser Asp Ser Thr Lys Asp Gln Gly Ser Gly Val
  50      55      60

```
Pro Ser Arg Phe Ser Gly Ser Lys Asp Ala Ser Ala Asn Thr Gly Ile
 65                  70                  75                  80

Leu Arg Ile Ser Gly Leu Gln Ser Glu Asp Glu Ala Asp Tyr Tyr Cys
                 85                  90                  95

Ala Ile Gly His Ser Ser Gly Trp Ile Phe Gly Gly Gly Thr Arg Leu
            100                 105                 110

Thr Val Leu
        115

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 361
caggtgcagc tggtgcagtc tggagcagag gtgaaaaggc ccggggaatc tctgacgatc      60
tcctgtaaga cttctggata cagctttacc gacagctgga tcggctgggt gcgccagatg     120
cccgggaaag gcctggagtg gatggcgagc atctatcctg atgattctga acgaaatac     180 aacccgtcct tccaaggcca cgtcactatc tcagccgaca gtccgtcac caccacctac     240 ctgaagtgga gcagcctgaa ggcctcggac actgccacgt attactgtgt gaaaggaagt     300
gagacctggg gccagggagt cctggtcacc gtctcctca                            339

<210> SEQ ID NO 362
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

Gln Val Gln Leu Val Gln Ser Gly Ala Glu Val Lys Arg Pro Gly Glu
 1               5                  10                  15

Ser Leu Thr Ile Ser Cys Lys Thr Ser Gly Tyr Ser Phe Thr Asp Ser
                 20                  25                  30

Trp Ile Gly Trp Val Arg Gln Met Pro Gly Lys Gly Leu Glu Trp Met
             35                  40                  45

Ala Ser Ile Tyr Pro Asp Asp Ser Glu Thr Lys Tyr Asn Pro Ser Phe
         50                  55                  60
```

```
Gln Gly His Val Thr Ile Ser Ala Asp Lys Ser Val Thr Thr Thr Tyr
 65                  70                  75                  80
Leu Lys Trp Ser Ser Leu Lys Ala Ser Asp Thr Ala Thr Tyr Tyr Cys
                 85                  90                  95
Val Lys Gly Ser Glu Thr Trp Gly Gln Gly Val Leu Val Thr Val Ser
            100                 105                 110
Ser
```

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 366

```
cagcctgtgc tgactcagcc agcctccctc tcagcatctc ctggagcatc agccagtctc      60
acatgtacct tcagcggtgg catcaatgtt gctggctaca acatactctg gtaccagcag     120
aaggcaggga gtcctccccg gtatcttctg aggtacaaat cagactcaac taaggaccag     180
ggctctggag tccccagccg cttctctgga tccaaagatg cttcagcgaa tacaggaatt     240
ttacgcatct ctgggctcca gtctgaggat gaggctgact attactgtgc cattgggcac     300
agcagcggtt ggatattcgg aggagggacc cggctgaccg tcctc                     345
```

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

```
<400> SEQUENCE: 370

000

<210> SEQ ID NO 371
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 371
gaggtgcagc tggtgcaatc tggagcagag gtgaaaaggc ccggggaatc tctgaggatc     60
tcctgtaaga cttctggata cagctttacc gacagctgga tcagctgggt gcgccagatg    120
cccgggaaag ggctggagtg gttggggagc atctatcctg gtgattctga aacgaaatac    180
aacccgtcct tccaaggcca cgtcactatc tcagccgaca gtccgtcac caccacctac     240 ctgaagtgga gcagcctgaa ggcctcggac actgccacgt attactgtgt gaaaggaagt    300
gagacctggg gccagggagt cctggtcacc gtctcctca                           339

<210> SEQ ID NO 372
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

Glu Val Gln Leu Val Gln Ser Gly Ala Glu Val Lys Arg Pro Gly Glu
1               5                   10                  15

Ser Leu Arg Ile Ser Cys Lys Thr Ser Gly Tyr Ser Phe Thr Asp Ser
            20                  25                  30

Trp Ile Ser Trp Val Arg Gln Met Pro Gly Lys Gly Leu Glu Trp Leu
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 373

<400> SEQUENCE: 373

000

<210> SEQ ID NO 374

<400> SEQUENCE: 374

000

<210> SEQ ID NO 375
```

<400> SEQUENCE: 375

000

<210> SEQ ID NO 376
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 376

```
cagcctgtgc tgactcagcc ggcctccctc tcagcatctc ctggagcatc agccagtctc      60
acatgcacct tcagcggtgg catcaatgtt gctggctaca acatactctg gtaccagcag     120
aaggcaggga gtcctccccg gtatcttctg aggtacaaat cagactcaac taaggaccag     180
ggctctggag tccccagccg cttctctgga tccaaagatg cttcagcgaa cacaggaatt     240
ttacgcatct ctgggctcca gtctgaggat gaggctgact attactgtgc cattgggcac     300
agcagcggtt ggatattcgg aggagggacc cggctgaccg tcctc                     345
```

<210> SEQ ID NO 377
<400> SEQUENCE: 377

000

<210> SEQ ID NO 378
<400> SEQUENCE: 378

000

<210> SEQ ID NO 379
<400> SEQUENCE: 379

000

<210> SEQ ID NO 380
<400> SEQUENCE: 380

000

<210> SEQ ID NO 381
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 381

```
gaggtgcagc tggtgcagtc tggagcagag gtgaaaaggc ccggggaatc tctgacgatc      60
tcctgtaaga cctctggata cagttttacc gacagttgga tcagctgggt gcgccagatg     120
cccgggaaag gcctggagtg gatgggagc atctatcctg gtgattctga acgaaatac      180 aacccgtcct tccaaggcca cgtcactatc tcagccgaca gtccgtcac caccacctac     240 ctgaagtgga gcagcctgaa ggcctcggac actgccacgt attactgtgt gaaaggaagt     300
gagacctggg gccagggagt cctggtcacc gtctcctca                           339
```

<210> SEQ ID NO 382
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 382

Glu Val Gln Leu Val Gln Ser Gly Ala Glu Val Lys Arg Pro Gly Glu
1               5                   10                  15

Ser Leu Thr Ile Ser Cys Lys Thr Ser Gly Tyr Ser Phe Thr Asp Ser
            20                  25                  30

Trp Ile Ser Trp Val Arg Gln Met Pro Gly Lys Gly Leu Glu Trp Met
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386
<211> LENGTH: 345
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 386
cagcctatgc tgactcagcc agcctccctc tcagcatctc ctggagcatc agccagtctc     60
acatgtacct tcagcggtgg catcaatgtt gctggctaca catactctg gtaccagcag    120 aaggcaggga gtcctccccg gtatcttctg aggtacaaat cagactcaac taaggaccag    180
ggctctggag tccccagccg cttctctgga tccaaagatg cttcagcgaa cacaggaatt    240
ttacgcatct ctgggctcca gtctgaggat gaggctgact attactgtgc cattgggcac    300
agcagcggtt ggatattcgg aggagggacc cggctgaccg tcctt                     345

<210> SEQ ID NO 387

<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 387

```
Gln Pro Met Leu Thr Gln Pro Ala Ser Leu Ser Ala Ser Pro Gly Ala
1               5                   10                  15
Ser Ala Ser Leu Thr Cys Thr Phe Ser Gly Gly Ile Asn Val Ala Gly
            20                  25                  30
Tyr Asn Ile Leu Trp Tyr Gln Gln Lys Ala Gly Ser Pro Pro Arg Tyr
        35                  40                  45
Leu Leu Arg Tyr Lys Ser Asp Ser Thr Lys Asp Gln Gly Ser Gly Val
    50                  55                  60
Pro Ser Arg Phe Ser Gly Ser Lys Asp Ala Ser Ala Asn Thr Gly Ile
65                  70                  75                  80
Leu Arg Ile Ser Gly Leu Gln Ser Glu Asp Glu Ala Asp Tyr Tyr Cys
                85                  90                  95
Ala Ile Gly His Ser Ser Gly Trp Ile Phe Gly Gly Gly Thr Arg Leu
            100                 105                 110
Thr Val Leu
        115
```

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 391

```
gaggtgcagc tggtgcagtc tggagcagag gtgaaaaggc ccggggagtc tctgaagatc     60
tcctgtaaga cttctggata cagttttacc gacacctgga tcagttgggt gcgccagatg    120
cccgggaaag gcctggagtg gatggggagc atctatcctg gtgattctga acgaaatac     180
aacccgtcct ccaaggcca cgtcactatc tcagccgaca agtccgtcac caccacctac    240
ctgaagtgga gcagcctgaa ggcctcggac actgccacgt attactgtgt gaaaggaagt    300
gagacctggg gccagggagt cctggtcacc gtctcctca                           339
```

<210> SEQ ID NO 392

```
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 392
```

Glu Val Gln Leu Val Gln Ser Gly Ala Glu Val Lys Arg Pro Gly Glu
1               5                   10                  15

Ser Leu Lys Ile Ser Cys Lys Thr Ser Gly Tyr Ser Phe Thr Asp Thr
            20                  25                  30

Trp Ile Ser Trp Val Arg Gln Met Pro Gly Lys Gly Leu Glu Trp Met
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser

```
<210> SEQ ID NO 393
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393
```

Gly Tyr Ser Phe Thr Asp Thr Trp Ile Ser
1               5                   10

```
<210> SEQ ID NO 394

<400> SEQUENCE: 394

000

<210> SEQ ID NO 395

<400> SEQUENCE: 395

000

<210> SEQ ID NO 396
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 396
gagactgtgg tgacccagcc ggcctccctc tcagcatctc tggagcatca gccagtctc     60 acatgtacct tcagcggtgg catcaatgtt gctggctaca catactctg gtaccagcag    120 aaggcaggga gtcctcccccg gtatcttctg aggtacaaat cagactcaac taaggaccag   180
ggctctggag tccccagccg cttctctgga tccaaagatg cttcggccaa cacagggatt   240
```

```
ttacgcatct ctgggctcca gtctgaggat gaggctgact attactgtgc cattgggcac    300
agcagcggtg tgttattcgg aggagggacc cggctgaccg tcctc                   345
```

<210> SEQ ID NO 397
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

```
Glu Thr Val Val Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Asn Ile Leu Trp Tyr Gln Gln Lys Ala Gly Ser Pro Pro Arg Tyr
        35                  40                  45

Leu Leu Arg Tyr Lys Ser Asp Ser Thr Lys Asp Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Val Leu Phe Gly Gly Gly Thr Arg Leu
            100                 105                 110

Thr Val Leu
        115
```

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 401

```
gaggtgcagc tggtggagtc tggagcagag gtgaaaaggc ccggggaatc tctgacgatc    60
tcctgtaaga cttctggata cagctttacc gacagctggg tcgcctgggt gcgccagatg   120
cccgggaaag gcctggagtg gatggggagc atctatcctg gtgattctga aacgaaatac   180
aacccgtcct tccaaggcca cgtcactatc tcagccgaca gtccgtcac caccacctac   240
```

```
ctgaagtgga gcagcctgaa ggcctcggac actgccacgt attactgtgt gaaaggaagt    300
gagacctggg gccagggagt cctggtcacc gtctcctca                           339
```

<210> SEQ ID NO 402
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

```
Glu Val Gln Leu Val Glu Ser Gly Ala Glu Val Lys Arg Pro Gly Glu
1               5                   10                  15

Ser Leu Thr Ile Ser Cys Lys Thr Ser Gly Tyr Ser Phe Thr Asp Ser
            20                  25                  30

Trp Val Ala Trp Val Arg Gln Met Pro Gly Lys Gly Leu Glu Trp Met
        35                  40                  45

Gly Ser Ile Tyr Pro Gly Asp Ser Glu Thr Lys Tyr Asn Pro Ser Phe
    50                  55                  60

Gln Gly His Val Thr Ile Ser Ala Asp Lys Ser Val Thr Thr Thr Tyr
65                  70                  75                  80

Leu Lys Trp Ser Ser Leu Lys Ala Ser Asp Thr Ala Thr Tyr Tyr Cys
                85                  90                  95

Val Lys Gly Ser Glu Thr Trp Gly Gln Gly Val Leu Val Thr Val Ser
            100                 105                 110

Ser
```

<210> SEQ ID NO 403

<400> SEQUENCE: 403

000

<210> SEQ ID NO 404
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

```
Ile Tyr Pro Gly Asp Ser Glu Thr Arg
1               5
```

<210> SEQ ID NO 405

<400> SEQUENCE: 405

000

<210> SEQ ID NO 406
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 406

```
cagactgtgg tgactcagcc agcctccctc tcagcatctc ctggagcatc agccagtctc    60
```

```
acatgtacct tcagcggtgg catcaatgtt gctggctaca acatactctg gtaccaacag    120
aaggcaggga gtcctccccg gtatcttctg aggtacaaat cagactcaac taaggaccag    180
ggctctggag tccccagccg cttctctgga tccaaagatg cttcagcgaa tacaggaatt    240
ttacgcatct ctgggctcca gtctgaggat gaggctgact attactgtgc cattgggcac    300
agcagcggtt ggatattcgg aggagggacc cggctgaccg tcctc                   345
```

<210> SEQ ID NO 407
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

```
Gln Thr Val Val Thr Gln Pro Ala Ser Leu Ser Ala Ser Pro Gly Ala
1               5                   10                  15

Ser Ala Ser Leu Thr Cys Thr Phe Ser Gly Gly Ile Asn Val Ala Gly
            20                  25                  30

Tyr Asn Ile Leu Trp Tyr Gln Gln Lys Ala Gly Ser Pro Pro Arg Tyr
        35                  40                  45

Leu Leu Arg Tyr Lys Ser Asp Ser Thr Lys Asp Gln Gly Ser Gly Val
    50                  55                  60

Pro Ser Arg Phe Ser Gly Ser Lys Asp Ala Ser Ala Asn Thr Gly Ile
65                  70                  75                  80

Leu Arg Ile Ser Gly Leu Gln Ser Glu Asp Glu Ala Asp Tyr Tyr Cys
                85                  90                  95

Ala Ile Gly His Ser Ser Gly Trp Ile Phe Gly Gly Gly Thr Arg Leu
            100                 105                 110

Thr Val Leu
        115
```

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411

```
cggggccatg gcc                                                       13
```

<210> SEQ ID NO 412
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412
acctgtcgac cc                                                                12

<210> SEQ ID NO 413
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 413
gtggctccgg aggtggcgga tcg                                                    23

<210> SEQ ID NO 414
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 414
cgcctgcggc cgc                                                               13

<210> SEQ ID NO 415
<211> LENGTH: 18
<212> TYPE: PRT
<213> ORGANISM: Zaire ebolavirus

<400> SEQUENCE: 415

Val Pro Ser Ala Thr Lys Arg Trp Gly Phe Arg Ser Gly Val Pro Pro
1               5                   10                  15

Lys Val

<210> SEQ ID NO 416
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 416

His His His His His His
1               5

<210> SEQ ID NO 417
<211> LENGTH: 151
<212> TYPE: PRT
<213> ORGANISM: Marburg marburgvirus

<400> SEQUENCE: 417

Ser Gly Thr Leu Gln Lys Thr Glu Asp Val His Leu Met Gly Phe Thr
1               5                   10                  15

Leu Ser Gly Gln Lys Val Ala Asp Ser Pro Leu Glu Ala Ser Lys Arg
            20                  25                  30

Trp Ala Phe Arg Thr Gly Val Pro Pro Lys Asn Val Glu Tyr Thr Glu
            35                  40                  45

Gly Glu Ala Lys Thr Cys Tyr Asn Ile Ser Val Thr Asp Pro Ser
 50                  55                  60

Gly Lys Ser Leu Leu Asp Pro Pro Thr Asn Ile Arg Asp Tyr Pro
65                  70                  75                  80

Lys Cys Lys Thr Ile His His Ile Gln Gly Gln Asn Pro His Ala Gln
            85                  90                  95

Gly Ile Ala Leu His Leu Trp Gly Ala Phe Phe Leu Tyr Asp Arg Ile
            100                 105                 110

Ala Ser Thr Thr Met Tyr Arg Gly Lys Val Phe Thr Glu Gly Asn Ile
            115                 120                 125

Ala Ala Met Ile Val Asn Lys Thr Val His Lys Met Ile Phe Ser Arg
            130                 135                 140

Gln Gly Gln Gly Tyr Arg His
145                 150

<210> SEQ ID NO 418
<211> LENGTH: 148
<212> TYPE: PRT
<213> ORGANISM: Sudan ebolavirus

<400> SEQUENCE: 418

Lys Asp His Leu Ala Ser Thr Asp Gln Leu Lys Ser Val Gly Leu Asn
1               5                   10                  15

Leu Glu Gly Ser Gly Val Ser Thr Asp Ile Pro Ser Ala Thr Lys Arg
            20                  25                  30

Trp Gly Phe Arg Ser Gly Val Pro Pro Lys Val Val Ser Tyr Glu Ala
            35                  40                  45

Gly Glu Trp Ala Glu Asn Cys Tyr Asn Leu Glu Ile Lys Lys Pro Asp
 50                  55                  60

Gly Ser Glu Cys Leu Pro Pro Pro Asp Gly Val Arg Gly Phe Pro
65                  70                  75                  80

Arg Cys Arg Tyr Val His Lys Ala Gln Gly Thr Gly Pro Cys Pro Gly
            85                  90                  95

Asp Tyr Ala Phe His Lys Asp Gly Ala Phe Phe Leu Tyr Asp Arg Leu
            100                 105                 110

Ala Ser Thr Val Ile Tyr Arg Gly Val Asn Phe Ala Glu Gly Val Ile
            115                 120                 125

Ala Phe Leu Ile Leu Ala Lys Pro Lys Glu Thr Phe Leu Gln Ser Pro
            130                 135                 140

Pro Ile Arg Glu
145

<210> SEQ ID NO 419
<211> LENGTH: 148
<212> TYPE: PRT
<213> ORGANISM: Zaire ebolavirus

<400> SEQUENCE: 419

Arg Asp Lys Leu Ser Ser Thr Asn Gln Leu Arg Ser Val Gly Leu Asn
1               5                   10                  15

Leu Glu Gly Asn Gly Val Ala Thr Asp Val Pro Ser Ala Thr Lys Arg
            20                  25                  30

Trp Gly Phe Arg Ser Gly Val Pro Pro Lys Val Val Asn Tyr Glu Ala
            35                  40                  45

```
Gly Glu Trp Ala Glu Asn Cys Tyr Asn Leu Glu Ile Lys Lys Pro Asp
    50                  55                  60

Gly Ser Glu Cys Leu Pro Ala Ala Pro Asp Gly Ile Arg Gly Phe Pro
65                  70                  75                  80

Arg Cys Arg Tyr Val His Lys Val Ser Gly Thr Gly Pro Cys Ala Gly
                85                  90                  95

Asp Phe Ala Phe His Lys Glu Gly Ala Phe Phe Leu Tyr Asp Arg Leu
            100                 105                 110

Ala Ser Thr Val Ile Tyr Arg Gly Thr Thr Phe Ala Glu Gly Val Val
        115                 120                 125

Ala Phe Leu Ile Leu Pro Gln Ala Lys Lys Asp Phe Phe Ser Ser His
    130                 135                 140

Pro Leu Arg Glu
145

<210> SEQ ID NO 420
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Lys Val Asn Pro Glu Ile Asp Thr Thr Gly Glu Trp Ala Phe
1               5                   10

<210> SEQ ID NO 421
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Ile Asp Thr Thr Gly Glu Trp Ala Phe Trp Glu Thr Lys Lys
1               5                   10

<210> SEQ ID NO 422
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Gly Glu Trp Ala Phe Trp Glu Thr Lys Lys Asn Leu Thr Arg Lys
1               5                   10                  15

<210> SEQ ID NO 423
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Trp Glu Thr Lys Lys Asn Leu Thr Arg Lys Ile Arg Ser Glu Glu
1               5                   10                  15
```

```
<210> SEQ ID NO 424
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Asn Leu Thr Arg Lys Ile Arg Ser Glu Glu Leu Ser Phe Thr Val
1               5                   10                  15

<210> SEQ ID NO 425
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Cys Asn Pro Asn Leu His Tyr Trp Thr Thr Gln Asp Glu Gly Ala
1               5                   10                  15

<210> SEQ ID NO 426
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

His Tyr Trp Thr Thr Gln Asp Glu Gly Ala Ala Ile Leu Gly Leu Ala
1               5                   10                  15

<210> SEQ ID NO 427
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Gln Asp Glu Gly Ala Ala Ile Leu Gly Leu Ala Trp Ile Pro Tyr Phe
1               5                   10                  15

<210> SEQ ID NO 428
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Ala Ile Leu Gly Leu Ala Trp Ile Pro Tyr Phe Gly Pro Ala Ala Glu
1               5                   10                  15

<210> SEQ ID NO 429
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429
```

```
Trp Ile Pro Tyr Phe Gly Pro Ala Ala Glu Gly Ile Tyr Thr Glu
1               5                   10                  15

<210> SEQ ID NO 430
<211> LENGTH: 17
<212> TYPE: PRT
<213> ORGANISM: Zaire ebolavirus

<400> SEQUENCE: 430

Glu Ile Asp Thr Thr Ile Gly Glu Trp Ala Phe Trp Glu Thr Lys Lys
1               5                   10                  15

Asn

<210> SEQ ID NO 431
<211> LENGTH: 17
<212> TYPE: PRT
<213> ORGANISM: Sudan ebolavirus

<400> SEQUENCE: 431

Asn Ile Asn Ala Asp Ile Gly Glu Trp Ala Phe Trp Glu Asn Lys Lys
1               5                   10                  15

Asn

<210> SEQ ID NO 432
<211> LENGTH: 17
<212> TYPE: PRT
<213> ORGANISM: Bundibugyo virus

<400> SEQUENCE: 432

Thr Val Asp Thr Gly Val Gly Glu Trp Ala Phe Trp Glu Thr Lys Lys
1               5                   10                  15

Asn

<210> SEQ ID NO 433
<211> LENGTH: 17
<212> TYPE: PRT
<213> ORGANISM: Reston ebolavirus

<400> SEQUENCE: 433

Lys Ile Glu Pro Asp Val Gly Glu Trp Ala Phe Trp Glu Thr Lys Lys
1               5                   10                  15

Asn

<210> SEQ ID NO 434
<211> LENGTH: 17
<212> TYPE: PRT
<213> ORGANISM: Tai Forest ebolavirus

<400> SEQUENCE: 434

Thr Val Asp Thr Ser Met Gly Glu Trp Ala Phe Trp Glu Thr Lys Lys
1               5                   10                  15

Asn

<210> SEQ ID NO 435
<211> LENGTH: 15
<212> TYPE: PRT
<213> ORGANISM: Zaire ebolavirus

<400> SEQUENCE: 435

Ala Ala Ile Gly Leu Ala Trp Ile Pro Tyr Phe Gly Pro Ala Ala
1               5                   10                  15
```

<210> SEQ ID NO 436
<211> LENGTH: 15
<212> TYPE: PRT
<213> ORGANISM: Sudan ebolavirus

<400> SEQUENCE: 436

Ala Ala Leu Gly Leu Ala Trp Ile Pro Tyr Phe Gly Pro Gly Ala
1               5                   10                  15

<210> SEQ ID NO 437
<211> LENGTH: 15
<212> TYPE: PRT
<213> ORGANISM: Reston ebolavirus

<400> SEQUENCE: 437

Ala Ala Ala Gly Leu Ala Trp Ile Pro Tyr Phe Gly Pro Ala Ala
1               5                   10                  15

<210> SEQ ID NO 438
<211> LENGTH: 15
<212> TYPE: PRT
<213> ORGANISM: Tai Forest ebolavirus

<400> SEQUENCE: 438

Ala Ala Ile Gly Leu Ala Trp Ile Pro Tyr Phe Gly Pro Ala Ala
1               5                   10                  15

<210> SEQ ID NO 439
<211> LENGTH: 15
<212> TYPE: PRT
<213> ORGANISM: Bundibugyo virus

<400> SEQUENCE: 439

Ala Ala Ile Gly Leu Ala Trp Ile Pro Tyr Phe Gly Pro Ala Ala
1               5                   10                  15

<210> SEQ ID NO 440
<211> LENGTH: 14
<212> TYPE: PRT
<213> ORGANISM: Angola marburgvirus

<400> SEQUENCE: 440

Ala Ala Gly Leu Ser Trp Ile Pro Phe Phe Gly Pro Gly Ile
1               5                   10

<210> SEQ ID NO 441
<211> LENGTH: 14
<212> TYPE: PRT
<213> ORGANISM: Popp marburgvirus

<400> SEQUENCE: 441

Ala Ala Gly Leu Ser Trp Ile Pro Phe Phe Gly Pro Gly Ile
1               5                   10

<210> SEQ ID NO 442
<211> LENGTH: 14
<212> TYPE: PRT
<213> ORGANISM: Muscle marburgvirus

<400> SEQUENCE: 442

Ala Ala Gly Leu Ser Trp Ile Pro Phe Phe Gly Pro Gly Ile
1               5                   10

```
<210> SEQ ID NO 443
<211> LENGTH: 14
<212> TYPE: PRT
<213> ORGANISM: RAVN marburgvirus

<400> SEQUENCE: 443

Ala Ala Gly Leu Ser Trp Ile Pro Phe Phe Gly Pro Gly Ile
1               5                   10

<210> SEQ ID NO 444
<211> LENGTH: 14
<212> TYPE: PRT
<213> ORGANISM: CI67 marburgvirus

<400> SEQUENCE: 444

Ala Ala Gly Leu Ser Trp Ile Pro Phe Phe Gly Pro Gly Ile
1               5                   10
```